US008076065B2

(12) United States Patent
Young

(10) Patent No.: US 8,076,065 B2
(45) Date of Patent: Dec. 13, 2011

(54) METHODS AND COMPOSITIONS FOR ASSESSMENT OF PULMONARY FUNCTION AND DISORDERS

(75) Inventor: Robert Peter Young, Auckland (NZ)

(73) Assignee: Synergenz Bioscience Limited, Hong Kong (CN)

( * ) Notice: Subject to any disclaimer, the term of this patent is extended or adjusted under 35 U.S.C. 154(b) by 256 days.

(21) Appl. No.: 11/437,823

(22) Filed: May 19, 2006

(65) Prior Publication Data

US 2007/0099202 A1  May 3, 2007

(30) Foreign Application Priority Data

| May 19, 2005 | (NZ) | ........................................ 540203 |
| Aug. 11, 2005 | (NZ) | ........................................ 541787 |
| Oct. 28, 2005 | (NZ) | ........................................ 543297 |

(51) Int. Cl.
*C12P 19/34* (2006.01)
*C12Q 1/68* (2006.01)

(52) U.S. Cl. ................. 435/6; 436/63; 436/64

(58) Field of Classification Search .................. None
See application file for complete search history.

(56) References Cited

U.S. PATENT DOCUMENTS

| 4,829,052 | A | 5/1989 | Glover et al. |
| 5,455,262 | A | 10/1995 | Schwartz et al. |
| 5,674,754 | A | 10/1997 | Ahrens et al. |
| 5,773,430 | A | 6/1998 | Simon et al. |
| 5,827,662 | A | 10/1998 | Rubin |
| 5,837,492 | A | 11/1998 | Tavtigian |
| 5,840,698 | A | 11/1998 | Campbell et al. |
| 5,844,108 | A | 12/1998 | Meyer |
| 5,851,983 | A | 12/1998 | Sugiyama et al. |
| 5,932,579 | A | 8/1999 | Campbell et al. |
| 5,935,852 | A | 8/1999 | Follettie |
| 6,022,893 | A | 2/2000 | Sakaki et al. |
| 6,033,857 | A | 3/2000 | Tavtigian |
| 6,057,292 | A | 5/2000 | Cunningham et al. |
| 6,057,297 | A | 5/2000 | Politi et al. |
| 6,060,283 | A | 5/2000 | Okura |
| 6,117,869 | A | 9/2000 | Picard et al. |
| 6,171,798 | B1 | 1/2001 | Levine |
| 6,183,963 | B1 | 2/2001 | Sinnett |
| 6,184,022 | B1 | 2/2001 | Seiki et al. |
| 6,187,587 | B1 | 2/2001 | Popoff et al. |
| 6,211,209 | B1 | 4/2001 | Baragi et al. |
| 6,268,142 | B1 | 7/2001 | Duff |
| 6,346,385 | B1 | 2/2002 | Eguchi et al. |
| 6,387,615 | B2 | 5/2002 | Cookson et al. |
| 6,610,510 | B1 | 8/2003 | Valenzuela |
| 6,673,549 | B1 | 1/2004 | Furness |
| 6,677,442 | B1 | 1/2004 | Wang |
| 6,706,478 | B2 | 3/2004 | Duff |
| 6,716,581 | B2 | 4/2004 | Lenz |
| 7,054,758 | B2 | 5/2006 | Gill-Garrison et al. |
| 2002/0197646 | A1 | 12/2002 | Nogee et al. |
| 2004/0106120 | A1 | 6/2004 | Tazi-Ahnini et al. |
| 2004/0152124 | A1 | 8/2004 | Duff |
| 2004/0219548 | A1 | 11/2004 | Young |
| 2004/0241714 | A1 | 12/2004 | Branch |
| 2005/0064454 | A1 | 3/2005 | Young |
| 2005/0196754 | A1 | 9/2005 | Drmanac |
| 2005/0272054 | A1 | 12/2005 | Cargill |
| 2005/0282198 | A1 | 12/2005 | Duff |
| 2006/0122373 | A1 | 6/2006 | Mccarthy |
| 2006/0269946 | A1 | 11/2006 | Young |
| 2006/0275808 | A1 | 12/2006 | Young |
| 2006/0281114 | A1 | 12/2006 | Young |

FOREIGN PATENT DOCUMENTS

| EP | 0 854 191 A2 | 7/1998 |
| EP | 1 043 406 B1 | 6/2006 |
| JP | 2005328707 | 12/2005 |
| NZ | 543520 | 11/2005 |
| NZ | 543985 | 12/2005 |
| NZ | 544034 | 12/2005 |
| NZ | 547579 | 5/2006 |
| WO | WO 01/53537 | 7/2001 |
| WO | WO 02/097127 | 12/2002 |
| WO | WO 02/099134 | 12/2002 |
| WO | WO 2006121351 | 11/2006 |
| WO | WO2006123943 | 11/2006 |
| WO | WO 2006123954 | 11/2006 |
| WO | WO2006123955 | 11/2006 |

OTHER PUBLICATIONS

Schabath (Lung Cancer 2002 vol. 37, pp. 35-40).*
Lee et al. (Carcinogenesis, 2007, vol. 28, pp. 1437-1441) and supplemental data, p. 1-6.*
Campa et al. (Cancer Epidemiol. Biomarkers Prev 2005; 14 (10): 2457-8).*
lonnidis (Plost Med, 2005, 2(8):e124).*
Kroese et al. (Genetics in Medicine, vol. 6 (2004), p. 475-480).*
Hegele et al. (Arterioscler. Thromb. Vasc. Biol. 2002, vol. 22, pp. 1058-1061).*
Wall et al. Nature Review Genetics, 2003, vol. 4, pp. 587-597.*
Cheon, K. T. et al. 2000. Gene polymorphisms of endothelial nitric oxide synthase and angiotensin-converting enzyme in patients with lung cancer. *Lung* 178:351-360.
Fairchild, T. A., et al. 2001. Acidic hydrolysis as a mechanism for the cleavage of the Glu$^{298}$→Asp variant of human endothelial nitric-oxide synthase. *J Biol Chem* 276(28):26674-26679.
Slowik, A, et al. 2005. α1-Antichymotrypsin gene (*serpinaA3*) A/T polymorphism as a risk factor for anneurysmal subarachnoid hemorrhage. *Stroke* 36:737-740.
U.S. Appl. No. 11/432,736, filed May 10, 2006, Young.
U.S. Appl. No. 11/432,770, filed May 2006, Young.
U.S. Appl. No. 11/438,082, filed May 19, 2006, Young.
Minematsu et al. "Genetic polymorphism in Matrix Metalloproteinase-9 and pulmonary emphysema," Biochemical and Biophysical Research Communication vol. 289, pp. 116-119 (Nov. 2001).

(Continued)

*Primary Examiner* — Sarae Bausch
(74) *Attorney, Agent, or Firm* — Davis Wright Tremaine LLP

(57) ABSTRACT

The present invention provides methods for the assessment of risk of developing lung cancer in smokers and non-smokers using analysis of genetic polymorphisms. The present invention also relates to the use of genetic polymorphisms in assessing a subject's risk of developing lung cancer. Nucleotide probes and primers, kits, and microarrays suitable for such assessment are also provided.

2 Claims, 4 Drawing Sheets

OTHER PUBLICATIONS

Nazar-Stewart, V et al., "A population-based study of glutathione S-transferase M1, T1 and P1 genotypes and risk for lung cancer", Lung Cancer 40 (2003) 247-258.

Nomura, A et al., "Prospective study of pulmonary function and lung cancer", Am Rev Respir Dis 1991; 144:307-311.

Park, J A et al., "The human 8-oxoguanine DNA N-glycosylase 1 (hOGG1) DNA repair enzyme and its association with lung cancer risk", Pharmacogenetics 14(2):103-109, Feb. 2004.

Park, J Y et al., "Polymorphism of the DNA repair gene XRCC1 and risk of primary lung cancer", Cancer Epidemiology, Biomarkers & Prevention, vol. 11, Jan. 23-27, 2002.

Poller et al., "DNA polymorphisms of the al-antitrypsin gene region in patients with chronic obstructive pulmonary disease," European Journal of Clinical Investigation, 20:1-7 (1990).

Popanda, O et al., "Specific combinations of DNA repair gene variants and increased risk for non-small cell lung cancer", Carcinogenesis Advance Access, Aug. 27, 2004.

Qiuling, S et al., "Cyclin D1 gene polymorphism and susceptibility to lung cancer in a Chinese population", Carcinogenesis, vol. 24, No. 9, pp. 1499-1503, 2003.

Ratnasinghe, D et al., "Polymorphisms of the DNA repair gene XRCC1 and lung cancer risk", Cancer Epidemiology, Biomarkers & Prevention, vol. 10, 119-123, Feb. 2001.

Rinehart et al., "Human Alpha(1)-Proteinase Inhibitor Binds to Extracellular-Matrix In-Vitro," American Journal of Respiratory Cell and Molecular Biology, vol. 9, No. 6, pp. 666-679 (Dec. 1993).

Sandford et al, "Mutation in the 3' region of the α-1 antitrypsin gene and chronic obstructive pulmonary disease," J. Med. Genet., 34:874-875 (1997).

Sandford et al., "Genetic risk factors for chronic obstructive pulmonary disease," Eur. Respir. J., 10:1380-1391 (1997).

Schwartz, A G, "Genetic predisposition to lung cancer", Chest, 2004; 125:86S-89S.

Shapiro, "Diverse Roles of Macrophage Matrix Metalloproteinases in Tissue Destruction and Tumor Growth," Thromb Haemost., 82:846-849 (1999).

Skillrud, D M et al., "Higher risk of lung cancer in chronic obstructive pulmonary disease", Annals of Internal Medicine, 1986;105:503-507.

Smith, I, "Spirometry's COPD-lung cancer connection", The Journal for Respiratory Care Practitioners, Dec./Jan. 1996, pp. 70-71.

Sorsa et al., "Doxycycline in the Protection of Serum Alpha-1-Antitrypsin from Human Neutrophil Collagenase and Gelatinase," Antimicrobial Agents and Chemotherapy, vol. 37, No. 3, pp. 592-594 (1993).

Spitz, M R et al., "Modulation of nucleotide excision repair capacity by XPD polymorphisms in lung cancer patients", Cancer Research 61, 1354-1357, Feb. 15, 2001.

Syrris et al., "Transforming growth factor-β1 gene polymorphisms and coronary artery disease," Clinical Science, 95:659-667 (1998).

Tockman, M S et al., "Airways obstruction and the risk for lung cancer", Annals of Internal Medicine, 1987;106:512-518.

Vineis, P et al., "CYP1A $T^{3801}$ C polymorphism and lung cancer: a pooled analysis of 2,451 cases and 3,358 controls", Int. J. Cancer: 104, 650-657 (2003).

Walter et al., "Environmental and genetic risk factors and gene-environment interactions in the pathogenesis of chronic lung disease," Environmental Health Perspectives, vol. 108, Suppl. 4, pp. 733-742 (2000).

Wang, J et al., "Association of GSTM1, CYP1A1 and CYP2E1 genetic polymorphisms with susceptibility to lung adenocarcinoma: a case-control study in Chinese population", Cancer Science, 94(5):448-52, May 2003.

Wang, L-E et al., "Fas A670G polymorphism, apoptotic capacity in lymphocyte cultures, and risk of lung cancer", Lung Cancer (2003) 42, 1-8.

Wang, Y et al., "From genotype to phenotype: correlating XRCC1 polymorphisms with mutagen sensitivity", DNA Repair 2 (2003) 901-908.

Wikman, H et al., "hOGG1 polymorphism and loss of heterozygosity (LOH): significance for lung cancer susceptibility in a Caucasian population", Int. J. Cancer 88, 932-937 (2000).

Wu, X et al., "Cytochrome P450 2E1 DraI polymorphisms in lung cancer in minority populations", Cancer Epidemiol Biomarkers Prev. Jan. 1998;7(1):13-8.

Wu, X et al., "Genetic susceptibility to tobacco-related cancer", Oncogene, (2004), 23, 6500-6523.

Ye, S., "Polymorphism in matrix metalloproteinase gene promoters: implication in regulation of gene expression and susceptibility of various diseases," Matrix Biology vol. 19, pp. 623-629 (2000).

Yim et al., "Genetic susceptibility to chronic obstructive pulmonary disease in Koreans: combined analysis of polymorphic genotypes for microsomal epoxide hydrolase and glutathione S-transferase M1 and T1," Thorax, 55:121-125 (2000).

Zhang et al., "Functional polymorphism in the regulatory region of,gelatinase B gene in relation to severity of coronary artherosclerosis," Circulation, vol. 99, pp. 1788-1794 (1999).

Zhang et al., "Genetic variation at the matrix metalloproteinase-9 locus on chromosome 20q12.2-13.1," Hum. Genet., 105:418-423 (1999).

Zhou, W et al, "Polymorphisms in the DNA repair genes XRCC1 and ERCC2, smoking, and lung cancer risk", Cancer Epidemiology, Biomarkers & Prevention, vol. 12, 359-365, Apr. 2003.

Zhou, W et al., "Gene environment interaction for the ERCC2 polymorphisms and cumulative cigarette smoking exposure in lung cancer", Cancer Research 62, 1377-1381, Mar. 1, 2002.

Zhou, W et al., "Genetic polymorphisms in N-acetyltransferase-2 and microsomal epoxide hydrolase, cumulative cigarette smoking, and lung cancer", Cancer Epidemiology, Biomarkers and Prevention, vol. 11, Jan. 15-21, 2002.

Zienolddiny, S et al., Polymorphisms of the interleukin-1 β gene are associated with increased risk of non-small cell lung cancer, Int J Cancer, Apr. 10, 2004; 109(3):353-6.

International Search Report, International Application No. PCT/NZ02/00106, filed Jun. 5, 2002, 4 pages.

Alberg, A J et al., "Epidemiology of Lung Cancer", Chest, 123, 1, Jan. 2003 Supplement, 21S-49S.

Anthonisen, N R, "Prognosis in chronic obstructive pulmonary disease: results from multicenter clinical trials", Rev Respir Dis 1989; 140:S95-S99.

Barnes, "Molecular genetics of chronic obstructive pulmonary disease," Thorax 54:245-252 (1999).

Butkiewicz et al., "GSTM1, GSTP1, CYP1A1 and CYP2D6 polymorphisms in lung cancer patients from an environmentally polluted region of Poland: correlation with lung DNA adduct levels," European Journal of Cancer Prevention, (abstract) 8:315-323 (1999).

Cambien et al., "Polymorphisms of the Transforming Growth Factor-β1 Gene in Relation to Myocardial Infarction and Blood Pressure," Hypertension 28:881-887 (1996).

Cantlay, A M et al., "Heterogeneous expression and polymorphic genotype of glutathione S-transferases in human lung", Thorax, 1994:49:1010-1014.

David-Beabes, G L et al., "No association between XPD (Lys751Gln) polymorphism or the XRCC3 (Thr241Met) polymorphism and lung cancer risk", Cancer Epidemiology, Biomarkers and Prevention, vol. 10, 911-912, Aug. 2001.

Dialyna, I A et al., "Genetic polymorphisms of CYP1A1, GSTM1 and GSTT1 genes and lung cancer risk", Oncol Rep., Nov.-Dec. 2003;10(6):1829-35.

Divine, K K et al., "The XRCC1 399 glutamine allele is a risk factor for adenocarcinoma of the lung", Mutation Research 461 (2001) 273-278.

Dunleavey et al., "Rapid genotype analysis of the matrix metalloproteinase-1 gene 1G/2G polymorphism that is associated with risk of cancer," Matrix Biology, 19:175-177 (2000).

Folz et al., "Elevated Levels of Extracellular Superoxide Dismutase in Chronic Lung Disease and Characterization of Genetic Variants," Chest, 111:74S (1997).

Goode, E L et al., "Polymorphisms in DNA repair genes and associations with cancer risk", Cancer Epidemiology, Biomarkers and Prevention, vol. 11, 1513-1530, Dec. 2002.

Greisenbach et al., "Anti-inflammatory gene therapy directed at the airway epithelium," Gene Therapy, vol. 7, No. 4, pp. 306-313 (Feb. 2000).

Harms, C et al., "Polymorphisms in DNA repair genes, chromosome aberrations, and lung cancer", Environmental and Molecular Mutagenesis 44:74-82 (2004).

Harrison et al., "Frequency of glutathione 5-transferase M1 deletion in smokers with emphysema and lung cancer," Human & Experimental Toxicology 16:356-360 (1997).

Hirano et al., "Tissue inhibitor of metalloproteinase-2 gene polymorphisms in chronic obstructive pulmonary disease," European Respiratory Journal, vol. 18, pp. 748-752 (2001).

Houlston, R S, "CYP1A1 polymorphisms and lung cancer risk: a meta-analysis", Pharmacogenetics, Mar. 2000; 10(2):105-14.

Hung, R J et al., "CYP1A1 and GSTM1 genetic polymorphisms and lung cancer risk in Caucasian non-smokers: a pooled analysis", Carcinogenesis, 24(5):875-82, May 2003.

Joos et al., "The role of matrix metalloproteinase polymorphisms in the rate of decline in lung function," Human Molecular Genetics, vol. 11, pp. 569-576 (2002).

Jormsjö et al., "Allele-Specific Regulation of Matrix Metlaloproteinase-12 Gene Activity is Associated with Coronary Artery Luminal Dimensions in Diabetic Patients with Manifest Coronary Artery Disease," Cir. Res. 86:998-1003 (2000).

Kalsheker et al., "Deoxyribonucleic acid (DNA) polymorphism of the a1-antitrypsin gene in chronic lung disease," British Medical Journal, 294:1511-1514 (1987).

Kiyohara, C. et al., "Risk modification by CYP1A1 and GSTM1 polymorphisms in the association of environmental tobacco smoke and lung cancer: a case-control study in Japanese non-smoking women", International Journal of Cancer, 107(1):139-44, Oct. 20, 2003.

Le Marchand, L et al., "Association of the hOGG1 Ser326Cys polymorphism with lung cancer risk", Cancer Epidemiology, Biomarkers & Prevention, vol. 11, 409-412, Apr. 2002.

Le Marchand, L et al., "Associations of CYP1A1, GSTM1, and CYP2E1 polymorphisms with lung cancer suggest cell type specificities to tobacco carcinogens", Cancer Res., Nov. 1, 1998;58(21):4858-63.

Le Marchand, L et al., "Pooled analysis of the CYP1A1 exon 7 polymorphism and lung cancer (United States)", Cancer Causes and Control, 14:339-346, 2003.

Liang, G et al., "Sequence variations in the dna repair gene XPD and risk of lung cancer in a Chinese population", Int. J. Cancer, 105, 669-673 (2003).

Marklund et al., "Two variants of extracellular-superoxide dismutase: relationship to cardiovascular risk factors in an unselected middle-aged population," Journal of Internal Medicine, 242:5-14 (1997).

Mayne, S T et al., "Previous lung disease and risk of lung cancer among men and women nonsmokers", American Journal of Epidemiology, vol. 149, No. 1, 1999, pp. 13-20.

Campa, et al. 2004. "Association of a common polymorphism in the cyclooxygenase 2 gene with risk of non-small cell lung cancer." *Carcinogenesis 200402 GB* 25(2): 229-235.

Fang, et al. 2005. "Polymorphisms in the MMP1 and MMP3 promoter and non-small cell lung carcinoma in North China." *Carcinogenesis* (Oxford) 26(2): 481-486.

Gurubhagavatula, et al. 2004. "XPD and XRCC1 genetic polymorphism are prognostic factors in advanced non-small-cell lung cancer patients treated with platinum chemotherapy." *Journal of Clinical Oncology: Official Journal of the American Society of Clinical Oncology* 22(13): 2594-2601.

Hu, et al. 2005. "A common polymorphism in the 3'UTR of cyclooxygenase 2/prostaglandin synthase 2 gene and risk of lung cancer in a Chinese population." *Lung Cancer*, Elsevier, Amsterdam, NL 48(1): 11-17.

Landi, et al. 2005. "A database of single-nucleotide polymorphisms and a genotyping microarray for genetic epidemiology of lung cancer." *Experimental Lung Research* 31(2): 223-258.

Oyama, et al. 2003. "Evidence-based prevention (EBP): approach to lung cancer prevention based on cytochrome 1A1 and cytochrome 2E1 polymorphism." *Anticancer Research* 23(2C): 1731-1737.

Popanda, et al. 2004. "Specific combinations of DNA repair gene variants and increased risk for non-small cell lung cancer." *Carcinogenosis* 25(12): 2433-2441.

Seifart, et al. 2005. "TNF-[alpha], TNF-[beta], IL-6, and IL-10 polymorphisms in patients with lung cancer." *Disease Markers*, Wiley, Chichester, GB 21(3): 157-165.

Tesauro, et al. 2000. "Intracellular processing of endothelial nitric oxide synthase isoforms associated with differences in severity of cardiopulmonary diseases: cleavage of proteins with aspirate vs. glutamate at position 298." *Proceedings of the National Academy of Sciences of the United States of America 20000314 US* 97: 2832-2835.

Young, et al. 2006. "Functional variants of antioxidant genes in smokers with COPD and those with normal lung function." *Thorax, BMJ Publishing Group*, GB 61(5): 394-399.

Zhu, et al. 2001. "A single nucleotide polymorphism in the matrix metalloproteinase-1 promoter enhances lung cancer susceptibility." *Cancer Research* 61(21): 7825-7829.

Zienolddiny, et al. 2004. "Polymorphisms of the interleukin-1 beta gene are associated with increased risk of non-small cell lung cancer." *International Journal of Cancer, Journal International du Cancer* 109(3): 353-356.

Dockery, et al. 1997. "Risk of lung cancer from environmental exposure to tobacco smoke," *Cancer Causes and Control* 8:333-345.

Utts, Jessica 2003. What educated citizens should know about statistics and probability. *The American Statistician* 57(2):74-79.

\* cited by examiner

SEQUENCE LISTING

```
<160> NUMBER OF SEQ ID NOS: 145

<210> SEQ ID NO 1
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 1
tcgtgagaat gtcttcccat t                                              21

<210> SEQ ID NO 2
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 2
tcttggattg atttgagata agtgaaatc                                      29

<210> SEQ ID NO 3
<211> LENGTH: 30
<212> TYPE: DNA
<213> ORGANISM: Artificial Sequence
<220> FEATURE:
```

<223> OTHER INFORMATION: Synthetic nucleic acid sequence

<400> SEQUENCE: 3
acgttggatg aaaccagagg gaagcaaagg    30

<210> SEQ ID NO 4
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 4
acgttggatg tcattggttg tgctgcacct    30

<210> SEQ ID NO 5
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 5
acgttggatg caccaggaac cgtttatggc    30

<210> SEQ ID NO 6
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 6
acgttggatg agcagctaga atcagaggag    30

<210> SEQ ID NO 7
<211> LENGTH: 31
<212> TYPE: DNA
<213> ORGANISM: Artificial Sequence
<220> FEATURE:
<223> OTHER INFORMATION: Synthetic nucleic acid sequence

<400> SEQUENCE: 7
acgttggatg gtcaatgaag agaacttggt c    31

<210> SEQ ID NO 8
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 8
acgttggatg aatgtttatt gtagaaaacc    30

<210> SEQ ID NO 9
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 9
acgttggatg gggtattcat aagctgaaac    30

<210> SEQ ID NO 10

```
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 10
acgttggatg ccttcaagtt cagtggtcag                                30

<210> SEQ ID NO 11
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 11
acgttggatg gtgattatct ttggcatggg                                30

<210> SEQ ID NO 12
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 12
acgttggatg ggatagccag gaagagaaag                                30

<210> SEQ ID NO 13
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 13
acgttggatg ccctatttct ttgtcttcac                                30

<210> SEQ ID NO 14
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 14
acgttggatg cttgggataa tttggctctg                                30

<210> SEQ ID NO 15
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 15
acgttggatg ggaacccttt ctgcgctttg                                30

<210> SEQ ID NO 16
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 16
```

-continued acgttggatg cctacaggtg ctgttcagtg                                               30

<210> SEQ ID NO 17
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 17
acgttggatg cctgccaaag aagaaacacc                                               30

<210> SEQ ID NO 18
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 18
acgttggatg acgtctgcag gtatgtattc                                               30

<210> SEQ ID NO 19
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 19
acgttggatg gttcttaatt cataggttgc                                               30

<210> SEQ ID NO 20
<211> LENGTH: 32
<212> TYPE: DNA
<213> ORGANISM: Artificial Sequence
<220> FEATURE:
<223> OTHER INFORMATION: Synthetic nucleic acid sequence

<400> SEQUENCE: 20
acgttggatg cttcatttct catcatattt tc                                            32

<210> SEQ ID NO 21
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 21
acgttggatg taggtgtctc ccctgtaag                                                30

<210> SEQ ID NO 22
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 22
acgttggatg tcctctccag agtgatcaag                                               30

<210> SEQ ID NO 23
<211> LENGTH: 30
<212> TYPE: DNA
<213> ORGANISM: Artificial Sequence
<220> FEATURE:

<223> OTHER INFORMATION: Synthetic nucleic acid sequence

<400> SEQUENCE: 23
acgttggatg attttctcct cagaggctcc                                    30

<210> SEQ ID NO 24
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 24
acgttggatg tgtctgtatt gagggtgtgg                                    30

<210> SEQ ID NO 25
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 25
acgttggatg ttgtggctgc aacatgagag                                    30

<210> SEQ ID NO 26
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 26
acgttggatg ctatggcgca acatctgtac                                    30

<210> SEQ ID NO 27
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 27
acgttggatg actgtagttt ccctagtccc                                    30

<210> SEQ ID NO 28
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 28
acgttggatg agtcagcaga gagactaggg                                    30

<210> SEQ ID NO 29
<211> LENGTH: 31
<212> TYPE: DNA
<213> ORGANISM: Artificial Sequence
<220> FEATURE:
<223> OTHER INFORMATION: Synthetic nucleic acid sequence

<400> SEQUENCE: 29
acgttggatg gagttgagaa tggagagaat g                                  31

<210> SEQ ID NO 30

```
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 30
acgttggatg tcaagtgggc tgttagggtg                                    30

<210> SEQ ID NO 31
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 31
acgttggatg tgctgcgtgg tgggcgtgtg                                    30

<210> SEQ ID NO 32
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 32
acgttggatg ggccttgcac tcgctctcg                                     29

<210> SEQ ID NO 33
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 33
acgttggatg aaacggtcgc ttcgacgtgc                                    30

<210> SEQ ID NO 34
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 34
acgttggatg acctcaagga ccagctcgg                                     29

<210> SEQ ID NO 35
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 35
acgttggatg actgaagctc cacaatttgg                                    30

<210> SEQ ID NO 36
<211> LENGTH: 31
<212> TYPE: DNA
<213> ORGANISM: Artificial Sequence
<220> FEATURE:
<223> OTHER INFORMATION: Synthetic nucleic acid sequence

<400> SEQUENCE: 36
```

```
acgttggatg gccactctag tactatatct g                                    31
```

<210> SEQ ID NO 37
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 37

```
acgttggatg cagacattca caattgattt                                      30
```

<210> SEQ ID NO 38
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 38

```
acgttggatg gatagttcca aacatgtgcg                                      30
```

<210> SEQ ID NO 39
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 39

```
acgttggatg taaggagtgg gtgctggact                                      30
```

<210> SEQ ID NO 40
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 40

```
acgttggatg aggataagga gcagggttgg                                      30
```

<210> SEQ ID NO 41
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 41

```
ttcttggttc aggagag                                                    17
```

<210> SEQ ID NO 42
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 42

```
ttcttggttc aggagagc                                                   18
```

<210> SEQ ID NO 43
<211> LENGTH: 19
<212> TYPE: DNA
<213> ORGANISM: Artificial Sequence
<220> FEATURE:

```
<223> OTHER INFORMATION: Synthetic nucleic acid sequence

<400> SEQUENCE: 43
gcaatctgct ctatcctct                                               19

<210> SEQ ID NO 44
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 44
gcaatctgct ctatcctctt                                              20

<210> SEQ ID NO 45
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 45
attcaagctt gccaaagtaa tc                                           22

<210> SEQ ID NO 46
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 46
attcaagctt gccaaagtaa tct                                          23

<210> SEQ ID NO 47
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 47
cataagctga aacttctgg                                               19

<210> SEQ ID NO 48
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 48
cataagctga aacttctggc                                              20

<210> SEQ ID NO 49
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 49
ggaagtgtat cggtgagacc                                              20

<210> SEQ ID NO 50
```

```
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 50
ggaagtgtat cggtgagacc a                                              21

<210> SEQ ID NO 51
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 51
tgacaaatac tggttaatta gca                                            23

<210> SEQ ID NO 52
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 52
tgacaaatac tggttaatta gcaa                                           24

<210> SEQ ID NO 53
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 53
gctcctgagc atggcgg                                                   17

<210> SEQ ID NO 54
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 54
gctcctgagc atggcggc                                                  18

<210> SEQ ID NO 55
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 55
tacttattta cgcttgaacc tc                                             22

<210> SEQ ID NO 56
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 56
```

```
tacttattta cgcttgaacc tca                                              23

<210> SEQ ID NO 57
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 57
cttaattcat aggttgcaat ttt                                              23

<210> SEQ ID NO 58
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 58
cttaattcat aggttgcaat ttta                                             24

<210> SEQ ID NO 59
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 59
acatcaccct cacttac                                                     17

<210> SEQ ID NO 60
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 60
acatcaccct cacttacc                                                    18

<210> SEQ ID NO 61
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 61
aattgacaga gagctcc                                                     17

<210> SEQ ID NO 62
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 62
aattgacaga gagctccc                                                    18

<210> SEQ ID NO 63
<211> LENGTH: 20
<212> TYPE: DNA
<213> ORGANISM: Artificial Sequence
<220> FEATURE:
```

<223> OTHER INFORMATION: Synthetic nucleic acid sequence

<400> SEQUENCE: 63
atgagaggct cacagacgtt                                               20

<210> SEQ ID NO 64
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 64
atgagaggct cacagacgtt c                                             21

<210> SEQ ID NO 65
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 65
ggcatcaagc tcttccctgg c                                             21

<210> SEQ ID NO 66
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 66
ggcatcaagc tcttccctgg cc                                            22

<210> SEQ ID NO 67
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 67
gaatgttacc tctcctg                                                  17

<210> SEQ ID NO 68
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 68
gaatgttacc tctcctga                                                 18

<210> SEQ ID NO 69
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 69
gcactcagag cgcaagaag                                                19

<210> SEQ ID NO 70

```
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 70
gcactcagag cgcaagaagc                                                   20

<210> SEQ ID NO 71
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 71
gctgctgcag gccccagatg a                                                 21

<210> SEQ ID NO 72
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 72
gctgctgcag gccccagatg at                                                22

<210> SEQ ID NO 73
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 73
cacaatttgg tgaattatca a                                                 21

<210> SEQ ID NO 74
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 74
cacaatttgg tgaattatca at                                                22

<210> SEQ ID NO 75
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 75
ttcttacaac acaaaatcaa atc                                               23

<210> SEQ ID NO 76
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 76
```

-continued

```
ttcttacaac acaaaatcaa atct                                            24
```

<210> SEQ ID NO 77
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 77

```
tcggcggctg ccctccc                                                    17
```

<210> SEQ ID NO 78
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 78

```
tcggcggctg ccctccca                                                   18
```

<210> SEQ ID NO 79
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 79

```
ttcttggttc aggagaggt                                                  19
```

<210> SEQ ID NO 80
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 80

```
gcaatctgct ctatcctctg c                                               21
```

<210> SEQ ID NO 81
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 81

```
attcaagctt gccaaagtaa tcgga                                           25
```

<210> SEQ ID NO 82
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 82

```
cataagctga aacttctggg a                                               21
```

<210> SEQ ID NO 83
<211> LENGTH: 22
<212> TYPE: DNA
<213> ORGANISM: Artificial Sequence
<220> FEATURE:

```
<223> OTHER INFORMATION: Synthetic nucleic acid sequence

<400> SEQUENCE: 83
ggaagtgtat cggtgagacc gt                                           22

<210> SEQ ID NO 84
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 84
tgacaaatac tggttaatta gcagt                                        25

<210> SEQ ID NO 85
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 85
gctcctgagc atggcggga                                               19

<210> SEQ ID NO 86
<211> LENGTH: 24
<212> TYPE: DNA
<213> ORGANISM: Artificial Sequence
<220> FEATURE:
<223> OTHER INFORMATION: Synthetic nucleic acid sequence

<400> SEQUENCE: 86
tacttattta cgcttgaacc tcga                                         24

<210> SEQ ID NO 87
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 87
cttaattcat aggttgcaat tttgt                                        25

<210> SEQ ID NO 88
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 88
acatcaccct cacttactg                                               19

<210> SEQ ID NO 89
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 89
aattgacaga gagctcctg                                               19

<210> SEQ ID NO 90
```

<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 90
atgagaggct cacagacgtt tc                                        22

<210> SEQ ID NO 91
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 91
ggcatcaagc tcttccctgg ctg                                       23

<210> SEQ ID NO 92
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 92
gaatgttacc tctcctggc                                            19

<210> SEQ ID NO 93
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 93
gcactcagag cgcaagaagg ggc                                       23

<210> SEQ ID NO 94
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 94
gctgctgcag gccccagatg agc                                       23

<210> SEQ ID NO 95
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 95
cacaatttgg tgaattatca aat                                       23

<210> SEQ ID NO 96
<211> LENGTH: 25
<212> TYPE: DNA
<213> ORGANISM: Artificial Sequence
<220> FEATURE:
<223> OTHER INFORMATION: Synthetic nucleic acid sequence

<400> SEQUENCE: 96
ttcttacaac acaaaatcaa atcac                                   25

<210> SEQ ID NO 97
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 97
tcggcggctg ccctcccgga                                         20

<210> SEQ ID NO 98
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 98
acgttggatg aggtagctga agaggcaaac                              30

<210> SEQ ID NO 99
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 99
acgttggatg gcctatagcc tctaaaacgc                              30

<210> SEQ ID NO 100
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 100
acgttggatg ctttcaattt gtggaggctg                              30

<210> SEQ ID NO 101
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 101
acgttggatg tgtgcactca tttgtggacg                              30

<210> SEQ ID NO 102
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 102
acgttggatg gtagctctcc aggcatcaac                              30

<210> SEQ ID NO 103
<211> LENGTH: 30
<212> TYPE: DNA
<213> ORGANISM: Artificial Sequence
<220> FEATURE:

<223> OTHER INFORMATION: Synthetic nucleic acid sequence

<400> SEQUENCE: 103
acgttggatg gtacctggtt cccccttttc                                                30

<210> SEQ ID NO 104
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 104
acgttggatg acaccaggcg tttgatgttg                                                30

<210> SEQ ID NO 105
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 105
acgttggatg aaaaacgcca acagcatcgg                                                30

<210> SEQ ID NO 106
<211> LENGTH: 29
<212> TYPE: DNA
<213> ORGANISM: Artificial Sequence
<220> FEATURE:
<223> OTHER INFORMATION: Synthetic nucleic acid sequence

<400> SEQUENCE: 106
acgttggatg aggcggagat gggtgtgtc                                                 29

<210> SEQ ID NO 107
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 107
acgttggatg agtctagggt ggggtatgtg                                                30

<210> SEQ ID NO 108
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 108
acgttggatg atgtgtggat tcacagctcg                                                30

<210> SEQ ID NO 109
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 109
acgttggatg gggttggcaa ctctaaaagg                                                30

<210> SEQ ID NO 110

<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 110
acgttggatg ctctgaaatc agtgctgctc        30

<210> SEQ ID NO 111
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 111
acgttggatg atggtcaaca gtgttgccag        30

<210> SEQ ID NO 112
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 112
acgttggatg cacctcttga ttgctttccc        30

<210> SEQ ID NO 113
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 113
acgttggatg acccggcctt cctgatcatg        30

<210> SEQ ID NO 114
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 114
acgttggatg attccatgga ggctggatag        30

<210> SEQ ID NO 115
<211> LENGTH: 30
<212> TYPE: DNA
<213> ORGANISM: Artificial Sequence
<220> FEATURE:
<223> OTHER INFORMATION: Synthetic nucleic acid sequence

<400> SEQUENCE: 115
acgttggatg gacaacacta ctaaggcttc        30

<210> SEQ ID NO 116
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 116

```
aaaaggtttc tccccc                                                 17

<210> SEQ ID NO 117
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 117
aaaaggtttc tcccccc                                                18

<210> SEQ ID NO 118
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 118
aggctgcttc ttggact                                                17

<210> SEQ ID NO 119
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 119
aggctgcttc ttggactc                                               18

<210> SEQ ID NO 120
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 120
caaagatggg cgtgatg                                                17

<210> SEQ ID NO 121
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 121
caaagatggg cgtgatga                                               18

<210> SEQ ID NO 122
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 122
gccagccccg ggacgga                                                17

<210> SEQ ID NO 123
<211> LENGTH: 18
<212> TYPE: DNA
<213> ORGANISM: Artificial Sequence
<220> FEATURE:
```

-continued

<223> OTHER INFORMATION: Synthetic nucleic acid sequence

<400> SEQUENCE: 123
gccagccccg ggacggac                   18

<210> SEQ ID NO 124
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 124
atgggtgtgt ctgccgg                    17

<210> SEQ ID NO 125
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 125
atgggtgtgt ctgccgga                   18

<210> SEQ ID NO 126
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 126
ggctgtaagg aaatctggg                  19

<210> SEQ ID NO 127
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 127
ggctgtaagg aaatctggga                 20

<210> SEQ ID NO 128
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 128
ccttatcctc ctcctgggaa                 20

<210> SEQ ID NO 129
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 129
ccttatcctc ctcctgggaa a               21

<210> SEQ ID NO 130

```
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 130
tgtttcattt ctataggcga                                               20

<210> SEQ ID NO 131
<211> LENGTH: 21
<212> TYPE: DNA
<213> ORGANISM: Artificial Sequence
<220> FEATURE:
<223> OTHER INFORMATION: Synthetic nucleic acid sequence

<400> SEQUENCE: 131
tgtttcattt ctataggcga t                                             21

<210> SEQ ID NO 132
<211> LENGTH: 17
<212> TYPE: DNA
<213> ORGANISM: Artificial Sequence
<220> FEATURE:
<223> OTHER INFORMATION: Synthetic nucleic acid sequence

<400> SEQUENCE: 132
cctatcccta cttcccc                                                  17

<210> SEQ ID NO 133
<211> LENGTH: 18
<212> TYPE: DNA
<213> ORGANISM: Artificial Sequence
<220> FEATURE:
<223> OTHER INFORMATION: Synthetic nucleic acid sequence

<400> SEQUENCE: 133
cctatcccta cttccccc                                                 18

<210> SEQ ID NO 134
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 134
aaaaggtttc tcccccga                                                 19

<210> SEQ ID NO 135
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 135
aggctgcttc ttggactga                                                19

<210> SEQ ID NO 136
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 136
```

```
caaagatggg cgtgatggc                                                19
```

<210> SEQ ID NO 137
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 137

```
gccagccccg ggacggagt                                                19
```

<210> SEQ ID NO 138
<211> LENGTH: 19
<212> TYPE: DNA
<213> ORGANISM: Artificial Sequence
<220> FEATURE:
<223> OTHER INFORMATION: Synthetic nucleic acid sequence

<400> SEQUENCE: 138

```
atgggtgtgt ctgccgggt                                                19
```

<210> SEQ ID NO 139
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 139

```
ggctgtaagg aaatctgggg gt                                            22
```

<210> SEQ ID NO 140
<211> LENGTH: 22
<212> TYPE: DNA
<213> ORGANISM: Artificial Sequence
<220> FEATURE:
<223> OTHER INFORMATION: Synthetic nucleic acid sequence

<400> SEQUENCE: 140

```
ccttatcctc ctcctgggaa ga                                            22
```

<210> SEQ ID NO 141
<211> LENGTH: 23
<212> TYPE: DNA
<213> ORGANISM: Artificial Sequence
<220> FEATURE:
<223> OTHER INFORMATION: Synthetic nucleic acid sequence

<400> SEQUENCE: 141

```
tgtttcattt ctataggcga gga                                           23
```

<210> SEQ ID NO 142
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 142

```
cctatcccta cttccccttc                                               20
```

<210> SEQ ID NO 143
<211> LENGTH: 20
<212> TYPE: DNA
<213> ORGANISM: Artificial Sequence
<220> FEATURE:

```
<223> OTHER INFORMATION: Synthetic nucleic acid sequence

<400> SEQUENCE: 143
ctgccctact tgattgatgg                                              20

<210> SEQ ID NO 144
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 144
atcttctcct cttctgtctc                                              20

<210> SEQ ID NO 145
<211> LENGTH: 20
<212> TYPE: DNA
<213> ORGANISM: Artificial Sequence
<220> FEATURE:
<223> OTHER INFORMATION: Synthetic nucleic acid sequence

<400> SEQUENCE: 145
ttctggattg tagcagatca                                              20
```

METHODS AND COMPOSITIONS FOR ASSESSMENT OF PULMONARY FUNCTION AND DISORDERS

CROSS-REFERENCE TO RELATED APPLICATIONS

This application claims priority to: New Zealand Application No. 540203, filed May 19, 2005; New Zealand Application No. 541787, filed Aug. 11, 2005; and New Zealand Application No. 543297, filed Oct. 28, 2005. All of the foregoing applications are incorporated by reference in their entireties.

FIELD OF THE INVENTION

The present invention is concerned with methods for assessment of pulmonary function and/or disorders, and in particular for assessing risk of developing lung cancer in smokers and non-smokers using analysis of genetic polymorphisms and altered gene expression.

BACKGROUND OF THE INVENTION

Lung cancer is the second most common cancer and has been attributed primarily to cigarette smoking. Other factors contributing to the development of lung cancer include occupational exposure, genetic factors, radon exposure, exposure to other aero-pollutants and possibly dietary factors (Alberg, A. J. et al. Epidemiology of lung cancer. *Chest* 123:21s-49s, (2003), herein incorporated by reference in its entirety). Non-smokers are estimated to have a one in 400 risk of lung cancer (0.25%). Smoking increases this risk by approximately 40 fold, such that smokers have a one in 10 risk of lung cancer (10%) and in long-term smokers the life-time risk of lung cancer has been reported to be as high 10-15% (Schwartz, A. G. Genetic predisposition to lung cancer. *Chest* 125:86s-89s, (2004), herein incorporated by reference in its entirety). Genetic factors are thought to play some part as evidenced by a weak familial tendency (among smokers) and the fact that only the minority of smokers get lung cancer. It is generally accepted that the majority of this genetic tendency comes from low penetrant high frequency polymorphisms, that is, polymorphisms which are common in the general population that in context of chronic smoking exposure contribute collectively to cancer development (Schwartz, A G. 2004; Wu, X. et al. Genetic susceptibility to tobacco-related cancer. *Oncogene* 23:6500-6523, (2004), each of the foregoing which is incorporated by reference in its entirety). Several epidemiological studies have reported that impaired lung function (Anthonisen, N. R. Prognosis in COPD: Results from multi-center clinical trials. *Am Rev Respir Dis* 140:s95-s99, (1989); Skillrud, D. M. et al. Higher risk of lung cancer in COPD: A prospective matched controlled study. *Ann Int Med* 105:503-507, (1986); Tockman, M. S. et al. Airways obstruction and the risk for lung cancer. *Ann Int Med* 106: 512-518, (1987); Kuller, L. H. et al. Relation of forced expiratory volume in one second to lung cancer mortality in the MRFIT. *Am J Epidmiol* 132:265-274, (1990); Nomura, A. et al. Prospective study of pulmonary function and lung cancer. *Am Rev Respir Dis* 144:307-311, (1991); each of the foregoin which is incorporated by reference in its entirety) or symptoms of obstructive lung disease (Mayne, S. T. et al. Previous lung disease and risk of lung cancer among men and women nonsmokers. *Am J Epidemiol* 149:13-20, (1999), herein incorporated by reference in its entirety) are independent risk factors for lung cancer and are possibly more relevant than smoking exposure dose.

Despite advances in the treatment of airways disease, current therapies do not significantly alter the natural history of lung cancer, which can include metastasis and progressive loss of lung function causing respiratory failure and death. Although cessation of smoking can be expected to reduce this decline in lung function, it is probable that if this is not achieved at an early stage, the loss is considerable and symptoms of worsening breathlessness likely cannot be averted. Analogous to the discovery of serum cholesterol and its link to coronary artery disease, there is a need to better understand the factors that contribute to lung cancer so that tests that identify at risk subjects can be developed and that new treatments can be discovered to reduce the adverse effects of lung cancer. The early diagnosis of lung cancer or of a propensity to developing lung cancer enables a broader range of prophylactic or therapeutic treatments to be employed than can be employed in the treatment of late stage lung cancer. Such prophylactic or early therapeutic treatment is also more likely to be successful, achieve remission, improve quality of life, and/or increase lifespan.

To date, a number of biomarkers useful in the diagnosis and assessment of propensity towards developing various pulmonary disorders have been identified. These include, for example, single nucleotide polymorphisms including the following: A-82G in the promoter of the gene encoding human macrophage elastase (MMP12); T→C within codon 10 of the gene encoding transforming growth factor beta (TGFβ); C+760G of the gene encoding superoxide dismutase 3 (SOD3); T-1296C within the promoter of the gene encoding tissue inhibitor of metalloproteinase 3 (TIMP3); and polymorphisms in linkage disequilibrium with these polymorphisms, as disclosed in PCT International Application PCT/NZ02/00106 (published as WO 02/099134 and herein incorporated by reference in its entirety).

SUMMARY OF THE INVENTION

In some aspects, the present invention is primarily based on the finding that certain polymorphisms are found more often in subjects with lung cancer than in control subjects. Analysis of these polymorphisms reveals an association between polymorphisms and the subject's risk of developing lung cancer.

Thus, according to some aspects there is provided a method of determining a subject's risk of developing lung cancer including analyzing a sample from said subject for the presence or absence of one or more polymorphisms selected from the group consisting of: Asp 298 Glu in the gene encoding Nitric oxide synthase 3 (NOS3); −786 T/C in the promoter of the gene encoding NOS3; Arg 312 Gln in the gene encoding Superoxide dismutase 3 (SOD3); Ala 15 Thr in the gene encoding Anti-chymotrypsin (ACT); Asn 357 Ser A/G in the gene encoding Matrix metalloproteinase 12 (MMP12); 105 A/C in the gene encoding Interleukin-18 (IL-18); −133 G/C in the promoter of the gene encoding Interleukin-18; 874 A/T in the gene encoding Interferon gamma (IFNγ); −765 G/C in the gene encoding Cyclooxygenase 2 (COX2); −447 G/C in the gene encoding Connective tissue growth factor (CTGF); −221 C/T in the gene encoding Mucin 5AC (MUC5AC); +161 G/A in the gene encoding Mannose binding lectin 2 (MBL2); intron 1 C/T in the gene encoding Arginase 1 (Arg1); Leu 252 Val C/G in the gene encoding Insulin-like growth factor II receptor (IGF2R); and −1082 A/G in the gene encoding Interleukin 10 (IL-10), wherein the presence or absence of one or more of said polymorphisms is indicative of the subject's risk of developing lung cancer. The one or more polymorphisms can be detected directly or by detection of one or more polymorphisms which are in linkage disequilibrium with said one or more polymorphisms. Linkage disequilibrium (LD) is a phenomenon in genetics whereby two or more mutations or polymorphisms are in such close genetic proximity that they are co-inherited. This means that in genotyping, detection of one polymorphism as present implies the presence of the other. (Reich DE et al; Linkage disequilibrium in the human genome, Nature 2001, 411:199-204, herein incorporated by reference in its entirety.)

In some embodiments, the method can additionally include analyzing a sample from said subject for the presence of one or more further polymorphisms selected from the group consisting of: Arg 399 Gln G/A in the X-ray repair complementing defective in Chinese hamster 1 (XRCC1) gene; −251 A/T in the gene encoding Interleukin-8 (IL-8); A870G in the gene encoding Cyclin D (CCND1); −511 A/G in the gene encoding Interleukin 1B (IL-1B); −670G in the gene encoding FAS (Apo-1/CD95); −751 G/T in the promoter of the Xeroderma pigmentosum complementation group D (XPD) gene; Ile 462 Val A/G in the gene encoding Cytochrome P450 1A1 (CYP1A1); Ser 326 Cys G/C in the gene encoding 8-Oxoguanine DNA glycolase (OGG1); Arg 197 Gln A/G in the gene encoding N-acetyltransferase 2 (NAT2); 1019 G/C Pst I in the gene encoding Cytochrome P450 2E1 (CYP2E1); C/T Rsa I in the gene encoding Cytochrome P450 2E1; GSTM null in the gene encoding Glutathione S-transferase M (GSTM); −1607 1G/2G in the promoter of the gene encoding Matrix metalloproteinase 1 (MMP1); Gln 185 Glu G/C in the gene encoding Nibrin (NBS1); Phe 257 Ser C/T in the gene encoding REV1; and Asp 148 Glu G/T in the gene encoding Apex nuclease (APE1).

Again, detection of the one or more further polymorphisms can be carried out directly or by detection of polymorphisms in linkage disequilibrium with the one or more further polymorphisms.

In some embodiments, the presence of one or more polymorphisms selected from the group consisting of: the Asp 298 Glu TT genotype in the gene encoding NOS3; the Arg 312 Gln CG or GG genotype in the gene encoding SOD3; the Asn 357 Ser AG or GG genotype in the gene encoding MMP12; the 105 AC or CC genotype in the gene encoding IL-18; the −133 CG or GG genotype in the gene encoding IL-18; the −765 CC or CG genotype in the promoter of the gene encoding COX2; the −221 TT genotype in the gene encoding MUC5AC; the intron 1 C/T TT genotype in the gene encoding Arg1; the Leu252Val GG genotype in the gene encoding IGF2R; the −1082 GG genotype in the gene encoding IL-10; the −251 AA genotype in the gene encoding IL-8; the Arg 399 Gln AA genotype in the XRCC1 gene; the A870G GG genotype in the gene encoding CCND1; the −751 GG genotype in the promoter of the XPD gene; the Ile 462 Val AG or GG genotype in the gene encoding CYP1A1; the Ser 326 Cys GG genotype in the gene encoding OGG1; and the Phe 257 Ser CC genotype in the gene encoding REV1 can be indicative of a reduced risk of developing lung cancer.

In some embodiments, the presence of one or more polymorphisms selected from the group consisting of: the −786 TT genotype in the promoter of the gene encoding NOS3; the Ala 15 Thr GG genotype in the gene encoding ACT; the 105 AA genotype in the gene encoding IL-18; the −133 CC genotype in the promoter of the gene encoding IL-18; the 874 AA genotype in the gene encoding IFNγ; the −765 GG genotype in the promoter of the gene encoding COX2; the −447 CC or GC genotype in the gene encoding CTGF; the +161 AA or AG genotype in the gene encoding MBL2; the −511 GG genotype in the gene encoding IL-1B; the A-670G AA genotype in the gene encoding FAS; the Arg 197 Gln GG genotype in the gene encoding NAT2; the Ile462 Val AA genotype in the gene encoding CYP1A1; the 1019 G/C Pst I CC or CG genotype in the gene encoding CYP2E1; the C/T Rsa I TT or TC genotype in the gene encoding CYP2E1; the GSTM null genotype in the gene encoding GSTM; the −1607 2G/2G genotype in the promoter of the gene encoding MMP1; the Gln 185 Glu CC genotype in the gene encoding NBS1; and the Asp 148 Glu GG genotype in the gene encoding APE1, can be indicative of an increased risk of developing lung cancer.

In some embodiments, the methods of the invention are particularly useful in smokers (both current and former).

It will be appreciated that the methods of the invention identify two categories of polymorphisms—namely those associated with a reduced risk of developing lung cancer (which can be termed "protective polymorphisms") and those associated with an increased risk of developing lung cancer (which can be termed "susceptibility polymorphisms").

Therefore, in some embodiments, the present invention further provides a method of assessing a subject's risk of developing lung cancer, said method including: determining the presence or absence of at least one protective polymorphism associated with a reduced risk of developing lung cancer and in the absence of at least one protective polymorphism, determining the presence or absence of at least one susceptibility polymorphism associated with an increased risk of developing lung cancer. The presence of one or more of said protective polymorphisms is indicative of a reduced risk of developing lung cancer, and the absence of at least one protective polymorphism in combination with the presence of at least one susceptibility polymorphism is indicative of an increased risk of developing lung cancer.

In some embodiments, said at least one protective polymorphism is selected from the group consisting of: the Asp 298 Glu TT genotype in the gene encoding NOS3; the Arg 312 Gln CG or GG genotype in the gene encoding SOD3; the Asn 357 Ser AG or GG genotype in the gene encoding MMP12; the 105 AC or CC genotype in the gene encoding IL-18; the −133 CG or GG genotype in the gene encoding IL-18; the −765 CC or CG genotype in the promoter of the gene encoding COX2; the −221 TT genotype in the gene encoding MUC5AC; the intron 1 C/T TT genotype in the gene encoding Arg1; the Leu252Val GG genotype in the gene encoding IGF2R; the −1082 GG genotype in the gene encoding IL-10; the −251 AA genotype in the gene encoding IL-8; the Arg 399 Gln AA genotype in the XRCC1 gene; the A870G GG genotype in the gene encoding CCND1; the −751 GG genotype in the promoter of the XPD gene; the Ile 462 Val AG or GG genotype in the gene encoding CYP1A1; the Ser 326 Cys GG genotype in the gene encoding OGG1; and the Phe 257 Ser CC genotype in the gene encoding REV1.

In some embodiments, the at least one susceptibility polymorphism can be selected from the group consisting of: the −786 TT genotype in the promoter of the gene encoding NOS3; the Ala 15 Thr GG genotype in the gene encoding ACT; the 105 AA genotype in the gene encoding IL-18; the −133 CC genotype in the promoter of the gene encoding IL-18; the 874 AA genotype in the gene encoding IFNγ; the −765 GG genotype in the promoter of the gene encoding COX2; the −447 CC or GC genotype in the gene encoding CTGF; the +161 AA or AG genotype in the gene encoding MBL2; the −511 GG genotype in the gene encoding IL-1B; the A-670G AA genotype in the gene encoding FAS; the Arg 197 Gln GG genotype in the gene encoding NAT2; the Ile462 Val AA genotype in the gene encoding CYP1A1; the 1019 G/C Pst I CC or CG genotype in the gene encoding CYP2E1;

the C/T Rsa I TT or TC genotype in the gene encoding CYP2E1; the GSTM null genotype in the gene encoding GSTM; the −1607 2G/2G genotype in the promoter of the gene encoding MMP1; the Gln 185 Glu CC genotype in the gene encoding NBS1; and the Asp 148 Glu GG genotype in the gene encoding APE1.

In some embodiments of the invention, the presence of two or more protective polymorphisms is indicative of a reduced risk of developing lung cancer.

In a further preferred form of some embodiments of the invention, the presence of two or more susceptibility polymorphisms is indicative of an increased risk of developing lung cancer. In still a further preferred form of the invention the presence of two or more protective polymorphims irrespective of the presence of one or more susceptibility polymorphisms is indicative of reduced risk of developing lung cancer.

In another aspect, the invention provides a method of determining a subject's risk of developing lung cancer, said method including obtaining the result of one or more genetic tests of a sample from said subject, and analyzing the result for the presence or absence of one or more polymorphisms selected from the group consisting of: Asp 298 Glu in the gene encoding Nitric oxide synthase 3 (NOS3); −786 T/C in the promoter of the gene encoding NOS3; Arg 312 Gln in the gene encoding Superoxide dismutase 3 (SOD3); Ala 15 Thr in the gene encoding Anti-chymotrypsin (ACT); Asn 357 Ser A/G in the gene encoding Matrix metalloproteinase 12 (MMP12); 105 A/C in the gene encoding Interleukin-18 (IL-18); −133 G/C in the promoter of the gene encoding Interleukin-18; 874 A/T in the gene encoding Interferon gamma (IFNγ); −765 G/C in the gene encoding Cyclooxygenase 2 (COX2); −447 G/C in the gene encoding Connective tissue growth factor (CTGF); −221 C/T in the gene encoding Mucin 5AC (MUC5AC); +161 G/A in the gene encoding Mannose binding lectin 2 (MBL2); intron 1 C/T in the gene encoding Arginase 1 (Arg1); Leu 252 Val C/G in the gene encoding Insulin-like growth factor II receptor (IGF2R); −1082 A/G in the gene encoding Interleukin 10 (IL-10); and one or more polymorphisms in linkage disequilibrium with any one or more of these polymorphisms. A result indicating the presence or absence of one or more of said polymorphisms is indicative of the subject's risk of developing lung cancer.

In a further aspect there is provided a method of determining a subject's risk of developing lung cancer including the analysis of two or more polymorphisms selected from the group consisting of: Asp 298 Glu in the gene encoding NOS3; −786 T/C in the promoter of the gene encoding NOS3; Arg 312 Gln in the gene encoding SOD3; −251 A/T in the gene encoding IL-8; Ala 15 Thr in the gene encoding ACT; Asn 357 Ser A/G in the gene encoding MMP12; 105 A/C in the gene encoding IL-18; −133 G/C in the promoter of the gene encoding IL-18; 874 A/T in the gene encoding IFNγ; Arg 399 Gln G/A in the XRCC1 gene; A870G in the gene encoding CCND1; −511 A/G in the gene encoding IL-1B; −670G in the gene encoding FAS (Apo-1/CD95); −751 G/T in the promoter of the XPD gene; Ile 462 Val A/G in the gene encoding CYP1A1; Ser 326 Cys G/C in the gene encoding OGG1; Arg 197 Gln A/G in the gene encoding NAT2; 1019 G/C Pst I in the gene encoding CYP2E1; C/T Rsa I in the gene encoding CYP2E1; GSTM null in the gene encoding GSTM; −765 C/G in the promoter of the gene encoding COX2; −1607 1G/2G in the promoter of the gene encoding MMP1; −447 G/C in the gene encoding CTGF; −221 C/T in the gene encoding MUC5AC; +161 G/A in the gene encoding MBL2; intron 1 C/T in the gene encoding Arg1; Leu 252 Val C/G in the gene encoding IGF2R; −1082 A/G in the gene encoding IL-10; Gln 185 Glu G/C in the gene encoding NBS1; Phe 257 Ser C/T in the gene encoding REV1; Asp 148 Glu G/T in the gene encoding APE1; and one or more polymorphisms in linkage disequilibrium with any one or more of these polymorphisms.

In various embodiments, any one or more of the above methods includes the step of analyzing the amino acid present at a position mapping to codon 298 of the gene encoding NOS3.

In some embodiments, the presence of glutamate at said position is indicative of an increased risk of developing lung cancer.

In some embodiments, the presence of asparagine at said position is indicative of reduced risk of developing lung cancer.

In various embodiments, any one or more of the above methods includes the step of analyzing the amino acid present at a position mapping to codon 312 in the gene encoding SOD3.

In various embodiments, any one or more of the above methods includes the step of analyzing the amino acid present at a position mapping to codon 15 in the gene encoding ACT.

In various embodiments, any one or more of the above methods includes the step of analyzing the amino acid present at a position mapping to codon 357 in the gene encoding MMP12.

In various embodiments, any one or more of the above methods includes the step of analyzing the amino acid present at a position mapping to codon 399 in the XRCC1 gene.

In various embodiments, any one or more of the above methods includes the step of analyzing the amino acid present at a position mapping to codon 462 in the gene encoding CYP1A1.

In various embodiments, any one or more of the above methods includes the step of analyzing the amino acid present at a position mapping to codon 326 in the gene encoding OGG1.

In various embodiments, any one or more of the above methods includes the step of analyzing the amino acid present at a position mapping to codon 197 in the gene encoding NAT2.

In various embodiments, any one or more of the above methods includes the step of analyzing the amino acid present at a position mapping to codon 185 in the gene encoding NBS1.

In some embodiments, the presence of glutamine at said position is indicative of an increased risk of developing lung cancer.

In various embodiments, any one or more of the above methods includes the step of analyzing the amino acid present at a position mapping to codon 257 in the gene encoding REV1.

In some embodiments, the presence of serine at said position is indicative of reduced risk of developing lung cancer.

In various embodiments, any one or more of the above methods includes the step of analyzing the amino acid present at a position mapping to codon 252 in the gene encoding IGF2R.

In some embodiments, the presence of valine at said position is indicative of reduced risk of developing lung cancer.

In various embodiments, any one or more of the above methods includes the step of analyzing the amino acid present at a position mapping to codon 148 in the, gene encoding APE1.

In some embodiments, the presence of glutamate at said position is indicative of an increased risk of developing lung cancer.

In a preferred form of the invention the methods as described herein are performed in conjunction with an analysis of one or more risk factors, including one or more epidemiological risk factors, associated with a risk of developing lung cancer. Such epidemiological risk factors include but are not limited to smoking or exposure to tobacco smoke, age, sex, and familial history of lung cancer.

In a further aspect, the invention provides for the use of at least one polymorphism in the assessment of a subject's risk of developing lung cancer, wherein said at least one polymorphism is selected from the group consisting of: Asp 298 Glu in the gene encoding Nitric oxide synthase 3 (NOS3); −786 T/C in the promoter of the gene encoding NOS3; Arg 312 Gln in the gene encoding Superoxide dismutase 3 (SOD3); Ala 15 Thr in the gene encoding Anti-chymotrypsin (ACT); Asn 357 Ser A/G in the gene encoding Matrix metalloproteinase 12 (MMP12); 105 A/C in the gene encoding Interleukin-18 (IL-18); −133 G/C in the promoter of the gene encoding Interleukin-18; 874 A/T in the gene encoding Interferon gamma (IFNγ); −765 G/C in the gene encoding Cyclooxygenase 2 (COX2); −447 G/C in the gene encoding Connective tissue growth factor (CTGF); −221 C/T in the gene encoding Mucin 5AC (MUC5AC); +161 G/A in the gene encoding Mannose binding lectin 2 (MBL2); intron 1 C/T in the gene encoding Arginase 1 (Arg1); Leu 252 Val C/G in the gene encoding Insulin-like growth factor II receptor (IGF2R); −1082 A/G in the gene encoding Interleukin 10 (IL-10); and one or more polymorphisms in linkage disequilibrium with any one of said polymorphisms.

Optionally, said use can be in conjunction with the use of at least one further polymorphism selected from the group consisting of: Arg 399 Gln G/A in the X-ray repair complementing defective in Chinese hamster 1 (XRCC1) gene; −251 A/T in the gene encoding Interleukin-8 (IL-8); A870G in the gene encoding Cyclin D (CCND1); −511 A/G in the gene encoding Interleukin 1B (IL-1B); −670G in the gene encoding FAS (Apo-1/CD95); −751 G/T in the promoter of the Xeroderma pigmentosum complementation group D (XPD) gene; Ile 462 Val A/G in the gene encoding Cytochrome P450 1A1 (CYP1A1); Ser 326 Cys G/C in the gene encoding 8-Oxoguanine DNA glycolase (OGG1); Arg 197 Gln A/G in the gene encoding N-acetyltransferase 2 (NAT2); 1019 G/C Pst I in the gene encoding Cytochrome P450 2E1 (CYP2E1); C/T Rsa I in the gene encoding Cytochrome P450 2E1; GSTM null in the gene encoding Glutathione S-transferase M (GSTM); −1607 1G/2G in the promoter of the gene encoding Matrix metalloproteinase 1 (MMP1); Gln 185 Glu G/C in the gene encoding Nibrin (NBS1); Phe 257 Ser C/T in the gene encoding REV1; Asp 148 Glu G/T in the gene encoding Apex nuclease (APE1); and one or more polymorphisms which are in linkage disequilibrium with any one or more of these polymorphisms.

In another aspect, the invention provides a set of nucleotide probes and/or primers for use in the preferred methods of the invention herein described. Preferably, the nucleotide probes and/or primers are those which span, or are able to be used to span, the polymorphic regions of the genes. Also provided are one or more nucleotide probes and/or primers including the sequence of any one of the probes and/or primers herein described, including any one including the sequence of any one of SEQ.ID. NO. 1 to 145, more preferably any one of SEQ.ID.NO. 3 to 142.

In yet a further aspect, the invention provides a nucleic acid microarray for use in the methods of the invention, which microarray includes a substrate presenting nucleic acid sequences capable of hybridizing to nucleic acid sequences which encode one or more of the susceptibility or protective polymorphisms described herein or sequences complimentary thereto.

In another aspect, the invention provides an antibody microarray for use in the methods of the invention, which microarray includes a substrate presenting antibodies capable of binding to a product of expression of a gene the expression of which is upregulated or downregulated when associated with a susceptibility or protective polymorphism as described herein.

In a further aspect, the present invention provides a method treating a subject having an increased risk of developing lung cancer including the step of replicating, genotypically or phenotypically, the presence and/or functional effect of a protective polymorphism in said subject.

In yet a further aspect, the present invention provides a method of treating a subject having an increased risk of developing lung cancer, said subject having a detectable susceptibility polymorphism which either upregulates or downregulates expression of a gene such that the physiologically active concentration of the expressed gene product is outside a range which is normal for the age and sex of the subject, said method including the step of restoring the physiologically active concentration of said product of gene expression to be within a range which is normal for the age and sex of the subject.

In a further aspect, the present invention provides a method of treating a subject having an increased risk of developing lung cancer and for whom the presence of the AA genotype at the 105 C/A polymorphism in the gene encoding IL-18 has been determined, said method including administering to said subject an agent capable of augmenting IL-18 activity in said subject.

In yet a further aspect, the present invention provides a method of treating a subject having an increased risk of developing lung cancer and for whom the presence of the CC genotype at the −133 G/C polymorphism in the promoter of the gene encoding IL-18 has been determined, said method including administering to said subject an agent capable of augmenting IL-18 activity in said subject.

In yet a further aspect, the present invention provides a method for screening for compounds that modulate the expression and/or activity of a gene, the expression of which is upregulated or downregulated when associated with a susceptibility or protective polymorphism, said method including the steps of: contacting a candidate compound with a cell including a susceptibility or protective polymorphism which has been determined to be associated with the upregulation or downregulation of expression of a gene, and measuring the expression of said gene following contact with said candidate compound. A change in the level of expression after the contacting step as compared to before the contacting step is indicative of the ability of the compound to modulate the expression and/or activity of said gene. Preferably, the cell is a human lung cell which has been pre-screened to confirm the presence of said polymorphism. Preferably, said cell includes a susceptibility polymorphism associated with upregulation of expression of said gene and said screening is for candidate compounds which downregulate expression of said gene. Alternatively, said cell includes a susceptibility polymorphism associated with downregulation of expression of said gene and said screening is for candidate compounds which upregulate expression of said gene.

In another embodiment, said cell includes a protective polymorphism associated with upregulation of expression of said gene and said screening is for candidate compounds which further upregulate expression of said gene. Alternatively, said cell includes a protective polymorphism associated with downregulation of expression of said gene and said screening is for candidate compounds which further downregulate expression of said gene.

In another aspect, the present invention provides a method for screening for compounds that modulate the expression and/or activity of a gene, the expression of which is upregulated or downregulated when associated with a susceptibility or protective polymorphism, said method includes the steps of: contacting a candidate compound with a cell including a gene, the expression of which is upregulated or downregulated when associated with a susceptibility or protective polymorphism but which in said cell the expression of which is neither upregulated nor downregulated; and measuring the expression of said gene following contact with said candidate compound. A change in the level of expression after the contacting step as compared to before the contacting step is indicative of the ability of the compound to modulate the expression and/or activity of said gene. Preferably, expression of the gene is downregulated when associated with a susceptibility polymorphism once said screening is for candidate compounds which in said cell, upregulate expression of said gene. Preferably, said cell is a human lung cell which has been pre-screened to confirm the presence, and baseline level of expression, of said gene. Alternatively, expression of the gene is upregulated when associated with a susceptibility polymorphism and said screening is for candidate compounds which, in said cell, downregulate expression of said gene.

In another embodiment, expression of the gene is upregulated when associated with a protective polymorphism and said screening is for compounds which, in said cell, upregulate expression of said gene. Alternatively, expression of the gene is downregulated when associated with a protective polymorphism and said screening is for compounds which, in said cell, downregulate expression of said gene.

In yet a further aspect, the present invention provides a method of assessing the likely responsiveness of a subject at risk of developing or suffering from lung cancer to a prophylactic or therapeutic treatment, which treatment involves restoring the physiologically active concentration of a product of gene expression to be within a range which is normal for the age and sex of the subject, which method includes detecting in said subject the presence or absence of a susceptibility polymorphism which when present either upregulates or downregulates expression of said gene such that the physiological active concentration of the expressed gene product is outside said normal range, wherein the detection of the presence of said polymorphism is indicative of the subject likely responding to said treatment.

In still a further aspect the present invention provides a method of treating a subject having an increased risk of developing lung cancer and for whom the presence of the GG genotype at the −765 C/G polymorphism present in the promoter of the gene encoding COX2 has been determined. The method includes administering to said subject an agent capable of reducing COX2 activity in said subject. In one embodiment, the agent is a COX2 inhibitor or a nonsteroidal anti-inflammatory drug (NSAID), preferably the COX2 inhibitor is selected from the group consisting of Celebrex™ (Celecoxib), Bextra™ (Valdecoxib), and Vioxx™ (Rofecoxib).

In yet still a further aspect the present invention provides a method of treating a subject having an increased risk of developing lung cancer and for whom the presence of the 2G2G genotype at the −1607 1G/2G polymorphism in the promoter of the gene encoding MMP1 has been determined, said method including administering to the subject an agent capable of reducing MMP1 activity in the subject.

In one embodiment, the agent is an agent capable of increasing expression of or the activity of one or more tissue inhibitors of metalloproteinases (TIMPs), preferably the expression or activity of one or more of TIMP1, TIMP2, TIMP3, or TIMP4. In a further embodiment, said agent is an agent capable of reducing expression of or the activity of one or more membrane bound MMPs. In still a futher embodiment, said agent is a MMP inhibitor, preferably the MMP inhibitor is selected from the group including 4,5-dihydroxy-anthaquinone-2-carboxylic acid (AQCA), anthraquinyl-mer-captoethyamine, anthraquinyl-alanine hydroxamate, and derivatives thereof.

In a further aspect, the present invention provides a kit for assessing a subject's risk of developing lung cancer, said kit including a means of analyzing a sample from said subject for the presence or absence of one or more polymorphisms disclosed herein.

DETAILED DESCRIPTION OF THE PREFERRED EMBODIMENT

Figure 1:
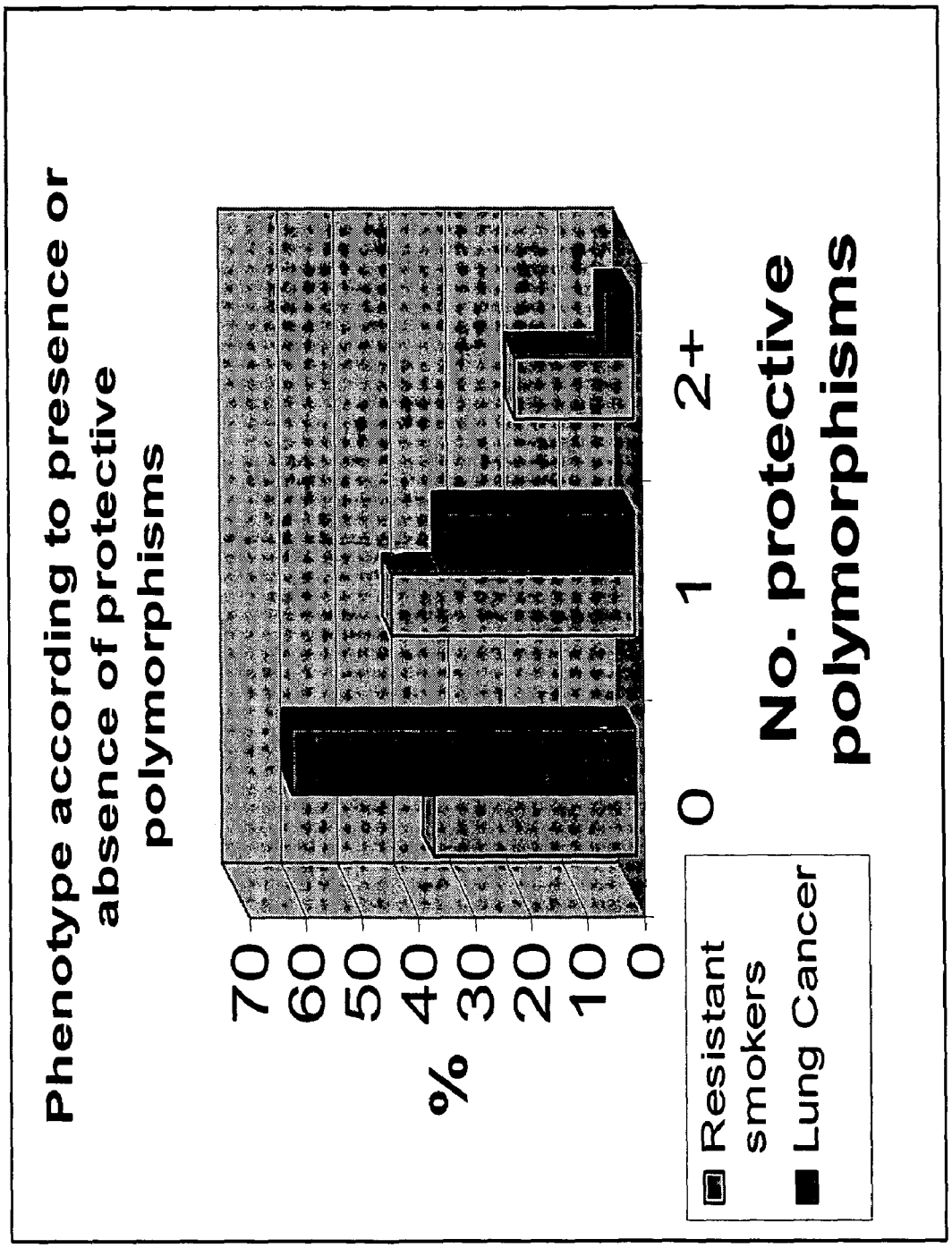
FIG. 1 depicts a graph showing the percentage of people with lung cancer plotted against the number of protective polymorphisms.
Figure 2:
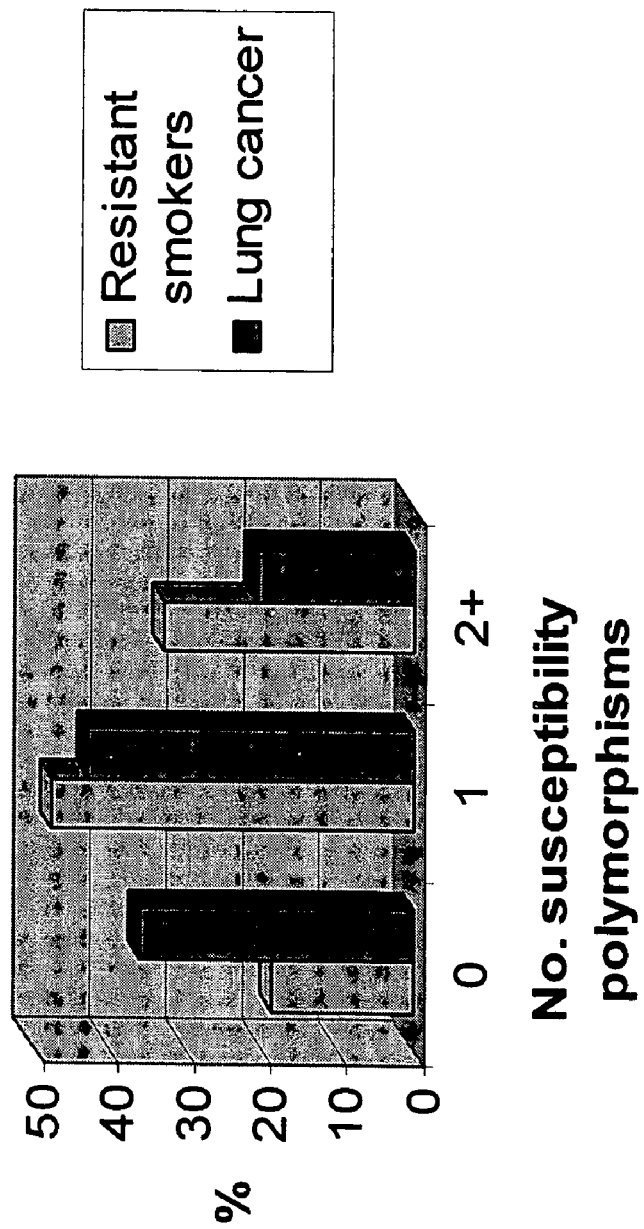
FIG. 2 depicts a graph showing the percentage of people with lung cancer plotted against the number of susceptibility polymorphisms.
Figure 3:
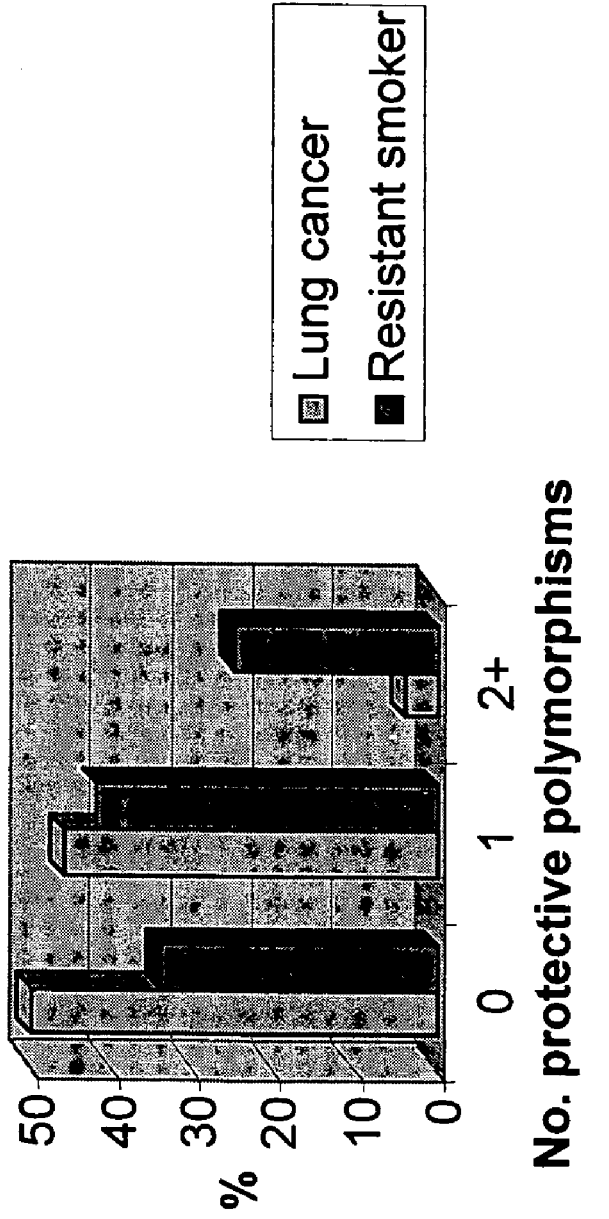
FIG. 3 depicts a graph showing the frequency of protective polymorphisms in smokers with lung cancer and in resistant smokers.
Figure 4:
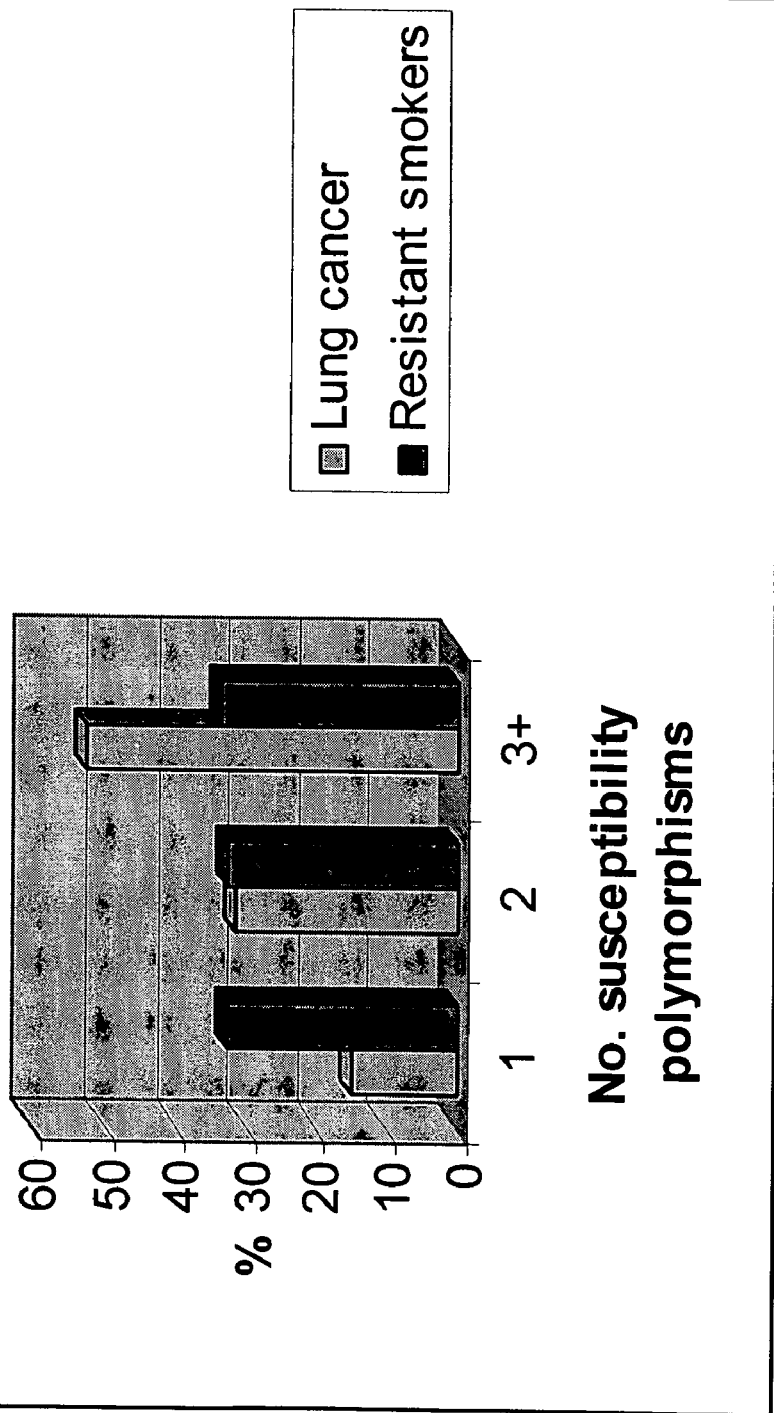
FIG. 4 depicts a graph showing the frequency of susceptibility polymorphisms in smokers with lung cancer and in resistant smokers.

Additional biomarkers which can be used to assess a subject's risk of developing pulmonary disorders such as lung cancer, or a risk of developing lung cancer-related impaired lung function, can be desireable, particularly if the subject is a smoker. In some aspects, it is primarily to such biomarkers and their use in methods to assess risk of developing such disorders that the present invention is directed.

Using case-control studies the frequencies of several genetic variants (polymorphisms) of candidate genes in smokers who have developed lung cancer and blood donor controls have been compared. The majority of these candidate genes have confirmed (or likely) functional effects on gene expression or protein function. Specifically the frequencies of polymorphisms between blood donor controls, resistant smokers and those with lung cancer (subdivided into those with early onset and those with normal onset) have been compared. The present invention demonstrates that there are both protective and susceptibility polymorphisms present in selected candidate genes of the patients tested.

In one embodiment described herein 19 susceptibility genetic polymorphisms and 17 protective genetic polymorphisms are identified. These are as follows in Table 1A:

TABLE 1A

| Gene | Polymorphism | Role |
| --- | --- | --- |
| Nitric Oxide synthase 3 (NOS3) | NOS3 Asp 298 Glu | TT protective |
| Nitric Oxide synthase 3 (NOS3) | NOS3 −786 T/C | TT susceptibility |
| Superoxide dismutase 3 (SOD3) | SOD3 Arg 312 Gln | CG/GG protective |
| XRCC1 | XRCC1 Arg 399 Gln G/A | AA protective |
| Interleukin-8 (IL-8) | IL-8 −251 A/T | AA protective |
| Anti-chymotrypsin (ACT) | ACT Ala 15 Thr | GG susceptibility |
| Cyclin D (CCND1) | CCND1 A870G | GG protective<br>AA susceptibility |
| Interleukin 1B (IL-1B) | IL-1B −511 A/G | GG susceptibility |
| FAS (Apo-1/CD95) | FAS A-670G | AA susceptibility |
| XPD | XPD −751 G/T | GG protective |
| CYP 1A1 | CYP 1A1 Ile 462 Val A/G | GG/AG protective<br>AA susceptibility |
| Matrix metalloproteinase 12 (MMP12) | MMP12 Asn 357 Ser A/G | GG/AG protective |
| 8-Oxoguanine DNA glycolase (OGG1) | OGG1 Ser 326 Cys G/C | GG protective |
| N-acetyltransferase 2 (NAT2) | NAT2 Arg 197 Gln A/G | GG susceptibility |
| CYP2E1 | CYP2E1 1019 G/C Pst I | CC/CG susceptibility |
| CYP2E1 | GYP2E1 C/T Rsa I | TT/TC susceptibility |
| Interleukin-18 (IL-18) | IL-18 105 A/C | AC/CC protective<br>AA susceptibility |
| Interleukin-18 (IL-18) | IL-18 −133 G/C | CG/GG protective<br>CC susceptibility |
| Glutathione S-transferase M | GSTM null | Null susceptibility |
| Interferon gamma (IFNγ) | IFNγ 874 A/T | AA susceptibility |
| Cyclooxygenase 2 (COX2) | COX2 −765 C/G | CC/CG protective<br>GG susceptibility |
| Matrix metalloproteinase 1 (MMP1) | MMP1 −1607 1G/2G | 2G susceptibility |
| Connective tissue growth factor (CTGF) | CTGF −447 G/C | CG/CC susceptibility |
| Mucin 5AC (MUC5AC) | MUC5AC −221 C/T | TT protective |
| Mannose binding lectin 2 (MBL2) | MBL2 +161 G/A | AG/AA susceptibility |
| Nibrin (NBS1) | NBS1 Gln185Glu G/C | CC susceptibility |
| Arginase 1 (Arg1) | Arg1 intron 1 C/T | TT protective |
| REV1 | REV1 Phe257Ser C/T | CC protective |
| Insulin-like growth factor II receptor (IGF2R) | IGF2R Leu252Val C/G | GG protective |
| Apex nuclease (Apex or APE1)) | Apex Asp148Glu G/T | GG susceptibility |
| Interleukin 10 (IL-10) | IL-10 −1082 A/G | GG protective |

A susceptibility genetic polymorphism is one which, when present, is indicative of an increased risk of developing lung cancer. In contrast, a protective genetic polymorphism is one which, when present, is indicative of a reduced risk of developing lung cancer.

As used herein, the phrase "risk of developing lung cancer" means the likelihood that a subject to whom the risk applies will develop lung cancer, and includes predisposition to, and potential onset of the disease. Accordingly, the phrase "increased risk of developing lung cancer" means that a subject having such an increased risk possesses an hereditary inclination or tendency to develop lung cancer. This does not mean that such a person will actually develop lung cancer at any time, merely that he or she has a greater likelihood of developing lung cancer compared to the general population of individuals that either does not possess a polymorphism associated with increased lung cancer or does possess a polymorphism associated with decreased lung cancer risk. Subjects with an increased risk of developing lung cancer include those with a predisposition to lung cancer, such as a tendency or predilection regardless of their lung function at the time of assessment, for example, a subject who is genetically inclined to lung cancer but who has normal lung function, those at potential risk, including subjects with a tendency to mildly reduced lung function who are likely to go on to suffer lung cancer if they keep smoking, and subjects with potential onset of lung cancer, who have a tendency to poor lung function on spirometry etc., consistent with lung cancer at the time of assessment.

Similarly, the phrase "decreased risk of developing lung cancer" means that a subject having such a decreased risk possesses an hereditary disinclination or reduced tendency to develop lung cancer. This does not mean that such a person will not develop lung cancer at any time, merely that he or she has a decreased likelihood of developing lung cancer compared to the general population of individuals that either does possess one or more polymorphisms associated with increased lung cancer, or does not possess a polymorphism associated with decreased lung cancer.

It will be understood that in the context of the present invention the term "polymorphism" means the occurrence together in the same population at a rate greater than that attributable to random mutation (usually greater than 1%) of two or more alternate forms (such as alleles or genetic markers) of a chromosomal locus that differ in nucleotide sequence or have variable numbers of repeated nucleotide units. See www "dot" ornl "dot" gov/sci/techresources/Human_Genome/publicat/97pr/09gloss "dot" html#p. Accordingly, the term "polymorphisms" is used herein contemplates genetic variations, including single nucleotide substitutions, insertions and deletions of nucleotides, repetitive sequences (such as microsatellites), and the total or partial absence of genes (eg. null mutations). As used herein, the term "polymorphisms" also includes genotypes and haplotypes. A genotype is the genetic composition at a specific locus or set of loci. A haplotype is a set of closely linked genetic markers present on one chromosome which are not easily separable by recombination, tend to be inherited together, and can be in linkage disequilibrium. A haplotype can be identified by patterns of polymorphisms such as SNPs. Similarly, in some embodiments, the term "single nucleotide polymorphism" or "SNP" in the context of the present invention includes single base nucleotide subsitutions and short deletion and insertion polymorphisms. In other embodiments, the terms only refer to single base nucleotide substitutions, deletions, and insertions.

A reduced or increased risk of a subject developing lung cancer can be diagnosed by analyzing a sample from said subject for the presence of a polymorphism selected from the group consisting of: Asp 298 Glu in the gene encoding Nitric oxide synthase 3 (NOS3); −786 T/C in the promoter of the gene encoding NOS3; Arg 312 Gln in the gene encoding Superoxide dismutase 3 (SOD3); Ala 15 Thr in the gene encoding Anti-chymotrypsin (ACT); Asn 357 Ser A/G in the gene encoding Matrix metalloproteinase 12 (MMP12); 105 A/C in the gene encoding Interleukin-18 (IL-18); −133 G/C in the promoter of the gene encoding Interleukin-18; 874 A/T in the gene encoding Interferon gamma (IFNγ); −765 G/C in the gene encoding Cyclooxygenase 2 (COX2); −447 G/C in the gene encoding Connective tissue growth factor (CTGF); −221 C/T in the gene encoding Mucin 5AC (MUC5AC); +161 G/A in the gene encoding Mannose binding lectin 2 (MBL2); intron 1 C/T in the gene encoding Arginase 1 (Arg1); Leu 252 Val C/G in the gene encoding Insulin-like growth factor II receptor (IGF2R); and −1082 A/G in the gene encoding Interleukin 10 (IL-10), or one or more polymorphisms which are in linkage disequilibrium with any one or more of the above group.

These polymorphisms can also be analysed in combinations of two or more, or in combination with other polymorphisms indicative of a subject's risk of developing lung cancer inclusive of the remaining polymorphisms listed above.

Expressly contemplated are combinations of the above polymorphisms with polymorphisms as described in PCT International application PCT/NZ02/00106, published as WO 02/099134 (herein incorporated by reference in its entirety).

Assays which involve combinations of polymorphisms, including those amenable to high throughput, such as those utilising microarrays, are preferred.

Statistical analyses, particularly of the combined effects of these polymorphisms, show that the genetic analyses of the present invention can be used to determine the risk quotient of any smoker and in particular to identify smokers at greater risk of developing lung cancer. Such combined analysis can be of combinations of susceptibility polymorphisms only, of protective polymorphisms only, or of combinations of both. Analysis can also be step-wise, with analysis of the presence or absence of protective polymorphisms occurring first and then with analysis of susceptibility polymorphisms proceeding only where no protective polymorphisms are present.

Thus, through systematic analysis of the frequency of these polymorphisms in well defined groups of smokers and non-smokers, as described herein, it is possible to implicate certain proteins in the development of lung cancer and improve the ability to identify which smokers are at increased risk of developing lung cancer-related impaired lung function and lung cancer for predictive purposes.

The present results show for the first time that the minority of smokers who develop lung cancer do so because they have one or more of the susceptibility polymorphisms and few or none of the protective polymorphisms defined herein. It is thought that the presence of one or more suscetptible polymorphisms, together with the damaging irritant and oxidant effects of smoking, combine to make this group of smokers highly susceptible to developing lung cancer. Additional risk factors, such as familial history, age, weight, pack years, etc., will also have an impact on the risk profile of a subject, and can be assessed in combination with the genetic analyses described herein.

The one or more polymorphisms can be detected directly or by detection of one or more polymorphisms which are in linkage disequilibrium with said one or more polymorphisms. As discussed above, linkage disequilibrium is a phenomenon in genetics whereby two or more mutations or polymorphisms are in such close genetic proximity that they are co-inherited. This means that in genotyping, detection of one polymorphism as present implies the presence of the other. (Reich D E et al; Linkage disequilibrium in the human genome, Nature 2001, 411:199-204, herein incorporated by reference in its entirety.)

Examples of polymorphisms described herein that have been reported to be in linkage disequilibrium are presented herein, and include the Interleukin-18 −133 C/G and 105 A/C polymorphisms, and the CYP2E1, 1019 G/C PstI and C/T RsaI polymorphisms, as shown below in Table 1B.

TABLE 1B

| Gene | SNPs | rs numbers | Alleles in LD | LD between alleles | Phenotype in lung cancer |
| --- | --- | --- | --- | --- | --- |
| Interleukin-18 | IL18 −133 C/G | rs360721 | C allele | Strong LD | CC susceptibility |
|  | IL18 105 A/C | rs549908 | A allele |  | AA susceptibility |
| CYP2E1 | CYP2E1 1019 G/C PstI | rs3813867 | C allele | Strong LD | CG susceptibility |
|  | CYP2E1 C/T RsaI | rs2031920 | T allele |  | TC susceptibility |

It will be apparent that polymorphsisms in linkage disequilibrium with one or more other polymorphism associated with increased or decreased risk of developing lung cancer will also provide utility as biomarkers for risk of developing lung cancer. The data presented herein shows that the frequency for SNPs in linkage disequilibrium is very similar. Accordingly, these genetically linked SNPs can be utilized in combined polymorphism analyses to derive a level of risk comparable to that calculated from the original SNP.

It will therefore be apparent that one or more polymorphisms in linkage disequilibrium with the polymorphisms specified herein can be identified, for example, using public data bases. Examples of such polymorphisms reported to be in linkage disequilibrium with the polymorphisms specified herein are presented herein in Table 36.

It will also be apparent that frequently a variety of nomenclatures may exist for any given polymorphism. For example, the polymorphism referred to herein as Arg 312 Gln in the gene encoding SOD3 is believed to have been referred to variously as Arg 213 Gly, +760 G/C, and Arg 231 Gly (rs1799895). When referring to a susceptibility or protective polymorphism as herein described, such alternative nomenclatures are also contemplated by the present invention.

The methods of the invention are primarily directed to the detection and identification of the above polymorphisms associated with lung cancer, which are all single nucleotide polymorphisms. In general terms, a single nucleotide polymorphism (SNP) is a single base change or point mutation resulting in genetic variation between individuals. SNPs occur in the human genome approximately once every 100 to 300 bases, and can occur in coding or non-coding regions. Due to the redundancy of the genetic code, a SNP in the coding region may or may not change the amino acid sequence of a protein product. A SNP in a non-coding region can, for example, alter gene expression by, for example, modifying control regions such as promoters, transcription factor binding sites, processing sites, ribosomal binding sites, and affect gene transcription, processing, and translation.

SNPs can facilitate large-scale association genetics studies, and there has recently been great interest in SNP discovery and detection. SNPs show great promise as markers for a number of phenotypic traits (including latent traits), such as for example, disease propensity and severity, wellness propensity, and drug responsiveness including, for example, susceptibility to adverse drug reactions. Knowledge of the association of a particular SNP with a phenotypic trait, coupled with the knowledge of whether an individual has said particular SNP, can enable the targeting of diagnostic, preventative and therapeutic applications to allow better disease management, to enhance understanding of disease states and to ultimately facilitate the discovery of more effective treatments, such as personalised treatment regimens;

Indeed, a number of databases have been constructed of known SNPs, and for some such SNPs, the biological effect associated with a SNP. For example, the NCBI SNP database "dbSNP" is incorporated into NCBI's Entrez system and can be queried using the same approach as the other Entrez databases such as PubMed and GenBank. This database has records for over 1.5 million SNPs mapped onto the human genome sequence. Each dbSNP entry includes the sequence context of the polymorphism (i.e., the surrounding sequence), the occurrence frequency of the polymorphism (by population or individual), and the experimental method(s), protocols, and conditions used to assay the variation, and can include information associating a SNP with a particular phenotypic trait.

At least in part because of the potential impact on health and wellness, there has been and continues to be a great deal of effort to develop methods that reliably and rapidly identify SNPs. This is no trivial task, at least in part because of the complexity of human genomic DNA, with a haploid genome of $3 \times 10^9$ base pairs, and the associated sensitivity and discriminatory requirements.

Genotyping approaches to detect SNPs well-known in the art include DNA sequencing, methods that require allele specific hybridization of primers or probes, allele specific incorporation of nucleotides to primers bound close to or adjacent to the polymorphisms (often referred to as "single base extension", or "minisequencing"), allele-specific ligation (joining) of oligonucleotides (ligation chain reaction or ligation padlock probes), allele-specific cleavage of oligonucleotides or PCR products by restriction enzymes (restriction fragment length polymorphisms analysis or RFLP) or chemical or other agents, resolution of allele-dependent differences in electrophoretic or chromatographic mobilities, by structure specific enzymes including invasive structure specific enzymes, or mass spectrometry. Analysis of amino acid variation is also possible where the SNP lies in a coding region and results in an amino acid change.

DNA sequencing allows the direct determination and identification of SNPs. The benefits in specificity and accuracy are generally outweighed for screening purposes by the difficulties inherent in whole genome, or even targeted subgenome, sequencing.

Mini-sequencing involves allowing a primer to hybridize to the DNA sequence adjacent to the SNP site on the test sample under investigation. The primer is extended by one nucleotide using all four differentially tagged fluorescent dideoxynucleotides (A,C,G, or T), and a DNA polymerase. Only one of the four nucleotides (homozygous case) or two of the four nucleotides (heterozygous case) is incorporated. The base that is incorporated is complementary to the nucleotide at the SNP position.

A number of methods currently used for SNP detection involve site-specific and/or allele-specific hybridisation (Matsuzaki, H. et al. *Genome Res.* 14:414-425 (2004); Matsuzaki, H. et al. *Nat. Methods* 1:109-111 (2004); Sethi, A. A. et al. *Clin. Chem.* 50(2):443-446 (2004), each of the foregoing which is herein incorporated by reference in its entirety). These methods are largely reliant on the discriminatory binding of oligonucleotides to target sequences containing the SNP of interest. The techniques of Affymetrix (Santa Clara, Calif.) and Nanogen Inc. (San Diego, Calif.) are particularly well-known, and utilize the fact that DNA duplexes containing single base mismatches are much less stable than duplexes that are perfectly base-paired. The presence of a matched duplex is detected by fluorescence.

The majority of methods to detect or identify SNPs by site-specific hybridisation require target amplification by methods such as PCR to increase sensitivity and specificity (see, for example U.S. Pat. No. 5,679,524, PCT publication WO 98/59066, PCT publication WO 95/12607, each of the foregoing which is herein incorporated by reference in its entirety). US Application 20050059030 (herein incorporated by reference in its entirety) describes a method for detecting a single nucleotide polymorphism in total human DNA without prior amplification or complexity reduction to selectively enrich for the target sequence, and without the aid of any enzymatic reaction. The method utilises a single-step hybridization involving two hybridization events: hybridization of a first portion of the target sequence to a capture probe, and hybridization of a second portion of said target sequence to a detection probe. Both hybridization events happen in the same reaction, and the order in which hybridisation occurs is not critical.

US Application 20050042608 (herein incorporated by reference in its entirety) describes a modification of the method of electrochemical detection of nucleic acid hybridization of Thorp et al. (U.S. Pat. No. 5,871,918, herein incorporated by reference in its entirety). Briefly, capture probes are designed, each of which has a different SNP base and a sequence of probe bases on each side of the SNP base. The probe bases are complementary to the corresponding target sequence adjacent to the SNP site. Each capture probe is immobilized on a different electrode having a non-conductive outer layer on a conductive working surface of a substrate. The extent of hybridization between each capture probe and the nucleic acid target is detected by detecting the oxidation-reduction reaction at each electrode, utilizing a transition metal complex. These differences in the oxidation rates at the different electrodes are used to determine whether the selected nucleic acid target has a single nucleotide polymorphism at the selected SNP site.

The technique of Lynx Therapeutics (Hayward, Calif.) using MEGATYPE™ technology can genotype very large numbers of SNPs simultaneously from small or large pools of genomic material. This technology uses fluorescently labeled probes and compares the collected genomes of two populations, enabling detection and recovery of DNA fragments spanning SNPs that distinguish the two populations, without requiring prior SNP mapping or knowledge.

A number of other methods for detecting and identifying SNPs exist. These include the use of mass spectrometry, for example, to measure probes that hybridize to the SNP (Ross, P. L. et al. Discrimination of single-nucleotide polymorphisms in human DNA using peptide nucleic acid probes detected by MALDI-TOF mass spectrometry. *Anal. Chem.* 69, 4197-4202 (1997), herein incorporated by reference in its entirety). This technique varies in how rapidly it can be performed, from a few samples per day to a high throughput of 40,000 SNPs per day, using mass code tags. A preferred example is the use of mass spectrometric determination of a nucleic acid sequence which includes the polymorphisms of the invention, for example, which includes the promoter of the COX2 gene or a complementary sequence. Such mass spectrometric methods are known to those skilled in the art, and the genotyping methods of the invention are amenable to adaptation for the mass spectrometric detection of the polymorphisms of the invention, for example, the COX2 promoter polymorphisms of the invention.

SNPs can also be determined by ligation-bit analysis. This analysis requires two primers that hybridize to a target with a one nucleotide gap between the primers. Each of the four nucleotides is added to a separate reaction mixture containing DNA polymerase, ligase, target DNA and the primers. The polymerase adds a nucleotide to the 3'end of the first primer that is complementary to the SNP, and the ligase then ligates the two adjacent primers together. Upon heating of the sample, if ligation has occurred, the now larger primer will remain hybridized and a signal, for example, fluorescence, can be detected. A further discussion of these methods can be found in U.S. Pat. Nos. 5,919,626; 5,945,283; 5,242,794; and 5,952,174 (each of the foregoing is herein incorporated by reference in its entirety).

U.S. Pat. No. 6,821,733 (herein incorporated by reference in its entirety) describes methods to detect differences in the sequence of two nucleic acid molecules that includes the steps of: contacting two nucleic acids under conditions that allow the formation of a four-way complex and branch migration; contacting the four-way complex with a tracer molecule and a detection molecule under conditions in which the detection molecule is capable of binding the tracer molecule or the four-way complex; and determining binding of the tracer molecule to the detection molecule before and after exposure to the four-way complex. Competition of the four-way complex with the tracer molecule for binding to the detection molecule indicates a difference between the two nucleic acids.

Protein- and proteomics-based approaches are also suitable for polymorphism detection and analysis. Polymorphisms which result in or are associated with variation in expressed proteins can be detected directly by analyzing said proteins. This typically requires separation of the various proteins within a sample, by, for example, gel electrophoresis or HPLC, and identification of said proteins or peptides derived therefrom, for example by NMR or protein sequencing such as chemical sequencing or more prevalently mass spectrometry. Proteomic methodologies are well known in the art, and have great potential for automation. For example, integrated systems, such as the ProteomIQ™ system from Proteome Systems, provide high throughput platforms for proteome analysis combining sample preparation, protein separation, image acquisition and analysis, protein processing, mass spectrometry and bioinformatics technologies.

The majority of proteomic methods of protein identification utilise mass spectrometry, including ion trap mass spectrometry, liquid chromatography (LC) and LC/MSn mass spectrometry, gas chromatography (GC) mass spectroscopy,. Fourier transform-ion cyclotron resonance-mass spectrometer (FT-MS), MALDI-TOF mass spectrometry, and ESI mass spectrometry, and their derivatives. Mass spectrometric methods are also useful in the determination of post-translational modification of proteins, such as phosphorylation or glycosylation, and thus have utility in determining polymorphisms that result in or are associated with variation in post-translational modifications of proteins.

Associated technologies are also well known, and include, for example, protein processing devices such as the "Chemical Inkjet Printer" including piezoelectric printing technology that allows in situ enzymatic or chemical digestion of protein samples electroblotted from 2-D PAGE gels to membranes by jetting the enzyme or chemical directly onto the selected protein spots (Sloane, A. J. et al. High throughput peptide mass fingerprinting and protein macroarray analysis using chemical printing strategies. *Mol Cell Proteomics* 1(7): 490-9 (2002), herein incorporated by reference in its entirety). After in-situ digestion and incubation of the proteins, the membrane can be placed directly into the mass spectrometer for peptide analysis.

A large number of methods reliant on the conformational variability of nucleic acids have been developed to detect SNPs.

For example, Single Strand Conformational Polymorphism (SSCP, Orita et al., *PNAS* 86:2766-2770 (1989), herein incorporated by reference in its entirety) is a method reliant on the ability of single-stranded nucleic acids to form secondary structure in solution under certain conditions. The secondary structure depends on the base composition and can be altered by a single nucleotide substitution, causing differences in electrophoretic mobility under nondenaturing conditions. The various polymorphs are typically detected by autoradiography when radioactively labelled, by silver staining of bands, by hybridisation with detectably labelled probe fragments or the use of fluorescent PCR primers which are subsequently detected, for example by an automated DNA sequencer.

Modifications of SSCP are well known in the art, and include the use of differing gel running conditions, such as for example differing temperature, or the addition of additives, and different gel matrices. Other variations on SSCP are well known to the skilled artisan, including, RNA-SSCP (Gasparini, P. et al. Scanning the first part of the neurofibromatosis type 1 gene by RNA-SSCP: identification of three novel mutations and of two new polymorphisms. *Hum Genet.* 97(4):492-5 (1996), herein incorporated by reference in its entirety), restriction endonuclease fingerprinting-SSCP (Liu, Q. et al. Restriction endonuclease fingerprinting (REF): a sensitive method for screening mutations in long, contiguous segments of DNA. *Biotechniques* 18(3):470-7 (1995), herein incorporated by reference in its entirety), dideoxy fingerprinting (a hybrid between dideoxy sequencing and SSCP) (Sarkar, G. et al. Dideoxy fingerprinting (ddF): a rapid and efficient screen for the presence of mutations. Genomics 13:441-443 (1992), herein incorporated by reference in its entirety), bi-directional dideoxy fingerprinting (in which the dideoxy termination reaction is performed simultaneously with two opposing primers) (Liu, Q. et al. Bi-directional dideoxy fingerprinting (Bi-ddF): a rapid method for quantitative detection of mutations in genomic regions of 300-600 bp. *Hum Mol Genet.* 5(1):107-14 (1996), herein incorporated by reference in its entirety), and Fluorescent PCR-SSCP (in which PCR products are internally labelled with multiple fluorescent dyes, can be digested with restriction enzymes, followed by SSCP, and analysed on an automated DNA sequencer able to detect the fluorescent dyes) (Makino, R. et al. F-SSCP: fluorescence-based polymerase chain reaction-single-strand conformation polymorphism (PCR-SSCP) analysis. *PCR Methods Appl.* 2(1):10-13 (1992), herein incorporated by reference in its entirety).

Other methods which utilise the varying mobility of different nucleic acid structures include Denaturing Gradient Gel Electrophoresis (DGGE) (Cariello, N. F. et al. Resolution of a missense mutant in human genomic DNA by denaturing gradient gel electrophoresis and direct sequencing using in vitro DNA amplification: HPRT Munich. *Am J Hum Genet.* 42(5):726-34 (1988), herein incorporated by reference in its entirety), Temperature Gradient Gel Electrophoresis (TGGE) (Riesner, D. et al. Temperature-gradient gel electrophoresis for the detection of polymorphic DNA and for quantitative polymerase chain reaction. *Electrophoresis.* 13:632-6 (1992), herein incorporated by reference in its entirety), and Heteroduplex Analysis (HET) (Keen, J. et al. Rapid detection of single base mismatches as heteroduplexes on Hydrolink gels. *Trends Genet.* 7(1):5 (1991), herein incorporated by reference in its entirety). Here, variation in the dissociation of double stranded DNA (for example, due to base-pair mismatches) results in a change in electrophoretic mobility. These mobility shifts are used to detect nucleotide variations.

Denaturing High Pressure Liquid Chromatography (HPLC) is yet a further method utilised to detect SNPs, using HPLC methods well-known in the art as an alternative to the separation methods described above (such as gel electrophoresis) to detect, for example, homoduplexes and heteroduplexes which elute from the HPLC column at different rates, thereby enabling detection of mismatch nucleotides and thus SNPs (Giordano, M. et al. Identification by denaturing high-performance liquid chromatography of numerous polymorphisms in a candidate region for multiple sclerosis susceptibility. *Genomics* 56(3):247-53 (1999), herein incorporated by reference in its entirety).

Yet further methods to detect SNPs rely on the differing susceptibility of single stranded and double stranded nucleic acids to cleavage by various agents, including chemical cleavage agents and nucleolytic enzymes. For example, cleavage of mismatches within RNA:DNA heteroduplexes by RNase A, of heteroduplexes by, for example bacteriophage T4 endonuclease YII or T7 endonuclease I, of the 5' end of the hairpin loops at the junction between single stranded and double stranded DNA by cleavase I, and the modification of mispaired nucleotides within heteroduplexes by chemical agents commonly used in Maxam-Gilbert sequencing chemistry, are all well known in the art.

Further examples include the Protein Translation Test (PTT), used to resolve stop codons generated by variations which lead to a premature termination of translation and to protein products of reduced size, and the use of mismatch binding proteins (Moore, W. et al. Mutation detection in the breast cancer gene BRCA1 using the protein truncation test. *Mol Biotechnol.* 14(2):89-97 (2000), herein incorporated by reference in its entirety). Variations are detected by binding of, for example, the MutS protein, a component of *Escherichia coli* DNA mismatch repair system, or the human hMSH2 and GTBP proteins, to double stranded DNA heteroduplexes containing mismatched bases. DNA duplexes are then incubated with the mismatch binding protein, and variations are detected by mobility shift assay. For example, a simple assay is based on the fact that the binding of the mismatch binding protein to the heteroduplex protects the heteroduplex from exonuclease degradation.

Those skilled in the art will know that a particular SNP, particularly when it occurs in a regulatory region of a gene such as a promoter, can be associated with altered expression of a gene. Altered expression of a gene can also result when the SNP is located in the coding region of a protein-encoding gene, for example where the SNP is associated with codons of varying usage and thus with tRNAs of differing abundance. Such altered expression can be determined by methods well known in the art, and can thereby be employed to detect such SNPs. Similarly, where a SNP occurs in the coding region of a gene and results in a non-synonomous amino acid substitution, such substitution can result in a change in the function of the gene product. Similarly, in cases where the gene product is an RNA, such SNPs can result in a change of function in the RNA gene product. Any such change in function, for example as assessed in an activity or functionality assay, can be employed to detect such SNPs.

The above methods of detecting and identifying SNPs are amenable to use in the methods of the invention.

Of course, in order to detect and identify SNPs in accordance with the invention, a sample containing material to be tested is obtained from the subject. The sample can be any sample potentially containing the target SNPs (or target polypeptides, as the case may be) and obtained from any bodily fluid (blood, urine, saliva, etc) biopsies or other tissue preparations.

DNA or RNA can be isolated from the sample according to any of a number of methods well known in the art. For example, methods of purification of nucleic acids are described in Tijssen; Laboratory Techniques in Biochemistry and Molecular Biology: Hybridization with nucleic acid probes Part 1: Theory and Nucleic acid preparation, Elsevier, New York, N.Y. 1993, as well as in Maniatis, T., Fritsch, E. F. and Sambrook, J., Molecular Cloning Manual 1989 (each of the foregoing which is herein incorporated by reference in its entirety).

To assist with detecting the presence or absence of polymorphisms/SNPs, nucleic acid probes and/or primers can be provided. Such probes have nucleic acid sequences specific for chromosomal changes evidencing the presence or absence of the polymorphism and are preferably labeled with a substance that emits a detectable signal when combined with the target polymorphism.

The nucleic acid probes can be genomic DNA or cDNA or MRNA, or any RNA-like or DNA-like material, such as peptide nucleic acids, branched DNAs, and the like. The probes can be sense or antisense polynucleotide probes. Where target polynucleotides are double-stranded, the probes can be either sense or antisense strands. Where the target polynucleotides are single-stranded, the probes are complementary single strands.

The probes can be prepared by a variety of synthetic or enzymatic schemes, which are well known in the art. The probes can be synthesized, in whole or in part, using chemical methods well known in the art (Caruthers et al., *Nucleic Acids Res., Symp. Ser.,* 215-233 (1980), herein incorporated by reference in its entirety). Alternatively, the probes can be generated, in whole or in part, enzymatically.

Nucleotide analogs can be incorporated into probes by methods well known in the art. The only requirement is that the incorporated nucleotide analog must serve to base pair with target polynucleotide sequences. For example, certain guanine nucleotides can be substituted with hypoxanthine, which base pairs with cytosine residues. However, these base pairs are less stable than those between guanine and cytosine. Alternatively, adenine nucleotides can be substituted with 2,6-diaminopurine, which can form stronger base pairs than those between adenine and thymidine.

Additionally, the probes can include nucleotides that have been derivatized chemically or enzymatically. Typical chemical modifications include derivatization with acyl, alkyl, aryl or amino groups.

The probes can be immobilized on a substrate. Preferred substrates are any suitable rigid or semi-rigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which the polynucleotide probes are bound. Preferably, the substrates are optically transparent.

Furthermore, the probes do not have to be directly bound to the substrate, but rather can be bound to the substrate through a linker group. The linker groups are typically about 6 to 50 atoms long to provide exposure to the attached probe. Preferred linker groups include ethylene glycol oligomers, diamines, diacids and the like. Reactive groups on the substrate surface react with one of the terminal portions of the linker to bind the linker to the substrate. The other terminal portion of the linker is then functionalized for binding the probe.

The probes can be attached to a substrate by dispensing reagents for probe synthesis on the substrate surface or by dispensing preformed DNA fragments or clones on the substrate surface. Typical dispensers include a micropipette delivering solution to the substrate with a robotic system to control the position of the micropipette with respect to the substrate. There can be a multiplicity of dispensers so that reagents can be delivered to the reaction regions simultaneously.

Nucleic acid microarrays are preferred. Such microarrays (including nucleic acid chips) are well known in the art (see, for example U.S. Pat. Nos. 5,578,832; 5,861,242; 6,183,698; 6,287,850; 6,291,183; 6,297,018; 6,306,643; and 6,308,170, each of the foregoing which is herein incorporated by reference in its entirety).

Alternatively, antibody microarrays can be produced. The production of such microarrays is essentially as described in Schweitzer & Kingsmore, "Measuring proteins on microarrays", *Curr Opin Biotechnol* 2002; 13(1): 14-9; Avseekno et al., "Immobilization of proteins in immunochemical microarrays fabricated by electrospray deposition", *Anal Chem* 2001 15; 73(24): 6047-52; Huang, "Detection of multiple proteins in an antibody-based protein microarray system, *Immunol Methods* 2001 1; 255 (1-2): 1-13 (each of the foregoing which is herein incorporated by reference in its entirety).

The present invention also contemplates the preparation of kits for use in accordance with the present invention. Suitable kits include various reagents for use in accordance with the present invention in suitable containers and packaging materials, including tubes, vials, and shrink-wrapped and blow-molded packages.

Materials suitable for inclusion in an exemplary kit in accordance with the present invention include one or more of the following: gene specific PCR primer pairs (oligonucleotides) that anneal to DNA or cDNA sequence domains that flank the genetic polymorphisms of interest, reagents capable of amplifying a specific sequence domain in either genomic DNA or cDNA without the requirement of performing PCR; reagents required to discriminate between the various possible alleles in the sequence domains amplified by PCR or non-PCR amplification (e.g., restriction endonucleases, oligonucleotide that anneal preferentially to one allele of the polymorphism, including those modified to contain enzymes or fluorescent chemical groups that amplify the signal from the oligonucleotide and make discrimination of alleles more robust); reagents required to physically separate products derived from the various alleles (e.g. agarose or polyacrylamide and a buffer to be used in electrophoresis, HPLC columns, SSCP gels, formamide gels or a matrix support for MALDI-TOF).

It will be appreciated that the methods of the invention can be performed in conjunction with an analysis of other risk factors known to be associated with lung cancer. Such risk factors include epidemiological risk factors associated with an increased risk of developing lung cancer. Such risk factors include, but are not limited to smoking and/or exposure to tobacco smoke, age, sex and familial history. These risk factors can be used to augment an analysis of one or more polymorphisms as herein described when assessing a subject's risk of developing lung cancer.

The predictive methods of the invention allow a number of therapeutic interventions and/or treatment regimens to be assessed for suitability and implemented for a given subject. The simplest of these can be the provision to the subject of motivation to implement a lifestyle change, for example, where the subject is a current smoker, the methods of the invention can provide motivation to quit smoking.

The manner of therapeutic intervention or treatment will be predicated by the nature of the polymorphism(s) and the biological effect of said polymorphism(s). For example, where a susceptibility polymorphism is associated with a change in the expression of a gene, intervention or treatment is preferably directed to the restoration of normal expression of said gene, by, for example, administration of an agent capable of modulating the expression of said gene. Where a polymorphism is associated with decreased expression of a gene, therapy can involve administration of an agent capable of increasing the expression of said gene, and conversely, where a polymorphism is associated with increased expression of a gene, therapy can involve administration of an agent capable of decreasing the expression of said gene. Methods useful for the modulation of gene expression are well known in the art. For example, in situations where a polymorphism is associated with upregulated expression of a gene, therapy utilising, for example, RNAi or antisense methodologies can be implemented to decrease the abundance of MRNA and so decrease the expression of said gene. Alternatively, therapy can involve methods directed to, for example, modulating the activity of the product of said gene, thereby compensating for the abnormal expression of said gene.

Where a susceptibility polymorphism is associated with decreased gene product function or decreased levels of expression of a gene product, therapeutic intervention or treatment can involve augmenting or replacing of said function, or supplementing the amount of gene product within the subject for example, by administration of said gene product or a functional analogue thereof. For example, where a polymorphism is associated with decreased enzyme function, therapy can involve administration of active enzyme or an enzyme analogue to the subject. Similarly, where a polymorphism is associated with increased gene product function, therapeutic intervention or treatment can involve reduction of said function, for example, by administration of an inhibitor of said gene product or an agent capable of decreasing the level of said gene product in the subject. For example, where a SNP allele or genotype is associated with increased enzyme function, therapy can involve administration of an enzyme inhibitor to the subject.

Likewise, when a protective polymorphism is associated with upregulation of a particular gene or expression of an enzyme or other protein, therapies can be directed to mimic such upregulation or expression in an individual lacking the resistive genotype, and/or delivery of such enzyme or other protein to such individual Further, when a protective polymorphism is associated with downregulation of a particular gene, or with diminished or eliminated expression of an enzyme or other protein, desirable therapies can be directed to mimicking such conditions in an individual that lacks the protective genotype.

The relationship between the various polymorphisms identified above and the susceptibility (or otherwise) of a subject to lung cancer also has application in the design and/or screening of candidate therapeutics. This is particularly the case where the association between a susceptibility or protective polymorphism is manifested by either an upregulation or downregulation of expression of a gene. In such instances, the effect of a candidate therapeutic on such upregulation or downregulation is readily detectable.

For example, in one embodiment existing human lung organ and cell cultures are screened for polymorphisms as set forth above. (For information on human lung organ and cell cultures, see, e.g.: Bohinski et al. (1996) *Molecular and Cellular Biology* 14:5671-5681; Collettsolberg et al. (1996) *Pediatric Research* 39:504; Hermanns et al. (2004) *Laboratory Investigation* 84:736-752; Hume et al. (1996) *In Vitro Cellular & Developmental Biology-Animal* 32:24-29; Leonardi et al. (1995) 38:352-355; Notingher et al. (2003) *Biopolymers (Biospectroscopy)* 72:230-240; Ohga et al. (1996) *Biochemical and Biophysical Research Communications* 228:391-396; each of the foregoing which is herein incorporated by reference in its entirety.) Cultures representing susceptibility and protective genotype groups are selected, together with cultures which are putatively "normal" in terms of the expression of a gene which is either upregulated or downregulated where a protective polymorphism is present.

Samples of such cultures are exposed to a library of candidate therapeutic compounds and screened for any or all of: (a) downregulation of susceptibility genes that are normally upregulated in susceptibility polymorphisms; (b) upregulation of susceptibility genes that are normally downregulated in susceptibility polymorphisms; (c) downregulation of protective genes that are normally downregulated or not expressed (or null forms are expressed) in protective polymorphisms; and (d) upregulation of protective genes that are normally upregulated in protective polymorphisms. Compounds are selected for their ability to alter the regulation and/or action of susceptibility genes and/or protective genes in a culture having a susceptibility polymorphisms.

Similarly, where the polymorphism is one which when present results in a physiologically active concentration of an expressed gene product outside of the normal range for a subject (adjusted for age and sex), and where there is an available prophylactic or therapeutic approach to restoring levels of that expressed gene product to within the normal range, individual subjects can be screened to determine the likelihood of their benefiting from that restorative approach. Such screening involves detecting the presence or absence of the polymorphism in the subject by any of the methods described herein, with those subjects in which the polymorphism is present being identified as individuals likely to benefit from treatment.

EXAMPLES

The invention will now be described in more detail, with reference to non-limiting examples.

Example 1

Case Association Study
Introduction

Case-control association studies allow the careful selection of a control group where matching for important risk factors is critical. In this study, smokers diagnosed with lung cancer and smokers without lung cancer with normal lung function were compared. This unique control group is highly relevant as it is impossible to pre-select smokers with zero risk of lung cancer—i.e., those who although smokers will never develop lung cancer. Smokers with a high pack year history and normal lung function were used as a "low risk" group of smokers, as it is believed that it is not possible with current knowledge to identify a lower risk group of smokers. It is believed, without wishing to be bound by any theory, that this approach allows for a more rigorous comparison of low penetrant, high frequency polymorphisms that can confer an increased risk of developing lung cancer. It is also believed, again without wishing to be bound by any theory, that there can be polymorphisms that confer a degree of protection from lung cancer which may only be evident if a smoking cohort with normal lung function is utilised as a comparator group. Thus smokers with lung cancer would have a lower frequency of these polymorphisms compared to smokers with normal lung function and no diagnosed lung cancer.

Methods
Subject Recruitment

Subjects of European decent who had smoked a minimum of fifteen pack years and diagnosed with lung cancer were recruited. Subjects met the following criteria: diagnosed with lung cancer based on radiological and histological grounds, including primary lung cancers with histological types of small cell lung cancer, squamous cell lung cancer, adenocarinoma of the lung, non-small cell cancer (where histological markers can not distinguish the subtype) and broncho-alveolar carcinoma. Subjects can be of any age and at any stage of treatment after the diagnosis had been confirmed. One hundred and nine subjects were recruited, of these 58% were male, the mean FEV1/FVC (±95% confidence limits) was 51% (49-53), mean FEV1 as a percentage of predicted was 43 (41-45). Mean age, cigarettes per day and pack year history was 65 yrs (64-66), 24 cigarettes/day (22-25) and 50 pack years (41-55), respectively. Two hundred and seventeen European subjects who had smoked a minimum of twenty pack years and who had never suffered breathlessness and had not been diagnosed with an obstructive lung disease or lung cancer in the past were also studied. This control group was recruited through clubs for the elderly and consisted of 63% male, the mean FEV1/FVC (95% CI) was 82% (81-83), mean FEV1 as a percentage of predicted was 96 (95-97). Mean age, cigarettes per day and pack year history was 59 yrs (57-61), 24 cigarettes/day (22-26) and 42 pack years (39-45), respectively. Using a PCR based method (Sandford A J, et al., 1999. Z and S mutations of the al-antitrypsin gene and the risk of chronic obstructive pulmonary disease. *Am J Respir Cell Mol Biol.* 20; 287-291, herein incorporated by reference in its entirety), all subjects were genotyped for the α1-antitrypsin mutations (S and Z alleles) and those with the ZZ allele were excluded. 190 European blood donors (smoking status unknown) were recruited consecutively through local blood donor services. Sixty-three percent were men and their mean age was 50 years. On regression analysis, the age difference and pack years difference observed between lung cancer sufferers and resistant smokers was found not to determine FEV or lung cancer.

This study shows that polymorphisms found in greater frequency in lung cancer patients compared to resistant smokers can reflect an increased susceptibility to the development of lung cancer. Similarly, polymorphisms found in greater frequency in resistant smokers compared to lung cancer can reflect a protective role. A summary is presented in Table 1C below.

TABLE 1C

Summary of characteristics for the lung cancer subjects and resistant smokers.

| Parameter Median (IQR) | Lung Cancer N = 109 | Resistant smokers N = 200 | Differences |
|---|---|---|---|
| % male | 52% | 64% | ns |
| Age (yrs) | 68 (11) | 60 (12) | $P < 0.05$ |
| Pack years | 40 (31) | 43 (25) | $P < 0.05$ |
| Cigarettes/day | 18 (11) | 24 (12) | ns |
| FEV1 (L) | 1.7 (0.6) | 2.8 (0.7) | $P < 0.05$ |
| FEV1 % predict | 67 (22) | 96% (10) | $P < 0.05$ |
| FEV1/FVC | 59 (14) | 82 (8) | $P < 0.05$ |

Means and 95% confidence limits

Glutathione S-transferase Null Polymorphisms Genotyping

Genomic DNA was extracted using standard phenol and chloroform methods. Cohorts of patients and controls were configured in to 96-well PCR format containing strategic negative controls. The assay primers, PCR conditions and RFLP assays details have been previously described [Cantlay A M. et al. Heterogeneous expression and polymorphic genotype of glutathione S-transferases in human lung. *Thorax* 49(10):1010-4, (1994), herein incorporated by reference in its entirety]. Genotyping was done using minor modifications of the above protocol optimised for our own laboratory conditions The PCR reactions were amplified in MJ Research thermocyclers in a total volume of 25 µl and contained 80 ng genomic DNA, 100 ng forward and reverse primers, 200 mM dNTPs, 20 mM Tris-HCL (pH 8.4), 50 mM KCl, 2.5 mM MgCl2 and 1.0 unit of Taq polymerase (Qiagen). Forward, internal (GSTM4) and reverse prime sequences were 5'-CTGCCCTACTTGATTGATGG-3' [SEQ ID NO 143], 5'-ATCTTCTCCTCTTCTGTCTC-3' [SEQ ID NO 144], and 5'-TTCTGGATTGTAGCAGATCA-3' [SEQ ID NO 145]. Cycling conditions consisted of 94 C 60 s, 59 C 30 s, 72 C 30 s for 35 cycles with an extended last extension of 3 min. Digested products were separated on 3% agarose gel. The products were visualised by ultraviolet transillumination following ethidium bromide staining and migration compared against a 1 Kb plus ladder standard (Invitrogen). Genotypes were recorded in data spreadsheets and statistical analysis performed.

Cyclooxygenase 2 Polymorphisms Genotyping

Genomic DNA was extracted from whole blood samples (Maniatis, T., Fritsch, E. F. and Sambrook, J., Molecular Cloning Manual. 1989). The Cyclo-oxygenase 2 −765 polymorphism was determined by minor modifications of a previously published method (Papafili A, et al. Common promoter variant in cyclooxygenase-2 represses gene expression. *Arterioscler Thromb Vasc Biol.* 20: 1631-1635, (2002), herein incorporated by reference in its entirety). The PCR reaction was carried out in a total volume of 25 ul and contained 20 ng genomic DNA, 500 pmol forward and reverse primers, 0.2 mM dNTPs, 10 mM Tris-HCL (pH 8.4), 150 mM KCl, 1.0 mM $MgCl_2$ and 1 unit of polymerase (Life Technologies). Cycling times were incubations for 3 min at 95° C. followed by 33 cycles of 50s at 94° C., 60s at 66° C. and 60s at 72° C. A final elongation of 10 min at 72° C. then followed. 4 ul of PCR products were visualised by ultraviolet trans-illumination of a 3% agarose gel stained with ethidium bromide. An aliquot of 3 ul of amplification product was digested for 1 hr with 4 units of AciI (Roche Diagnostics, New Zealand) at 37° C. Digested products were separated on a 2.5% agarose gel run for 2.0 hours at 80 mV with TBE buffer. The products were visualised against a 123 bp ladder using ultraviolet transillumination after ethidium bromide staining.

Matrix Metalloproteinase 1-1607 1G/2G Polymorphisms Genotyping

Genomic DNA was extracted using standard phenol and chloroform methods. Cohorts of patients and controls were configured in to 96-well PCR format containing strategic negative controls. The assay primers, PCR conditions and RFLP assays details have been previously described [Dunleavey L, et al. Rapid genotype analysis of the matrix metalloproteinase-1 gene 1G/2G polymorphism that is associated with risk of cancer. *Matrix Biol.* 19(2):175-7 (2000), herein incorporated by reference in its entirety]. Genotyping was done using minor modifications of the above protocol optimised for our own laboratory conditions The PCR reactions were amplified in MJ Research thermocyclers in a total volume of 25 µl and contained 80 ng genomic DNA, 100 ng forward and reverse primers, 200 mM dNTPs, 20 mM Tris-HCL (pH 8.4), 50 mM KCl, 1.5 mM $MgCl_2$ and 1.0 unit of Taq polymerase (Qiagen). Forward and reverse prime sequences were 5'-TCGTGAGAATGTCTTCCCATT-3' [SEQ ID NO 1] and 5'-TCTTGGATTGATTTGAGATAAGT-GAAATC-3'[SEQ ID NO 2]. Cycling conditions consisted of 94° C. 60 s, 55° C. 30s, 72° C. 30 s for 35 cycles with an extended last extension of 3 min. Aliquots of amplification product were digested for 4 hrs with 6 Units of the restriction enzymes XmnI (Roche Diagnostics, New Zealand) at designated temperature conditions. Digested products were separated on 6% polyacrylamide gel. The products were visualised by ultraviolet transillumination following ethidium bromide staining and migration compared against a 1 Kb plus ladder standard (Invitrogen). Genotypes were recorded in data spreadsheets and statistical analysis performed.

Polymorphism Genotyping Using the Sequenom Autoflex Mass Spectrometer

Genomic DNA was extracted from whole blood samples (Maniatis, T., Fritsch, E. F. and Sambrook, J., Molecular Cloning Manual. 1989). Purified genomic DNA was aliquoted (10 ng/ul concentration) into 96 well plates and genotyped on a Sequenom™ system (Sequenom™ Autoflex Mass Spectrometer and Samsung 24 pin nanodispenser) using the following sequences, amplification conditions and methods.

The following conditions were used for the PCR multiplex reaction: final concentrations were for 10× Buffer 15 mM MgCl2 1.25×, 25 mM MgCl2 1.625 mM, dNTP mix 25 mM 500 uM, primers 4 uM 100 nM, Taq polymerase (Quiagen hot start) 0.15 U/reaction, Genomic DNA 10 ng/ul. Cycling times were 95° C. for 15 min, (5° C. for 15 s, 56° C. 30 s, 72° C. 30 s for 45 cycles with a prolonged extension time of 3 min to finish. We used shrimp alkaline phosphotase (SAP) treatment (2 ul to 5 ul per PCR reaction) incubated at 35° C. for 30 min and extension reaction (add 2 ul to 7 ul after SAP treatment) with the following volumes per reaction of: water, 0.76 ul; hME 10× termination buffer, 0.2 ul; hME primer (10 uM), 1 ul; MassEXTEND enzyme, 0.04 ul.

TABLE 1D

| Sequenom conditions for the polymorphisms genotyping - 1 | | | |
|---|---|---|---|
| TERM | SNP_ID | 2nd-PCRP | 1st-PCRP |
| ACT | CYP2E1_1019 G/CPst1 | ACGTTGGATGAAACCAGAGGGAAGCAAAGG [SEQ ID NO 3] | ACGTTGGATGTCATTGGTTGTGCTGCACCT [SEQ ID NO 4] |
| ACT | XPD-751 G/T | ACGTTGGATGCACCAGGAACCGTTTATGGC [SEQ ID NO 5] | ACGTTGGATGAGCAGCTAGAATCAGAGGAG [SEQ ID NO 6] |
| ACT | IL-18 105 A/C | ACGTTGGATGGTCAATGAAGAGAACTTGGTC [SEQ ID NO 7] | ACGTTGGATGAATGTTTATTGTAGAAAACC [SEQ ID NO 8] |
| ACT | IL-18-133 G/C | ACGTTGGATGGGGTATTCATAAGCTGAAAC [SEQ ID NO 9] | ACGTTGGATGCCTTCAAGTTCAGTGGTCAG [SEQ ID NO 10] |
| ACT | CYP 1A1 Ile 462 Val | ACGTTGGATGGTGATTATCTTTGGCATGGG [SEQ ID NO 11] | ACGTTGGATGGGATAGCCAGGAAGAGAAAG [SEQ ID NO 12] |
| ACT | MMP12 Asn 357 Ser A/G | ACGTTGGATGCCCTATTTCTTTGTCTTCAC [SEQ ID NO 13] | ACGTTGGATGCTTGGGATAATTTGGCTCTG [SEQ ID NO 14] |
| ACT | OGG1 Ser 326 Cys G/C | ACGTTGGATGGGAACCCTTTCTGCGCTTTG [SEQ ID NO 15] | ACGTTGGATGCCTACAGGTGCTGTTCAGTG [SEQ ID NO 16] |
| ACT | NAT2 Arg 197 Gln A/G | ACGTTGGATGCCTGCCAAAGAAGAAACACC [SEQ ID NO 17] | ACGTTGGATGACGTCTGCAGGTATGTATTC [SEQ ID NO 18] |
| ACT | CYP2E1_C/T Rsa1 | ACGTTGGATGGTTCTTAATTCATAGGTTGC [SEQ ID NO 19] | ACGTTGGATGCTTCATTTCTCATCATATTTTC [SEQ ID NO 20] |
| ACG | CCND1 A870G | ACGTTGGATGTAGGTGTCTCCCCCTGTAAG [SEQ ID NO 21] | ACGTTGGATGTCCTCTCCAGAGTGATCAAG [SEQ ID NO 22] |
| ACG | ILB1-511 A/G | ACGTTGGATGATTTTCTCCTCAGAGGCTCC [SEQ ID NO 23] | ACGTTGGATGTGTCTGTATTGAGGGTGTGG [SEQ ID NO 24] |
| ACG | FAS_A-670G | ACGTTGGATGTTGTGGCTGCAACATGAGAG [SEQ ID NO 25] | ACGTTGGATGCTATGGCGCAACATCTGTAC [SEQ ID NO 26] |
| ACG | NOS3-786 T/C | ACGTTGGATGACTGTAGTTTCCCTAGTCCC [SEQ ID NO 27] | ACGTTGGATGAGTCAGCAGAGAGACTAGGG [SEQ ID NO 28] |
| ACT | ACT_Ala15Thr | ACGTTGGATGGAGTTGAGAATGGAGAGAATG [SEQ ID NO 29] | ACGTTGGATGTCAAGTGGGCTGTTAGGGTG [SEQ ID NO 30] |
| ACT | SOD3 Arg 312 Gln | ACGTTGGATGTGCTGCGTGGTGGGCGTGTG [SEQ ID NO 31] | ACGTTGGATGGGCCTTGCACTCGCTCTCG [SEQ ID NO 32] |
| ACT | NOS3 Asp 298 Glu | ACGTTGGATGAAACGGTCGCTTCGACGTGC [SEQ ID NO 33] | ACGTTGGATGACCTCAAGGACCAGCTCGG [SEQ ID NO 34] |
| CGT | IL-8-251 A/T | ACGTTGGATGACTGAAGCTCCACAATTTGG [SEQ ID NO 35] | ACGTTGGATGGCCACTCTAGTACTATATCTG [SEQ ID NO 36] |
| CGT | IFN gamma 874 A/T | ACGTTGGATGCAGACATTCACAATTGATTT [SEQ ID NO 37] | ACGTTGGATGGATAGTTCCAAACATGTGCG [SEQ ID NO 38] |
| ACT | XRCC1 Arg 399 Gln G/A | ACGTTGGATGTAAGGAGTGGGTGCTGGACT [SEQ ID NO 39] | ACGTTGGATGAGGATAAGGAGCAGGGTTGG [SEQ ID NO 40] |

| Sequenom conditions for the polymorphisms genotyping - 2 | | | | | | | | |
|---|---|---|---|---|---|---|---|---|
| SNP_ID | AMP_LEN | UP_CONF | MP_CONF | Tm(NN) | PcGC | PWARN | UEP_DIR | UEP_MASS |
| CYP2E1_1019G/CPst1 | 119 | 95.2 | 71.3 | 46.7 | 47.1 | | F | 5256.4 |
| XPD-751 G/T | 113 | 97.6 | 71.3 | 49.8 | 47.4 | | F | 5689.7 |
| IL-18 105 A/C | 120 | 65.6 | 71.3 | 49.8 | 36.4 | | R | 6702.4 |
| IL-18-133 G/C | 112 | 93.5 | 81.3 | 47.1 | 42.1 | | F | 5811.8 |
| CYP 1A1 Ile 462 Val | 102 | 98.2 | 81.3 | 55.6 | 55 | | F | 6222.1 |
| MMP12 Asn 357 Ser A/G | 95 | 92.6 | 81.3 | 48 | 30.4 | | F | 7070.6 |
| OGG1 Ser 326 Cys G/C | 99 | 96.5 | 82.2 | 58.9 | 70.6 | | R | 5227.4 |
| NAT2 Arg 197 Gln A/G | 115 | 97.4 | 70 | 48.5 | 36.4 | | F | 6635.3 |

TABLE 1D-continued

| | | | | | | | |
|---|---|---|---|---|---|---|---|
| CYP2E1_C/T Rsa1 | 105 | 62.8 | 77.8 | 46.4 | 26.1 | R | 7018.6 |
| CCND1 A870G | 106 | 98.1 | 83 | 45.8 | 47.1 | R | 5034.3 |
| ILB1-511 A/G | 111 | 99.2 | 83 | 46 | 47.1 | R | 5203.4 |
| FAS_A-670G | 103 | 99.2 | 83 | 54.4 | 50 | R | 6166 |
| NOS3-786 T/C | 114 | 97.5 | 83 | 61.8 | 61.9 | F | 6358.1 |
| ACT_Ala15Thr | 118 | 93.4 | 68.2 | 45.2 | 47.1 | F | 5136.4 |
| SOD3 Arg 312 Gln | 119 | 63.2 | 68.2 | 55.5 | 57.9 | F | 5855.8 |
| NOS3 Asp 298 Glu | 113 | 82.2 | 68.2 | 65.4 | 66.7 | F | 6432.2 |
| IL-8-251 A/T | 119 | 92.6 | 75.8 | 45.9 | 28.6 | R | 6428.2 |
| IFN gamma 874 A/T | 112 | 75.3 | 75.8 | 46.4 | 26.1 | F | 6943.6 |
| XRCC1 Arg 399 Gln G/A | 109 | 93.6 | 93.6 | 66.8 | 82.4 | F | 5099.3 |

Sequenom conditions for the polymorphisms genotyping - 3

| SNP_ID | UEP_SEQ | EXT1_CALL | EXT1_MASS | EXT1_SEQ | EXT2_CALL |
|---|---|---|---|---|---|
| CYP2E1_1019G/CPst1 | TTCTTGGTTCAGGAGAG [SEQ ID NO 41] | C | 5529.6 | TTCTTGGTTCAGGAGAGC [SEQ ID NO 421] | G |
| XPD-751 G/T | GCAATCTGCTCTATCCTCT [SEQ ID NO 43] | T | 5977.9 | GCAATCTGCTCTATCCTCTT [SEQ ID NO 44] | G |
| IL-18 105 A/C | ATTCAAGCTTGCCAAAGTAATC [SEQ ID NO 45] | A | 6990.6 | ATTCAAGCTTGCCAAAGTAATCT [SEQ ID NO 46] | C |
| IL-18-133 G/C | CATAAGCTGAAACTTCTGG [SEQ ID NO 47] | C | 6085 | CATAAGCTGAAACTTCTGGC [SEQ ID NO 48] | G |
| CYP 1A1 Ile 462 Val | GGAAGTGTATCGGTGAGACC [SEQ ID NO 49] | A | 6519.3 | GGAAGTGTATCGGTGAGACCA [SEQ ID NO 50] | G |
| MMP12 Asn 357 Ser A/G | TGACAAATACTGGTTAATTAGCA [SEQ ID NO 51] | A | 7367.8 | TGACAAATATCGGTTAATTAGCAA [SEQ ID NO 52] | G |
| OGG1 Ser 326 Cys G/C | GCTCCTGAGCATGGCGG [SEQ ID NO 53] | G | 5500.6 | GCTCCTGAGCATGGCGGC [SEQ ID NO 54] | C |
| NAT2 Arg 197 Gln A/G | TACTTATTTACGCTTGAACCTC [SEQ ID NO 55] | A | 6932.5 | TACTTATTTACGCTTGAACCTCA [SEQ ID NO 56] | G |
| CYP2E1_C/T Rsa1 | CTTAATTCATAGGTTGCAATTTT [SEQ ID NO 57] | T | 7315.8 | CTTAATTCATAGGTTGCAATTTTA [SEQ ID NO 58] | C |
| CCND1 A870G | ACATCACCCTCACTTAC [SEQ ID NO 59] | G | 5307.5 | ACATCACCCTCACTTACC [SEQ ID NO 60] | A |
| ILB1-511 A/G | AATTGACAGAGAGCTCC [SEQ ID NO 61] | G | 5476.6 | AATTGACAGAGAGCTCCC [SEQ ID NO 62] | A |
| FAS_A-670G | ATGAGAGGCTCACAGACGTT [SEQ ID NO 63] | G | 6439.2 | ATGAGAGGCTCACAGACGTTC [SEQ ID NO 64] | A |
| NOS3-786 T/C | GGCATCAAGCTCTTCCCTGGC [SEQ ID NO 65] | C | 6631.3 | GGCATCAAGCTCTTCCCTGGCC [SEQ ID NO 66] | T |
| ACT_Ala15Thr | GAATGTTACCTCTCCTG [SEQ ID NO 67] | A | 5433.6 | GAATGTTACCTCTCCTGA [SEQ ID NO 68] | G |
| SOD3 Arg 312 Gln | GCACTCAGAGCGCAAGAAG [SEQ ID NO 69] | C | 6129 | GCACTCAGAGCGCAAGAAGC [SEQ ID NO 70] | G |
| NOS3 Asp 298 Glu | GCTGCTGCAGGCCCCAGATGA [SEQ ID NO 71] | T | 6720.4 | GCTGCTGCAGGCCCCAGATGAT [SEQ ID NO 72] | G |
| IL-8-251 A/T | CACAATTTGGTGAATTATCAA [SEQ ID NO 73] | A | 6716.4 | CACAATTTGGTGAATTATCAAT [SEQ ID NO 74] | T |

TABLE 1D-continued

| IFN gamma 874 A/T | TTCTTACAACACAAAATCAAATC [SEQ ID NO 75] | T | 7231.8 | TTCTTACAACACAAAATCAAATCT [SEQ ID NO 76] | A |
|---|---|---|---|---|---|
| XRCC1 Arg 399 Gln G/A | TCGGCGGCTGCCCTCCC [SEQ ID NO 77] | A | 5396.5 | TCGGCGGCTGCCCTCCCA [SEQ ID NO 78] | G |

Sequenom conditions for the polymorphisms genotyping - 4

| SNP_ID | EXT2_MASS | EXT2_SEQ | | 1stPAUSE |
|---|---|---|---|---|
| CYP2E1_1019G/CPst1 | 5873.8 | TTCTTGGTTCAGGAGAGGT | [SEQ ID NO 79] | 5585.6 |
| XPD-751 G/T | 6292.1 | GCAATCTGCTCTATCCTCTGC | [SEQ ID NO 80] | 6018.9 |
| IL-18 105 A/C | 7658 | ATTCAAGCTTGCCAAAGTAATCGGA | [SEQ ID NO 81] | 7031.6 |
| IL-18-133 G/C | 6438.2 | CATAAGCTGAAACTTCTGGGA | [SEQ ID NO 82] | 6141 |
| GYP 1A1 Ile 462 Val | 6839.5 | GGAAGTGTATCGGTGAGACCGT | [SEQ ID NO 83] | 6551.3 |
| MMP12 Asn 357 Ser A/G | 7688 | TGACAAATACTGGTTAATTAGCAGT | [SEQ ID NO 84] | 7399.8 |
| OGG1 Ser 326 Cys G/C | 5853.8 | GCTCCTGAGCATGGCGGGA | [SEQ ID NO 85] | 5556.6 |
| NAT2 Arg 197 Gln A/G | 7261.8 | TACTTATTTACGCTTGAACCTCGA | [SEQ ID NO 86] | 6964.5 |
| CYP2E1_C/T Rsa1 | 7636 | CTTAATTCATAGGTTGCAATTTTGT | [SEQ ID NO 871 | 7347.8 |
| CCND1 A870G | 5651.7 | ACATCACCCTCACTTACTG | [SEQ ID NO 88] | 5338.5 |
| ILB1-511 A/G | 5820.8 | AATTGACAGAGAGCTCCTG | [SEQ ID NO 89] | 5507.6 |
| FAS_A-670G | 6743.4 | ATGAGAGGCTCACAGACGTTTC | [SEQ ID NO 90] | 6470.2 |
| NOS3-786 T/C | 6975.5 | GGCATCAAGCTCTTCCCTGCTG | [SEQ ID NO 91] | 6662.3 |
| ACT_Ala15Thr | 5738.7 | GAATGTTACCTCTCCTGGC | [SEQ ID NO 92] | 5465.6 |
| SOD3 Arg 312 Gln | 7116.6 | GCACTCAGAGCGCAAGAAGGGGC | [SEQ ID NO 93] | 6185 |
| NOS3 Asp 298 Glu | 7034.6 | GCTGCTGCAGGCCCCAGATGAGC | [SEQ ID NO 94] | 6761.4 |
| IL-8-251 A/T | 7029.6 | CACAATTTGGTGAATTATCAAAT | [SEQ ID NO 95] | 6741.4 |
| IFN gamma 874 A/T | 7530 | TTCTTACAACACAAAATCAAATCAC | [SEQ ID NO 96] | 7256.8 |
| XRCC1 Arg 399 G/n G/A | 6054.9 | TCGGCGGCTGCCCTCCCGGA | [SEQ ID NO 97] | 5428.5 |

Sequenom conditions for the polymorphisms genotyping - 5

| TERM | SNP_ID | 2nd-PCRP | 1st-PCRP |
|---|---|---|---|
| ACT | CTGF-447G/C | ACGTTGGATGAGGTAGCTGAAGAGGCAAAC [SEQ ID NO 98] | ACGTTGGATGGCCTATAGCCTCTAAAACGC [SEQ ID NO 99] |
| ACT | NBS1 Gln185Glu G/C | ACGTTGGATGCTTTCAATTTGTGGAGGCTG [SEQ ID NO 100] | ACGTTGGATGTGTGCACTCATTTGTGGACG [SEQ ID NO 101] |
| ACT | MBL2 161 G/A | ACGTTGGATGGTAGCTCTCCAGGCATCAAC [SEQ ID NO 102] | ACGTTGGATGGTACCTGGTTCCCCCTTTTC [SEQ ID NO 103] |
| ACT | IGF2R Leu252Val C/G | ACGTTGGATGACACCAGGCGTTTGATGTTG [SEQ ID NO 104] | ACGTTGGATGAAAAACGCCAACAGCATCGG [SEQ ID NO 105] |
| ACT | MUC5AC-221 C/T | ACGTTGGATGAGGCGGAGATGGGTGTGTC [SEQ ID NO 106] | ACGTTGGATGAGTCTAGGGTGGGGTATGTG [SEQ ID NO 107] |
| ACT | Arg1 intron1 C/T | ACGTTGGATGATGTGTGGATTCACAGCTCG [SEQ ID NO 108] | ACGTTGGATGGGGGTTGGCAACTCTAAAAGG [SEQ ID NO 109] |
| ACT | REV1 Phe257Ser C/T | ACGTTGGATGCTCTGAAATCAGTGCTGCTC [SEQ ID NO 110] | ACGTTGGATGATGGTCAACAGTGTTGCCAG [SEQ ID NO 111] |
| ACT | Apex1 Asp148Glu G/T | ACGTTGGATGCACCTCTTGATTGCTTTCCC [SEQ ID NO 112] | ACGTTGGATGACCCGGCCTTCCTGATCATG [SEQ ID NO 113] |
| ACG | IL-10-1082 A/G | ACGTTGGATGATTCCATGGAGGCTGGATAG [SEQ ID NO 114] | ACGTTGGATGGACAACACTACTAAGGCTTC [SEQ ID NO 115] |

TABLE 1D-continued

| Sequenom conditions for the polymorphisms genotyping - 6 | | | | | | | |
|---|---|---|---|---|---|---|---|
| SNP_ID | AMP_LEN | UP_CONF | MP_CONF | Tm(NN) | PcGC | PWARN | UEP_DIR | UEP_MASS |
| CTGF-447G/C | 119 | 98.2 | 65 | 52 | 52.9 | | R | 5090.3 |
| NBS1 Gln185Glu G/C | 118 | 97 | 65 | 51 | 52.9 | | R | 5192.4 |
| MBL2 161 G/A | 99 | 96.8 | 65 | 50.3 | 52.9 | | F | 5299.5 |
| IGF2R Leu252Val C/G | 114 | 98.5 | 67.8 | 68.6 | 82.4 | | F | 5206.4 |
| MUC5AC-221 C/T | 119 | 81.8 | 67.8 | 56.9 | 64.7g | | R | 5273.4 |
| Arg1 intron1 C/T | 102 | 99.6 | 67.8 | 53.3 | 52.6 | | R | 5932.9 |
| REV1 Phe257Ser C/T | 105 | 99.6 | 67.8 | 57.5 | 55 | | R | 6003.9 |
| Apex1 Asp148Glu G/T | 114 | 92.9 | 67.8 | 46.8 | 35 | | F | 6113 |
| IL-10-1082A/G | 107 | 98 | 68.8 | 51.2 | 58.8 | | R | 4977.2 |

| Sequenom conditions for the polymorphisms genotyping - 7 | | | | |
|---|---|---|---|---|
| SNP_ID | UEP_SEQ | EXT1_CALL | EXT1_MASS | EXT1_SEQ |
| CTGF-447 G/C | AAAAGGTTTCTCCCCCC [SEQ ID NO 116] | G | 5363.5 | AAAAGGTTTCTCCCCCCC [SEQ ID NO 117] |
| NBS1 Gln185Glu G/C | AGGCTGCTTCTTGGACT [SEQ ID NO 118] | G | 5465.6 | AGGCTGCTTCTTGGACTC [SEQ ID NO 119] |
| MBL2 161 G/A | CAAAGATGGGCGTGATG [SEQ ID NO 120] | A | 5596.7 | CAAAGATGGGCGTGATGA [SEQ ID NO 121] |
| IGF2R Leu252Val C/G | GCCAGCCCCGGGACGGA [SEQ ID NO 122] | C | 5479.6 | GCCAGCCCCGGGACGGAC [SEQ ID NO 123] |
| MUC5AC-221 C/T | ATGGGTGTGTCTGCCGG [SEQ ID NO 124] | T | 5570.6 | ATGGGTGTGTCTGCCGGA [SEQ ID NO 125] |
| Arg1 intron1 C/T | GGCTGTAAGGAAATCTGGG [SEQ ID NO 126] | T | 6230.1 | GGCTGTAAGGAAATCTGGGA [SEQ ID NO 127] |
| REV1 Phe257Ser C/T | CCTTATCCTCCTCCTGGGAA [SEQ ID NO 128] | T | 6301.1 | CCTTATCCTCCTCCTGGGAAA [SEQ ID NO 129] |
| Apex1 Asp148Glu G/T | TGTTTCATTTCTATAGGCGA [SEQ ID NO 130] | T | 6401.2 | TGTTTCATTTCTATAGGCGAT [SEQ ID NO 131] |
| IL-10-1082 A/G | CCTATCCCTACTTCCCC [SEQ ID NO 132] | G | 5250.4 | CCTATCCCTACTTCCCCC [SEQ ID NO 133] |

| Sequenom conditions for the polymorphisms genotyping - 8 | | | | |
|---|---|---|---|---|
| SNP_ID | EXT2_CALL | EXT2_MASS | EXT2_SEQ | | 1stPAUSE |
| CTGF-447G/C | C | 5716.7 | AAAAGGTTTCTCCCCCCGA | [SEQ ID NO 134] | 5419.5 |
| NBS1 Gln185Glu G/C | C | 5818.8 | AGGCTGCTTCTTGGACTGA | [SEQ ID NO 135] | 5521.6 |
| MBL2 161 G/A | G | 5901.9 | CAAAGATGGGCGTGATGGC | [SEQ ID NO 136] | 5628.7 |
| IGF2R Leu252Val C/G | G | 5823.8 | GCCAGCCCCGGGACGGAGT | [SEQ ID NO 137] | 5535.6 |
| MUC5AC -221 C/T | C | 5890.8 | ATGGGTGTGTCTGCCGGGT | [SEQ ID NO 138] | 5602.6 |
| Arg1 intron1 C/T | C | 6879.5 | GGCTGTAAGGAAATCTGGGGGT | [SEQ ID NO 139] | 6262.1 |
| REV1 Phe257Ser C/T | C | 6630.3 | CCTTATCCTCCTCCTGGGAAGA | [SEQ ID NO 140] | 6333.1 |
| Apex1 Asp148Glu G/T | G | 7068.6 | TGTTTCATTTCTATAGGCGAGGA | [SEQ ID NO 141] | 6442.2 |
| IL-10 -1082 A/G | A | 5858.8 | CCTATCCCTACTTCCCCTTC | [SEQ ID NO 142] | 5281.4 |

Results

Example 2

Nitric Oxide Synthase 3 Asp 298 Glu (T/G) Polymorphism Allele and Genotype Frequencies in the Lung Cancer Patients, Resistant Smokers and Controls

The genotype frequency for the above allele was determined in lung cancer patients, resistant smokers, and controls. The frequencies are shown in the following table.

TABLE 1E

Nitric oxide synthase 3 Asp 298 Glu (T/G) polymorphism allele and genotype frequencies in the lung cancer patients, resistant smokers and controls.

| Frequency | Allele* | | Genotype | | |
|---|---|---|---|---|---|
| | T | G | TT | TG | GG |
| Controls n = 183 (%) | 108 (30%) | 258 (70%) | 13 (7%) | 82 (45%) | 88 (48%) |
| Lung Cancer n = 107 (%) | 71 (33%) | 143 (67%) | 9 (8%) | 53 (50%) | 45 (42%) |
| Resistant n = 198 (%) | 135 (34%) | 261 (66%) | $28^{1,2}$ (14%) | 79 (40%) | 91 (46%) |

*number of chromosomes (2n)

A mathematical analysis of the data in the table indicated that:
1. Genotype. TT vs TG/GG for resistant vs lung cancer, Odds ratio (OR)=1.8, 95% confidence limits 0.8-4.3, $\chi^2$ (Yates uncorrected)=2.14, p=0.14, TT genotype=protective for lung cancer; and
2. Genotype. TT vs TG/GG for resistant vs controls, Odds ratio (OR)=2.2, 95% confidence limits 1.0-4.6, $\chi^2$ (Yates corrected)=4.2, p=0.04, TT genotype=protective for lung cancer.

Thus, for the Asp 298 Glu (T/G) polymorphism of the Nitric oxide synthase 3 gene, the TT genotype was found to be greater in the smoking resistant cohort compared to the lung cancer cohort (OR=1.8, P=0.14) consistent with a protective role. This greater frequency compared to the blood donor cohort also suggests that the TT genotype is over represented in the resistant group (see Table 1E)

Example 3

Nitric Oxide Synthase 3 −786 T/C Polymorphism Allele and Genotype Frequencies in the Lung Cancer Patients, Resistant Smokers and Controls

The genotype frequency for the above allele was determined in lung cancer patients, resistant smokers, and controls. The frequencies are shown in the following table.

TABLE 1F

Nitric oxide synthase 3 −786 T/C polymorphism allele and genotype frequencies in the lung cancer patients, resistant smokers and controls.

| Frequency | Allele* | | Genotype | | |
|---|---|---|---|---|---|
| | C | T | CC | CT | TT |
| Controls n = 183 (%) | | | | | |
| Lung Cancer n = 107 (%) | 82 (38%) | 132 (62%) | 16 (15%) | 50 (47%) | $41^1$ (38%) |
| Resistant n = 198 (%) | 166 (42%) | 228 (58%) | 31 (16%) | 104 (53%) | 62 (31%) |

*number of chromosomes (2n)

A mathematical analysis of the data in the table indicated that:
1. Genotype. TT vs CC/CT for Lung cancer vs resistant, Odds ratio (OR)=1.4, 95% confidence limits 0.8-2.3, $\chi^2$ (Yates uncorrected)=1.45, p=0.23, TT genotype=susceptibility to lung cancer.

Thus, for the −786 T/C polymorphism of the Nitric oxide synthase 3 gene, the TT genotype was found to be greater in the lung cancer cohort compared to the smoking resistant cohort (OR=1.4, P=0.23) consistent with a susceptibility role (see Table 1F).

Example 4

Super Oxide Dismutase 3 Arg 312 Gln C/G
Polymorphism Allele and Genotype Frequencies in
the Lung Cancer, Resistant Smokers and Controls The genotype frequency for the above allele was determined in lung cancer patients, resistant smokers, and controls. The frequencies are shown in the following table.

TABLE 2

Super Oxide Dismutase 3 Arg 312 Gln C/G Polymorphism Allele
And Genotype Frequencies In The Lung Cancer, Resistant Smokers And Controls.

| Frequency | Allele* | | Genotype | | |
|---|---|---|---|---|---|
| | C | G | CC | CG | GG |
| Controls n = 190 (%) | 371 (98%) | 9 (2%) | 183 (96%) | 5 (3%) | 2 (1%) |
| Lung Cancer n = 104 (%) | 208 (100%) | 0 (0%) | 104 (100%) | 0 (0%) | 0 (0%) |
| Resistant n = 182 (%) | 390 (98%) | 10 (3%) | 191 (95%) | 8[1] (4%) | 1[1] (1%) |

*number of chromosomes (2n)

A mathematical analysis of the data in the table indicated that:
1. Genotype CG/GG vs CC for resistant vs lung cancer, Yates uncorrected=3.38, P=0.07 and Fisher's Two tailed test, P=0.03. CG/GG=protective for lung cancer.

Thus, for the analysis of the Arg 312 Gln polymorphism of the Superoxide dismutase 3 gene, the CG and GG genotypes were found to be significantly greater in the smoking resistant cohort compared to the lung cancer cohort (P=0.03) consistent with each having a protective role (Table 2).

Example 5

XRCC1 Arg 399 Gln A/G Polymorphism Allele and
Genotype Frequencies in the Lung Cancer, Resistant
Smokers and Controls The genotype frequency for the above allele was determined in lung cancer patients, resistant smokers, and controls. The frequencies are shown in the following table.

TABLE 3

XRCC1 Arg 399 Gln A/G Polymorphism Allele And Genotype Frequencies
In The Lung Cancer, Resistant Smokers And Controls.

| Frequency | Allele* | | Genotype | | |
|---|---|---|---|---|---|
| | A | G | AA | AG | GG |
| Controls n = 190 (%) | | | | | |
| Lung Cancer n = 103 (%) | 68 (33%) | 138 (67%) | 4 (4%) | 60 (58%) | 39 (38%) |
| Resistant n = 193 (%) | 132 (34%) | 254 (66%) | 18[1] (9%) | 96 (50%) | 79 (41%) |

*number of chromosomes (2n)

A mathematical analysis of the data in the table indicated that:
1. Genotype. AA vs AG/GG for resistant vs lung cancer, Odds ratio (OR)=2.6, 95% confidence limits 0.8-9.2, $\chi^2$ (Yates uncorrected)=2.89, p=0.09. AA genotype=protective for lung cancer.

Thus, for the analysis of the Arg 399 Gln A/G polymorphism of the XRCC1 gene, the AA genotype was found to be greater in the smoking resistant cohort compared to the lung cancer cohort (OR=2.6, P=0.09) consistent with a protective role (Table 3).

Example 6

Interleukin 8 −251 A/T Polymorphism Allele and
Genotype Frequencies in the Lung Cancer, Resistant
Smokers and Controls The genotype frequency for the above allele was determined in lung cancer patients, resistant smokers, and controls. The frequencies are shown in the following table.

TABLE 4

Interleukin 8 −251 A/T Polymorphism Allele And Genotype Frequencies In The Lung Cancer, Resistant Smokers And Controls.

| Frequency | Allele* | | Genotype | | |
|---|---|---|---|---|---|
| | A | T | AA | AT | TT |
| Controls n = 188 (%) | 175 (47%) | 201 (53%) | 39 (21%) | 97 (52%) | 52 (28%) |
| Lung Cancer n = 90 | 68 (38%) | 112 (62%) | 6 (7%) | 56 (52%) | 28 (31%) |
| Resistant n = 199 (%) | 192[2] (48%) | 206 (52%) | 45[1] (23%) | 102 (51%) | 52 (26%) |

*number of chromosomes (2n)

A mathematical analysis of the data in the table indicated that:
1. Genotype. AA vs AT/TT for resistant vs lung cancer, Odds ratio (OR)=4.1, 95% confidence limits=1.6–11.2, $\chi^2$ (Yates corrected)=9.8, p=0.002, AA=protective for lung cancer; and
2. Allele. A vs T for resistant smokers vs lung cancer, Odds ratio (OR)=1.5, 95% confidence limits 1.0-2.2, $\chi^2$ (Yates corrected)=5.07, p=0.02 A=protective for lung cancer.

Thus, for the analysis of the −251 A/T polymorphism of Interleukin-8 gene, the AA genotype was found to be significantly greater in the smoking resistant cohort compared to the lung cancer cohort (OR=4.1, P=0.002) consistent with a protective role (Table 4). The A allele was also found to be significantly greater in the smoking resistant cohort compared to the lung cancer cohort (OR=1.5, P=0.02) consistent with a protective role (Table 4).

Example 7

Anti-Chymotrypsin Ala −15 Thr Polymorphism Allele and Genotype Frequencies in the Lung Cancer Subjects, Resistant Smokers and Controls The genotype frequency for the above allele was determined in lung cancer patients and resistant smokers. The frequencies are shown in the following table.

TABLE 5

Anti-chymotrypsin Ala-15 Thr polymorphism allele and genotype frequencies in the lung cancer subjects, resistant smokers and controls.

| Frequency | Allele* | | Genotype | | |
|---|---|---|---|---|---|
| | A | G | AA | AG | GG |
| Lung Cancer n = 108 | 99 (46%) | 117[2] (54%) | 24 (22%) | 51 (47%) | 33[1] (31%) |
| Resistant n = 196 (%) | 207 (53%) | 185 (47%) | 52 (27%) | 103 (53%) | 41 (21%) |

*number of chromosomes (2n)

A mathematical analysis of the data in the table indicated that:
1. Genotype. GG vs AA/AG for Lung cancer vs resistant, Odds ratio (OR)=1.7, 95% confidence limits=0.9-2.9, $\chi^2$ (Yates uncorrected)=3.51, p=0.06, GG=susceptibile to lung cancer; and 2. Allele. G vs A for lung cancer vs resistant smokers, Odds ratio (OR)=1.3, 95% confidence limits 0.9-1.9, $\chi^2$ (Yates uncorrected)=2.71, p=0.10, G=susceptibility to lung cancer.

Thus, for the analysis of the Ala 15 Thr polymorphism of Anti-chymotrypsin gene, the GG genotype was found to be greater in the lung cancer cohort compared to the smoking resistant cohort (OR=1.7, P=0.06) consistent with a susceptibility role (see Table 5). The G allele was found to be greater in the lung cancer cohort compared to the smoking resistant cohort (OR=1.3, P=0.1) consistent with a susceptibility role (see Table 5).

Example 8

Cyclin D1 (CCND1) A 870 G Polymorphism Allele and Genotype Frequencies in the Lung Cancer Subjects and Resistant Smokers The genotype frequency for the above allele was determined in lung cancer patients and resistant smokers. The frequencies are shown in the following table.

TABLE 6

Cyclin D1 (CCND1) A 870 G Polymorphism Allele And Genotype Frequencies In The Lung Cancer Subjects And Resistant Smokers.

| Frequency | Allele* | | Genotype | | |
|---|---|---|---|---|---|
| | A | G | AA | AG | GG |
| Lung Cancer n = 107 | 109 (51%) | 105 (49%) | 25² (23%) | 59 (55%) | 23 (21%) |
| Resistant n = 199 (%) | 188 (47%) | 210 (53%) | 45 (23%) | 98 (49%) | 56¹ (28%) |

*number of chromosomes (2n)

A mathematical analysis of the data in the table indicated that:
1. Genotype. GG vs AG/AA for Resistant vs lung cancer, Odds ratio (OR)=1.4, 95% confidence limits=0.8-2.6, $\chi^2$ (Yates uncorrected)=1.6, p=0.20, GG=protective for lung cancer; and
2. Genotype. AG/AA vs GG for Lung cancer vs resistant, Odds ratio (OR)=1.4, 95% confidence limits=0.8-2.6, $\chi^2$ (Yates uncorrected)=1.6, p=0.20, AA=susceptibility to lung cancer.

Thus, for the analysis of the A 870 G polymorphism of the Cyclin D1 gene, the GG genotype was found to be greater in the smoking resistant cohort compared to the lung cancer cohort (OR=1.4, P=0.20) consistent with a protective role (see Table 6). In contrast, the AA genotype was found to be greater in the lung cancer cohort compared to the smoking resistant cohort (OR=1.4, P=0.2) consistent with a susceptibility role (see Table 6).

Example 9

Interleukin 1B (IL-1b) −511 A/G Polymorphism Allele and Genotype Frequencies in the Lung Cancer Subjects, Resistant Smokers and Controls The genotype frequency for the above allele was determined in lung cancer patients and resistant smokers. The frequencies are shown in the following table.

TABLE 7

Interleukin 1B (IL-1b) −511 A/G Polymorphism Allele And Genotype Frequencies In The Lung Cancer Subjects, Resistant Smokers And Controls.

| Frequency | Allele* | | Genotype | | |
|---|---|---|---|---|---|
| | A | G | AA | AG | GG |
| Lung Cancer n = 107 | 64 (30%) | 150 (70%) | 12 (11%) | 40 (37%) | 55¹ (51%) |
| Resistant n = 198 (%) | 143 (36%) | 253 (64%) | 23 (12%) | 97 (49%) | 78 (39%) |

*number of chromosomes (2n)

A mathematical analysis of the data in the table indicated that:
1. Genotype. GG vs AA/AG for Lung cancer vs resistant, Odds ratio (OR)=1.6, 95% confidence limits=1-2.7, $\chi^2$ (Yates uncorrected)=4.07, p=0.04, GG=susceptibility to lung cancer.

Thus, for the analysis of the −511 A/G polymorphism of the Interleukin 1B gene, the GG genotype was found to be significantly greater in the lung cancer cohort compared to the smoking resistant cohort (OR=1.6, P=0.04) consistent with a susceptibility role (see Table 7).

Example 10

FAS (Apo-1/CD 95) A −670 G Polymorphism Allele and Genotype Frequencies in the Lung Cancer Subjects, Resistant Smokers and Controls The genotype frequency for the above allele was determined in lung cancer patients and resistant smokers. The frequencies are shown in the following table.

TABLE 8

FAS (Apo-1/CD 95) A −670 G Polymorphism Allele And Genotype Frequencies In The Lung Cancer Subjects, Resistant Smokers And Controls.

| Frequency | Allele* | | Genotype | | |
|---|---|---|---|---|---|
| | A | G | AA | AG | GG |
| Lung Cancer n = 106 | 121[2] (57%) | 91 (43%) | 32[1] (30%) | 57 (54%) | 17 (16%) |
| Resistant n = 198 (%) | 202 (51%) | 194 (49%) | 45 (23%) | 112 (57%) | 41 (21%) |

*number of chromosomes (2n)

A mathematical analysis of the data in the table indicated that:

1. Genotype. AA vs AG/GG for Lung cancer vs resistant, Odds ratio (OR)=1.5, 95% confidence limits=0.8-2.6, $\chi^2$ (Yates uncorrected)=2.03, p=0.15, AA=susceptibility to lung cancer; and
2. Allele. A vs G for Lung cancer vs resistant, Odds ratio (OR)=1.3, 95% confidence limits 0.9-1.8, $\chi^2$ (Yates uncorrected)=2.04, p=0.15, A=susceptibility to lung cancer.

Thus, for the analysis of the A −670 G polymorphism of the FAS (Apo-1/CD95) gene, the AA genotype was found to be greater in the lung cancer cohort compared to the smoking resistant cohort (OR=1.5, P=0.15) consistent with a susceptibility role (see Table 8). The A allele was found to be greater in the lung cancer cohort compared to the smoking resistant cohort (OR=1.3, P=0.15) consistent with a susceptibility role (see Table 8).

Example 11

XPD 751 T/G Polymorphism Allele and Genotype Frequencies in the Lung Cancer Subjects and Resistant Smokers The genotype frequency for the above allele was determined in lung cancer patients and resistant smokers. The frequencies are shown in the following table.

TABLE 9

XPD 751 T/G Polymorphism Allele And Genotype Frequencies In The Lung Cancer Subjects And Resistant Smokers.

| | Frequency | | | | |
|---|---|---|---|---|---|
| | Allele* | | Genotype | | |
| | G | T | GG | TG | TT |
| Lung Cancer n = 108 | 72 (33%) | 144 (66%) | 11 (10%) | 50 (46%) | 47 (44%) |

TABLE 9-continued

XPD 751 T/G Polymorphism Allele And Genotype Frequencies In The Lung Cancer Subjects And Resistant Smokers.

| | Frequency | | | | |
|---|---|---|---|---|---|
| | Allele* | | Genotype | | |
| | G | T | GG | TG | TT |
| Resistant n = 197 (%) | 147 (37%) | 247 (63%) | 31[1] (16%) | 85 (43%) | 81 (41%) |

*number of chromosomes (2n)

A mathematical analysis of the data in the table indicated that:

1. Genotype. GG vs TG/TT for Resistant vs lung cancer, Odds ratio (OR)=1.7, 95% confidence limits=0.8-3.7, $\chi^2$ (Yates uncorrected)=1.81, p=0.18, GG=protective for lung cancer.

Thus, for the analysis of the 751 T/G polymorphism of the XPD gene, the GG genotype was found to be greater in the smoking resistant cohort compared to the lung cancer cohort (OR=1.7, P=0.18) consistent with a protective role (Table 9).

Example 12

Cytochrome P450 1A1 Ile 462 Val G/A Polymorphism Allele and Genotype Frequencies in the Lung Cancer Subjects and Resistant Smokers The genotype frequency for the above allele was determined in lung cancer patients and resistant smokers. The frequencies are shown in the following table.

TABLE 10

Cytochrome P450 1A1 Ile 462 Val G/A Polymorphism Allele And Genotype
Frequencies In The Lung Cancer Subjects, Resistant Smokers And Controls.

| | Frequency | | | | |
|---|---|---|---|---|---|
| | Allele* | | Genotype | | |
| | G | A | GG | AG | AA |
| Lung Cancer n = 109 | 5 (2%) | 213 (98%) | 0 (0%) | 5 (5%) | 104[1] (95%) |
| Resistant n = 199 (%) | 20 (5%) | 378 (95%) | 13[1] (1%) | 18[1] (9%) | 180 (90%) |

*number of chromosomes (2n)

A mathematical analysis of the data in the table indicated that:

1. Genotype. AG/GG vs AA for Resistant vs lung cancer, Odds ratio (OR)=2.2, 95% confidence limits=0.7-6.9, $\chi^2$ (Yates uncorrected)=2.41, p=0.12, GG/AG=protective for lung cancer, AA=susceptibility to lung cancer.

Thus, for the analysis of the Ile 462 Val G/A polymorphism of the CYP 450 1A1 gene, the AG and GG genotypes were found to be greater in the smoking resistant cohort compared to the lung cancer cohort (OR=2.2, P=0.12) consistent with each having a protective role (see Table 10). In contrast, the AA genotype was found to be consistent with a susceptibility role (see Table 10).

Example 13

MMP12 Asn 357 Ser Polymorphism Allele and Genotype Frequencies in the Lung Cancer Subjects and Resistant Smokers The genotype frequency for the above allele was determined in lung cancer patients and resistant smokers. The frequencies are shown in the following table.

TABLE 11

MMP12 Asn 357 Ser Polymorphism Allele And Genotype
Frequencies In The Lung Cancer Subjects And Resistant Smokers.

| | Frequency | | | | |
|---|---|---|---|---|---|
| | Allele* | | Genotype | | |
| | G | A | GG | AG | AA |
| Lung Cancer n = 109 | 8 (4%) | 210 (96%) | 1 (1%) | 6 (5%) | 102 (94%) |
| Resistant n = 199 (%) | 21 (5%) | 377 (95%) | 0[1] (0%) | 21[1] (11%) | 178 (89%) |

*number of chromosomes (2n)

A mathematical analysis of the data in the table indicated that:

1. Genotype. GG/AG vs AA for Resistant vs lung cancer, Odds ratio (OR)=1.7, 95% confidence limits=0.7-4.6, $\chi^2$ (Yates uncorrected)=1.45, p=0.23, GG/AG=protective for lung cancer.

Thus, for the analysis of the Asn 357 Ser polymorphism of the Matrix metalloproteinase 12 gene, the GG and AG genotypes were found to be greater in the smoking resistant cohort compared to the lung cancer cohort (OR=1.7, P=0.23) consistent with each having a protective role (Table 11).

Example 14

8-Oxoguanine DNA Glycosylase (OGG1) Ser 326 Cys C/G Polymorphism Allele and Genotype Frequencies in the Lung Cancer Subjects and Resistant Smokers The genotype frequency for the above allele was determined in lung cancer patients and resistant smokers. The frequencies are shown in the following table.

TABLE 12

8-Oxoguanine DNA Glycosylase (OGG1) Ser 326 Cys C/G
Polymorphism Allele And Genotype Frequencies In The Lung Cancer
Subjects And Resistant Smokers.

| | Frequency | | | | |
|---|---|---|---|---|---|
| | Allele* | | Genotype | | |
| | G | C | GG | CG | CC |
| Lung Cancer n = 109 | 40 (18%) | 178 (82%) | 2 (2%) | 36 (33%) | 71 (65%) |
| Resistant n = 199 (%) | 100 (25%) | 298 (75%) | 14[1] (7%) | 72 (36%) | 113 (57%) |

*number of chromosomes (2n)

A mathematical analysis of the data in the table indicated that:

1. Genotype. GG vs CG/CC for Resistant vs lung cancer, Odds ratio (OR)=4.0, 95% confidence limits=0.9-26.3, $\chi^2$ (Yates uncorrected)=3.87, p=0.05, GG=protective for lung cancer.

Thus, for the analysis of the Ser 326 Cys (C/G) polymorphism of the OGGI gene, the GG genotype was found to be significantly greater in the smoking resistant cohort compared to the lung cancer cohort (OR=4.0, P=0.05) consistent with a protective role (Table 12).

Example 15

N-Acetyltransferase 2 Arg 197 Gln G/A Polymorphism Allele and Genotype Frequencies in the Lung Cancer Subjects and Resistant Smokers The genotype frequency for the above allele was determined in lung cancer patients and resistant smokers. The frequencies are shown in the following table.

TABLE 13

N-Acetyltransferase 2 Arg 197 Gln G/A Polymorphism Allele And Genotype Frequencies In The Lung Cancer Subjects And Resistant Smokers.

| | Frequency | | | | |
|---|---|---|---|---|---|
| | Allele* | | Genotype | | |
| | A | G | AA | AG | GG |
| Lung Cancer n = 106 | 55 (26%) | 157 (74%) | 9 (8%) | 37 (35%) | 60[1] (57%) |
| Resistant n = 195 (%) | 122 (31%) | 268 (69%) | 17 (9%) | 88 (45%) | 90 (46%) |

*number of chromosomes (2n)

A mathematical analysis of the data in the table indicated that:
1. Genotype. GG vs AG/AA for Lung cancer vs resistant, Odds ratio (OR)=1.5, 95% confidence limits=0.9-2.5, $\chi^2$ (Yates uncorrected)=3.0, p=0.08, GG=susceptibility to lung cancer.

Thus, for the analysis of the Arg 197 Gln G/A polymorphism of the N-Acetyltransferase 2 gene, the GG genotype was found to be greater in the lung cancer cohort compared to the smoking resistant cohort (OR=1.5, P=0.08) consistent with a susceptibility role (see Table 13).

Example 16

Cytochrome P450 2E1 1019 G/C Pst1 Polymorphism Allele and Genotype Frequencies in the Lung Cancer Subjects and Resistant Smokers The genotype frequency for the above allele was determined in lung cancer patients and resistant smokers. The frequencies are shown in the following table.

TABLE 14a

Cytochrome P450 2E1 1019 G/C Pst1 Polymorphism Allele And Genotype Frequencies In The Lung Cancer Subjects And Resistant Smokers.

| | Frequency | | | | |
|---|---|---|---|---|---|
| | Allele* | | Genotype | | |
| | C | G | CC | CG | GG |
| Lung Cancer n = 109 | 10 (5%) | 208 (95%) | 0 (0%) | 10[1] (9%) | 99 (91%) |
| Resistant n = 197 (%) | 11 (3%) | 383 (97%) | 0 (0%) | 11 (6%) | 186 (94%) |

*number of chromosomes (2n)

A mathematical analysis of the data in the table indicated that:
1. Genotype. CG vs GG for Lung cancer and resistant, Odds ratio (OR)=1.7, 95% confidence limits=0.7-4.5, $\chi^2$ (Yates uncorrected)=1.42, p=0.23, CG=susceptibility to lung cancer.

Thus, for the analysis of the 1019 G/C Pst 1 polymorphism of the CYP 2E1 gene, the CG genotype was found to be greater in the lung cancer cohort compared to the smoking resistant cohort (OR=1.7, P=0.23) consistent with a susceptibility role (see Table 14a).

Example 17

Cytochrome P450 2E1 C/T Rsa I Polymorphism Allele and Genotype Frequencies in the Lung Cancer Subjects and Resistant Smokers The genotype frequency for the above allele was determined in lung cancer patients and resistant smokers. The frequencies are shown in the following table.

TABLE 14b

Cytochrome P450 2E1 C/T Rsa I Polymorphism Allele And Genotype Frequencies In The Lung Cancer Subjects And Resistant Smokers.

| | Frequency | | | | |
|---|---|---|---|---|---|
| | Allele* | | Genotype | | |
| | T | C | TT | TC | CC |
| Lung Cancer n = 108 | 11 (5%) | 205 (95%) | 0 (0%) | 11[1] (10%) | 97 (90%) |
| Resistant n = 198 (%) | 11 (3%) | 385 (97%) | 0 (0%) | 11 (6%) | 187 (94%) |

*number of chromosomes (2n)

A mathematical analysis of the data in the table indicated that:
1. Genotype. TC vs CC for Lung cancer and resistant, Odds ratio (OR)=1.9, 95% confidence limits=0.8-5.0, $\chi^2$ (Yates uncorrected)=2.24, p=0.13, TC=susceptibility to lung cancer.

Thus, for the analysis of the C/T Rsa 1 polymorphism of the CYP 2E1 gene, the TC genotype was found to be greater in the lung cancer cohort compared to the smoking resistant cohort (OR=1.9, P=0.13) consistent with a susceptibility role (see Table 14b).

Example 18

Interleukin 18 105 A/C Polymorphism Allele and Genotype Frequencies in the Lung Cancer Subjects and Resistant Smokers The genotype frequency for the above allele was determined in lung cancer patients and resistant smokers. The frequencies are shown in the following table.

TABLE 15a

Interleukin 18 105 A/C Polymorphism Allele And Genotype Frequencies In The Lung Cancer Subjects And Resistant Smokers.

| | Frequency | | | | |
|---|---|---|---|---|---|
| | Allele* | | Genotype | | |
| | C | A | CC | AC | AA |
| Lung Cancer n = 107 | 50 (23%) | 164 (77%) | 8 (8%) | 34 (33%) | 65[1] (61%) |
| Resistant n = 200 (%) | 116 (29%) | 284 (71%) | 17[1] (9%) | 82[1] (41%) | 101 (50%) |

*number of chromosomes (2n)

A mathematical analysis of the data in the table indicated that:
1. Genotype. AA vs AC/CC for Lung cancer and resistant, Odds ratio (OR)=1.6, 95% confidence limits=1.0-2.6, $\chi^2$ (Yates uncorrected)=3.51, p=0.06, AA=susceptibility to lung cancer, AC/CC=protective for lung cancer Thus, for the analysis of the 105 A/C polymorphism of the Interleukin-18 gene, the AA genotype was found to be greater in the lung cancer cohort compared to the smoking resistant cohort (OR=1.6, P=0.06) consistent with a susceptibility role (see Table 15a). In contrast, the AC and CC genotypes were each consistent with a protective role (see Table 15).

Example 19

Interleukin 18–133 C/G Polymorphism Allele and Genotype Frequencies in the Lung Cancer Subjects and Resistant Smokers The genotype frequency for the above allele was determined in lung cancer patients and resistant smokers. The frequencies are shown in the following table.

TABLE 15b

Interleukin 18 –133 C/G Polymorphism Allele And Genotype Frequencies In The Lung Cancer Subjects And Resistant Smokers.

| | Frequency | | | | |
|---|---|---|---|---|---|
| | Allele* | | Genotype | | |
| | G | C | GG | CG | CC |
| Lung Cancer n = 109 | 52 (24%) | 166 (76%) | 8 (7%) | 36 (33%) | 65[1] (60%) |
| Resistant n = 198 (%) | 117 (30%) | 279 (70%) | 17[1] (9%) | 83[1] (42%) | 98 (49%) |

*number of chromosomes (2n)

A mathematical analysis of the data in the table indicated that:

1. Genotype. CC vs CG/GG for Lung cancer and resistant, Odds ratio (OR)=1.5, 95% confidence limits=0.9-2.5, $\chi^2$ (Yates uncorrected)=2.90, p=0.09, CC=susceptibility to lung cancer, CG/GG=protective for lung cancer.

Thus, for the analysis of the −1.33 C/G polymorphism of the Interleukin-18 gene, the CC genotype was found to be greater in the lung cancer cohort compared to the smoking resistant cohort (OR=1.5, P=0.09) consistent with a susceptibility role (see Table 15b). In contrast, the CG and GG genotypes were each consistent with a protective role (see Table 15b).

Example 20

Glutathione S-Transferase M Null Polymorphism Allele and Genotype Frequencies in the Lung Cancer Subjects, Controls, and Resistant Smokers The genotype frequency for the above allele was determined in lung cancer patients and resistant smokers. The frequencies are shown in the following table.

TABLE 16

Glutathione S-Transferase M Null Polymorphism Allele And Genotype Frequencies In The Lung Cancer Subjects, Controls, And Resistant Smokers.

| | Allele* | |
|---|---|---|
| Frequency | Null | Wild |
| Controls n = 178 | 75 (42%) | 103 (58%) |
| Lung Cancer n = 107 | 67[1] (58%) | 48 (42%) |
| Resistant n = 182 | 100 (55%) | 82 (45%) |

*number of chromosomes (2n)

A mathematical analysis of the data in the table indicated that:

1. Genotype. Null vs wild for Lung cancer and controls, Odds ratio (OR)=1.92, 95% confidence limits=1.2-3.2, $\chi^2$ (Yates corrected)=6.64, p=0.01, Null=susceptibility to lung cancer.

Thus, for the analysis of the null polymorphism of the Glutathione S Transferase gene, the null genotype was found to be greater in the lung cancer cohort compared to the blood donor cohort (OR=1.92, P=0.01) consistent with a susceptibility role (see Table 16).

Example 21

Interferon-Gamma 874 A/T Polymorphism Allele and Genotype Frequencies in the Lung Cancer Subjects, Resistant Smokers and Controls The genotype frequency for the above allele was determined in lung cancer patients and resistant smokers. The frequencies are shown in the following table.

TABLE 17

Interferon-Gamma 874 A/T Polymorphism Allele And Genotype Frequencies In The Lung Cancer Subjects, Resistant Smokers And Controls.

| | Frequency | | | | |
|---|---|---|---|---|---|
| | Allele* | | Genotype | | |
| | A | T | AA | AT | TT |
| Controls n = 186 (%) | 183 (49%) | 189 (51%) | 37 (20%) | 109 (58%) | 40 (22%) |
| Lung cancer n = 106 (%) | 116 (55%) | 96 (45%) | 34[1,2] (32%) | 48 (45%) | 24 (23%) |
| Resistant n = 196 (%) | 209 (53%) | 183 (47%) | 50 (26%) | 109 (56%) | 37 (19%) |

*number of chromosomes (2n)

A mathematical analysis of the data in the table indicated that:
1. Genotype. AA vs AT/TT for lung cancer vs resistant, Odds ratio (OR)=1.4, 95% confidence limits 0.8-2.4, $\chi^2$ (Yates uncorrected)=1.48, p=0.22, AA genotype=susceptibile to lung cancer; and
2. Genotype. AA vs AT/TT for lung cancer vs controls, Odds ratio (OR)=1.9, 95% confidence limits 1.1-3.4, $\chi^2$ (Yates corrected)=5.45, p=0.02, AA genotype=susceptibile to lung cancer.

Thus, for the analysis of the 874 A/T polymorphism of the Interferon gamma gene, the AA genotype was found to be greater in the lung cancer cohort compared to the blood donor cohort (OR=1.9, P=0.02) and compared to the smoking resistant cohort (OR=1.4, P=0.22) consistent with a susceptibility role (see Table 17).

Example 22

Cyclo-Oxygenase 2 Polymorphism Allele and Genotype Frequency in the Lung Cancer Patients, Exposed Resistant Smokers and Controls The genotype frequency for the above allele was determined in lung cancer patients and resistant smokers. The frequencies are shown in the following table.

TABLE 18

Cyclo-Oxygenase 2 Polymorphism Allele And Genotype Frequency In The Lung Cancer Patients, Exposed Resistant Smokers And Controls.

| Frequency | Allele* | | Genotype | | |
|---|---|---|---|---|---|
| | C | G | CC | CG | GG |
| Controls n = 95 (%) | 27 (14%) | 161 (86%) | 3 (3%) | 21 (22%) | 70 (75%) |
| Lung Cancer n = 109 (%) | 34 (16%) | 184 (84%) | 5 (5%) | 24 (22%) | 80 (73%) |
| Resistant n = 158 (%) | 75 (24%) | 241 (76%) | 11 (7%) | 53 (34%) | 94 (59%) |

*number of chromosomes (2n)

A mathematical analysis of the data in the table indicated that:
1. Genotype. CC/CG vs GG for Lung cancer vs resistant, Odds ratio (OR)=0.53, 95% confidence limits=0.3-0.9, $\chi^2$ (Yates corrected)=4.9, p=0.03 CC/CG=protective;
2. Allele. C vs G for Lung cancer vs resistant, Odds ratio (OR)=0.59, 95% confidence limits 0.4-0.9, $\chi^2$ (Yates corrected)=4.8, p=0.03, C=protective;
3. Genotype. GG vs CG/CC for Lung cancer vs resistant, Odds ratio (OR)=1.88, 95% confidence limits=1.1-3.3, $\chi^2$ (Yates corrected)=4.9, p=0.03 GG=susceptibility; and
4. Allele. G vs C for Lung cancer vs resistant, Odds ratio (OR)=1.7, 95% confidence limits 1.1-2.7, $\chi^2$ (Yates corrected)=4.8, p=0.03, G=susceptibility.

Thus, for the analysis of the −765 C/G promoter polymorphisms of the cyclo-oxygenase 2 gene, the C allele, and CC and CG genotypes were found to be significantly greater in the resistant smoker cohort compared to the lung cancer cohort (OR=0.59, P=0.03 and OR=0.53, P=0.03, respectively), consistent with a protective role. This greater frequency compared to the blood donor cohort also suggests that the C allele (CC genotype) is over-represented in the resistant group (see Table 18). In contrast, the G allele and GG genotype were found to be greater in the lung cancer cohort compared to the smoking resistant cohort (OR=1.7, P=0.03 and OR=1.88, P=0.03, respectively), consistent with a susceptibility role (see Table 18).

Example 23

Matrix Metalloproteinase 1 (MMP1) −1607 1G/2G Polymorphism Allele and Genotype Frequencies in Lung Cancer Patients, Exposed Resistant Smokers and Controls The genotype frequency for the above allele was determined in lung cancer patients and resistant smokers. The frequencies are shown in the following table.

TABLE 19

Matrix Metalloproteinase 1 (MMP1) −1607 1G/2G Polymorphism Allele And Genotype Frequencies In Lung Cancer Patients, Exposed Resistant Smokers And Controls.

| Frequency | Allele* | | Genotype | | |
|---|---|---|---|---|---|
| | 1G | 2G | 1G1G | 1G2G | 2G2G |
| Controls n = 174 (%) | 214 (61%) | 134 (39%) | 68 (39%) | 78 (45%) | 28 (16%) |
| Lung Cancer n = 67 (%) | 58 (43%) | 76 (57%) | 13 (19%) | 32 (48%) | 22 (33%) |
| Resistant n = 171 (%) | 167 (49%) | 175 (51%) | 41 (24%) | 85 (50%) | 45 (26%) |

*number of chromosomes (2n)

A mathematical analysis of the data in the table indicated that:
1. Genotype. 2G2G vs 1G1G/1G2G for Lung cancer vs controls, Odds ratio (OR)=2.58, 95% confidence limits 1.3-5.2, $\chi^2$ (Yates uncorrected)=7.5, p=0.006 2G2G genotype=susceptibility; and
2. Allele. 2G vs 1G for Lung cancer vs controls, Odds ratio (OR)=2.1, 95% confidence limits 1.4-3.2, $\chi^2$ (Yates corrected)=12.3, p=0.0004, 2G=susceptibility.

Thus, for the analysis of the −1607 1G/2G polymorphisms of the Matrix metalloproteteinase 1 gene, the 2G2G genotype was found to be significantly greater in the lung cancer cohort compared to the blood donor cohort (OR=2.58, P=0.006), consistent with a susceptibility role (see Table 19). The 2G allele was found to be significantly greater than the lung cancer cohort compared to the blood donor cohort (OR=2.1, P=0.0004), consistent with a susceptibility role (see Table 19).

Example 24

Connective Tissue Growth Factor (CTGF) −447 G/C Polymorphism Allele and Genotype Frequencies in the Lung Cancer And Resistant Smokers The genotype frequency for the above allele was determined in lung cancer patients and resistant smokers. The frequencies are shown in the following table.

TABLE 20

Connective Tissue Growth Factor (CTGF) −447 G/C Polymorphism Allele And Genotype Frequencies In The Lung Cancer And Resistant Smokers.

| Frequency | Allele* | | Genotype | | |
|---|---|---|---|---|---|
| | G | C | GG | GC | CC |
| Lung cancer n = 109 (%) | 201 (92%) | 17 (8%) | 92 (84%) | 17 (16%) | 0 (0%) |
| Resistant n = 200 (%) | 379 (95%) | 21 (5%) | 179 (90%) | 21 (10%) | 0 (0%) |

*number of chromosomes (2n)

A mathematical analysis of the data in the table indicated that:
1. Genotype. GC/CC vs GG for lung cancer vs resistant, Odds ratio (OR)=1.6, 95% confidence limits 0.8-3.3, $\chi^2$ (Yates uncorrected)=1.70, p=0.19, GC/CC genotype=susceptibility (trend).

Thus, for the analysis of the −447 G/C polymorphism of the connective tissue growth factor gene, the CC and GC genotypes were found to be greater in the lung cancer cohort compared to the smoking resistant cohort (OR=1.6, P=0.19) consistent with a susceptibility role (see Table 20).

Example 25

Mucin 5AC (Muc5AC) −221 C/T Polymorphism Allele and Genotype Frequencies in the Lung Cancer and Resistant Smokers The genotype frequency for the above allele was determined in lung cancer patients and resistant smokers. The frequencies are shown in the following table.

TABLE 21

Mucin 5AC (Muc5AC) −221 C/T Polymorphism Allele And Genotype Frequencies In The Lung Cancer And Resistant Smokers.

| Frequency | Allele* | | Genotype | | |
|---|---|---|---|---|---|
| | C | T | CC | CT | TT |
| Lung cancer n = 109 (%) | 177 (81%) | 41 (19%) | 73 (67%) | 31 (28%) | 5 (5%) |
| Resistant n = 195 (%) | 296 (76%) | 94 (24%) | 119 (61%) | 58 (30%) | 18 (9%) |

*number of chromosomes (2n)

A mathematical analysis of the data in the table indicated that:
1. Genotype. TT vs CC/CT for lung cancer vs resistant, Odds ratio (OR)=0.47, 95% confidence limits 0.2-1.4, $\chi^2$ (Yates uncorrected)=2.16, p=0.14, TT genotype=protective (trend).

Thus, for the analysis of the −221 C/T polymorphism in the Mucin 5AC gene the TT genotype was found to be greater in the resistant smoker cohort compared to the lung cancer cohort (OR=0.47, P=0.14) consistent with a protective role (see Table 21).

Example 26

Mannose Binding Lectin (MBL2) 161 G/A Polymorphism Allele and Genotype Frequencies in the Lung Cancer and Resistant Smokers The genotype frequency for the above allele was determined in lung cancer patients and resistant smokers. The frequencies are shown in the following table.

TABLE 22

Mannose Binding Lectin (MBL2) 161 G/A Polymorphism Allele And Genotype Frequencies In The Lung Cancer And Resistant Smokers.

| Frequency | Allele* | | Genotype | | |
|---|---|---|---|---|---|
| | G | A | GG | AG | AA |
| Lung cancer n = 105 (%) | 173 (82%) | 37 (18%) | 71 (67%) | 31 (30%) | 3 (3%) |
| Resistant n = 197 (%) | 338 (86%) | 56 (14%) | 147 (75%) | 44 (22%) | 6 (3%) |

*number of chromosomes (2n)

A mathematical analysis of the data in the table indicated that:
1. Genotype. AG/AA vs GG for lung cancer vs resistant, Odds ratio (OR)=1.4, 95% confidence limits 0.8-2.4, $\chi^2$ (Yates uncorrected)=1.67, p=0.20, AG/AA genotype=susceptibility (trend).

Thus, for the analysis of the 161 G/A polymorphism of the Mannose binding lectin (MBL2) gene, the AA and AG genotypes were found to be greater in the lung cancer cohort compared to the resistant smoker cohort (OR=1.4, P=0.20) consistent with each having a susceptibility role (see Table 22).

Example 27

Nibrin (NBS1) Gln185Glu G/C Polymorphism Allele and Genotype Frequencies in the Lung Cancer and Resistant Smokers The genotype frequency for the above allele was determined in lung cancer patients and resistant smokers. The frequencies are shown in the following table.

TABLE 23

Nibrin (NBS1) Gln185Glu G/C Polymorphism Allele And Genotype Frequencies In The Lung Cancer And Resistant Smokers.

| Frequency | Allele* | | Genotype | | |
|---|---|---|---|---|---|
| | G | C | GG | GC | CC |
| Lung cancer n = 109 (%) | 150 (69%) | 68 (31%) | 54 (50%) | 42 (39%) | 13 (12%) |
| Resistant n = 199 (%) | 295 (74%) | 103 (26%) | 107 (54%) | 81 (41%) | 11 (6%) |

*number of chromosomes (2n)

A mathematical analysis of the data in the table indicated that:
1. Genotype. CC vs CG/GG for lung cancer vs resistant, Odds ratio (OR)=2.3, 95% confidence limits 0.9-5.8, $\chi^2$ (Yates uncorrected)=4.01, p=0.05, CC genotype=susceptibility.

Thus, for the analysis of the Gln 185 Glu G/C polymorphism of the Nibrin gene, the CC genotype was found to be significantly greater in the lung cancer cohort compared to the resistant smoker cohort (OR=2.3, P=0.05), consistent with a susceptibility role (see Table 23).

Example 28

Arginase 1 (Arg1) Intron 1 C/T Polymorphism Allele and Genotype Frequencies in the Lung Cancer and Resistant Smokers The genotype frequency for, the above allele was determined in lung cancer patients and resistant smokers. The frequencies are shown in the following table.

TABLE 24

Arginase 1 (Arg1) Intron 1 C/T Polymorphism Allele And Genotype Frequencies In The Lung Cancer And Resistant Smokers.

| Frequency | Allele* | | Genotype | | |
|---|---|---|---|---|---|
| | C | T | CC | CT | TT |
| Lung cancer n = 105 (%) | 137 (65%) | 73 (35%) | 45 (43%) | 47 (45%) | 13 (12%) |
| Resistant n = 180 (%) | 203 (56%) | 157 (44%) | 65 (36%) | 73 (41%) | 42 (23%) |

*number of chromosomes (2n)

A mathematical analysis of the data in the table indicated that:

1. Genotype. TT vs CC/CT for lung cancer vs resistant, Odds ratio (OR)=0.46, 95% confidence limits 0.2-0.95, $\chi^2$ (Yates uncorrected)=5.11, p=0.02, TT genotype=protective; and
2. Allele. T vs C for lung cancer vs resistant, Odds ratio (OR)=0.69, 95% confidence limits 0.5-1.0, $\chi^2$ (Yates corrected)=3.96, p=0.05, T allele=protective.

Thus, for the analysis of the intron 1 C/T polymorphism of the Arginase 1 gene, the TT genotype was found to be significantly greater in the resistant smoker cohort compared to the lung cancer cohort (OR=0.46, P=0.02) consistent with a protective role (see Table 24). The T allele was found to be significantly greater in the resistant smoker cohort compared to the lung cancer cohort (OR=0.69, P=0.05) consistent with a protective role (see Table 24).

Example 29

REV1 Phe257Ser C/T Polymorphism Allele and Genotype Frequencies in the Lung Cancer and Resistant Smokers The genotype frequency for the above allele was determined in lung cancer patients and resistant smokers. The frequencies are shown in the following table.

TABLE 25

REV1 Phe257Ser C/T Polymorphism Allele And Genotype Frequencies In The Lung Cancer And Resistant Smokers.

| Frequency | Allele* | | Genotype | | |
|---|---|---|---|---|---|
| | C | T | CC | CT | TT |
| Lung cancer n = 109 (%) | 129 (59%) | 89 (41%) | 39 (36%) | 51 (47%) | 19 (17%) |
| Resistant n = 192 (%) | 242 (63%) | 142 (37%) | 83 (43%) | 76 (40%) | 33 (17%) |

*number of chromosomes (2n)

A mathematical analysis of the data in the table indicated that:

1. Genotype. CC vs CT/TT for lung cancer vs resistant, Odds ratio (OR)=0.73, 95% confidence limits 0.4-1.2, $\chi^2$ (Yates uncorrected)=1.6, p=0.20, CC genotype=protective (trend).

Thus, for the analysis of the Phe 257 Ser C/T polymorphism of the REV1 gene, the CC genotype was found to be greater in the resistant smoker cohort compared to the lung cancer cohort (OR=0.73, P=0.20), consistent with a protective role (see Table 25).

Example 30

Insulin-Like Growth Factor II Receptor (IGF2R) Leu252Val C/G Polymorphism Allele and Genotype Frequencies in the Lung Cancer and Resistant Smokers The genotype frequency for the above allele was determined in lung cancer patients and resistant smokers. The frequencies are shown in the following table.

TABLE 26

Insulin-Like Growth Factor II Receptor (IGF2R) Leu252Val C/G Polymorphism Allele And Genotype Frequencies In The Lung Cancer And Resistant Smokers.

| Frequency | Allele* | | Genotype | | |
|---|---|---|---|---|---|
| | C | G | CC | CG | GG |
| Lung cancer n = 109 (%) | 190 (87%) | 28 (13%) | 82 (75%) | 26 (24%) | 1 (1%) |
| Resistant n = 198 (%) | 342 (86%) | 54 (14%) | 150 (76%) | 42 (21%) | 6 (3%) |

*number of chromosomes (2n)

A mathematical analysis of the data in the table indicated that:

1. Genotype. GG vs CC/CG for lung cancer vs resistant, Odds ratio (OR)=0.30, 95% confidence limits 0.01-2.5, $\chi^2$ (Yates uncorrected)=1.41, p=0.22 (1-tailed t-test), GG genotype=protective (trend).

Thus, for the analysis of the Leu 252 Val C/G polymorphism of the Insulin-like growth factor II receptor gene the GG genotype was found to be greater in the resistant smoker cohort compared to the lung cancer cohort (OR=0.30, P=0.22) consistent with a protective role (see Table 26).

Example 31

Apex Nuclease (APE1) Asp148Glu T/G Polymorphism Allele and Genotype Frequencies in the Lung Cancer and Resistant Smokers The genotype frequency for the above allele was determined in lung cancer patients and resistant smokers. The frequencies are shown in the following table.

TABLE 27

Apex Nuclease (APE1) Asp148Glu T/G Polymorphism Allele And Genotype Frequencies In The Lung Cancer And Resistant Smokers.

| Frequency | Allele* | | Genotype | | |
|---|---|---|---|---|---|
| | T | G | TT | TG | GG |
| Lung cancer n = 109 (%) | 124 (57%) | 94 (43%) | 39 (36%) | 46 (42%) | 24 (22%) |
| Resistant n = 192 (%) | 229 (60%) | 155 (40%) | 69 (36%) | 91 (47%) | 32 (17%) |

*number of chromosomes (2n)

A mathematical analysis of the data in the table indicated that:
1. Genotype. GG vs TT/TG for lung cancer vs resistant, Odds ratio (OR)=1.4, 95% confidence limits 0.8-2.7, $\chi^2$ (Yates uncorrected)=1.3, p=0.25, GG genotype=susceptibility (trend).

Thus, for the analysis of the Asp 148 Glu T/G polymorphism of the Apex nuclease gene, the GG genotype was found to be greater in the lung cancer cohort compared to the resistant smoker cohort (OR=1.4, P=0.25), consistent with a susceptibility role (see Table 27).

Example 32

Interleukin 10 (IL-10) −1082 A/G Polymorphism Allele and Genotype Frequencies in the Lung Cancer and Resistant Smokers The genotype frequency for the above allele was determined in lung cancer patients and resistant smokers. The frequencies are shown in the following table.

TABLE 28

Interleukin 10 (IL-10) −1082 A/G Polymorphism Allele And Genotype Frequencies In The Lung Cancer And Resistant Smokers.

| Frequency | Allele* | | Genotype | | |
|---|---|---|---|---|---|
| | G | C | GG | GC | CC |
| Lung cancer n = 98 (%) | 91 (46%) | 105 (54%) | 16 (16%) | 59 (60%) | 23 (24%) |
| Resistant n = 196 (%) | 174 (44%) | 218 (56%) | 40 (20%) | 94 (48%) | 62 (32%) |

*number of chromosomes (2n)

A mathematical analysis of the data in the table indicated that:
1. Genotype. GG vs GC/CC for lung cancer vs resistant, Odds ratio (OR)=0.66, 95% confidence limits 0.4-1.2, $\chi^2$ (Yates uncorrected)=2.12, p=0.15, GG genotype=protective (trend).

Thus, for the analysis of the −108 2A/G polymorphism of the Interleukin-10 gene the GG genotype was found to be greater in the resistant smoker cohort compared to the lung cancer cohort (OR=0.66, P=0.15), consistent with a protective role (see Table 28).

Table 29 presents a summary of the above results.

TABLE 29

Summary Of Protective And Susceptibility Polymorphisms In Lung Cancer Patients Relative To Resistant Smokers (With Normal Lung Function)

| Gene | Polymorphism | Role |
|---|---|---|
| Nitric Oxide synthase 3 (NOS3) | NOS3 Asp 298 Glu | TT protective |
| Nitric Oxide synthase 3 (NOS3) | NOS3 −786 T/C | TT susceptibility |
| Superoxide dismutase 3 (SOD3) | SOD3 Arg 312 Gln | CG/GG protective |
| XRCC1 | XRCC1 Arg 399 Gln G/A | AA protective |
| Interleukin-8 (IL-8) | IL-8 −251 A/T | AA protective |
| Anti-chymotrypsin (ACT) | ACT Ala 15 Thr | GG susceptibility |
| Cyclin D (CCND1) | CCND1 A870G | GG protective AA susceptibility |
| Interleukin 1B (IL-1B) | IL-1B −511 A/G | GG susceptibility |
| FAS (Apo-1/CD95) | FAS A-670G | AA susceptibility |
| XPD | XPD −751 G/T | GG protective |
| CYP 1A1 | CYP 1A1 Ile 462 Val A/G | GG/AG protective AA susceptibility |
| Matrix metalloproteinase 12 (MMP12) | MMP12 Asn 357 Ser A/G | GG/AG protective |
| 8-Oxoguanine DNA glycolase (OGG1) | OGG1 Ser 326 Cys G/C | GG protective |
| N-acetyltransferase 2 (NAT2) | NAT2 Arg 197 Gln A/G | GG susceptibility |
| CYP2E1 | CYP2E1 1019 G/C Pst I | CC/CG susceptibility |
| CYP2E1 | CYP2E1 C/T Rsa I | TT/TC susceptibility |
| Interleukin-18 (IL-18) | IL-18 105 A/C | AC/CC protective AA susceptibility |
| Interleukin-18 (IL-18) | IL-18 −133 G/C | CG/GG protective CC susceptibility |
| Glutathione S-transferase M | GSTM null | Null susceptibility |
| Interferon gamma (IFNγ) | IFNγ 874 A/T | AA susceptibility |
| Cyclo-oxygenase 2 (COX2) | COX2 −765 G/C | CC/CG protective GG susceptibility |
| Matrix metalloproteinase 1 (MMP1) | MMP −1607 1G/2G | 2G2G susceptibility |
| Connective tissue growth factor (CTGF) | CTGF −447 G/C | GC/CC susceptibility |
| Mucin 5AC (MUC5AC) | MUC5AC −221 C/T | TT protective |
| Mannose binding lectin 2 (MBL2) | MBL2 +161 G/A | AG/AA susceptibility |
| Nibrin (NBS1) | NBS1 Gln185Glu G/C | CC susceptibility |
| Arginase 1 (Arg1) | Arg1 intron 1 C/T | TT protective |
| REV1 | REV1 Phe257Ser C/T | CC protective |

TABLE 29-continued

Summary Of Protective And Susceptibility Polymorphisms In
Lung Cancer Patients Relative To Resistant Smokers
(With Normal Lung Function)

| Gene | Polymorphism | Role |
|---|---|---|
| Insulin-like growth factor II receptor (IGF2R) | IGF2R Leu252Val C/G | GG protective |
| Apex nuclease (Apex or APE1)) | Apex Asp148Glu G/T | GG susceptibility |
| Interleukin 10 (IL-10) | IL-10 −1082 A/G | GG protective |

Example 33

In addition to examining the individual frequencies, the combined frequencies of the presence or absence of protective genotypes was also examined. The results are shown in Tables 31-35 and are discussed below.

TABLE 30

Combined Frequencies Of The Presence Or Absence Of
Protective Genotypes (CYP1A1 GG/AG, OGG1 GG, CCND1 GG,
NOS3 298 TT, IL-8 AA, XRCC1 AA) In The Exposed Smoking Subjects
(Lung Cancer Subjects And Resistant Smokers).

| Cohorts | Number of protective polymorphisms | | | Total |
|---|---|---|---|---|
| | 0 | 1 | ≥2 | |
| Lung Cancer | 66 (61%) | 37 (34%) | 6 (6%) | 109 |
| Resistant smokers | 71 (36%) | 86 (43%) | 42 (21%) | 199 |
| % of smokers with Lung cancer | 66/137 (48%) | 37/123 (30%) | 6/42 (14%) | |

| Comparison | Odd's ratio | 95% CI | $\chi^2$ | P value |
|---|---|---|---|---|
| 0 vs 1 vs 2+, Resist vs Lung cancer | — | — | 22.3 | <0.0001 |
| 2+ vs 0-1, Resist vs Lung cancer | 4.6 | 1.8-12.5 | 11.87 | 0.0005 |
| 0 vs 2+, Lung cancer vs Resist | 2.8 | 1.7-4.6 | 16.7 | <0.0001 |

When the frequencies of resistant smokers and smokers with lung cancer were compared according to the presence of 0, 1 and 2+ protective genotypes selected from a subset of six of the protective genotypes (CYP1A1GG/AG, OGG1 GG, CCND1 GG, NOS3 298 TT, IL-8 AA, XRCC1 AA), significant differences were found (overall $\gamma 2=22.3$, P<0.0001) (see Table 30). This analysis suggests smokers with 2+ protective genotypes had 4-5 times more likelihood of being resistant (OR=4.6, P=0.0005), while those with no protective genotypes were nearly three times as likely to have lung cancer (OR=2.8, P<0.0001). Examined another way, the chance of having lung cancer diminished from 48%, to 30%, to 14%, in smokers with 0, 1, or 2+ protective genotypes, respectively. Analyses of larger groups of protective polymorphisms resulted in similar findings (see Tables 32 and 34).

From the analyses of the individual polymorphisms, 19 possible susceptibility genotypes were identified and analysed for their frequencies in the smoker cohort consisting of resistant smokers and those with lung cancer. When the frequencies of resistant smokers and smokers with lung cancer were compared according to the presence of 0, 1 and 2+ susceptibility genotypes selected from a subset of six of the susceptibility genotypes (CYP2E1 1019 CC/CG, FAS AA, IL-1B GG, ACT 15 GG genotypes) significant differences were found (overall $\gamma 2=10.2$, P=0.006) (see Table 31). This analysis suggests that smokers with 2+ susceptibility genotypes had nearly two times more likelihood of having lung cancer (OR=1.8, P=0.04), while those with no susceptibility genotypes were two fold as likely to be resistant (OR=2.3, P=0.004). Examined another way, the chances of having lung cancer increased from 23%, to 38%, to 45% in smokers with 0, 1 or 2+ susceptibility genotypes, respectively. Analyses of larger groups of susceptibility polymorphisms resulted in similar findings (see Tables 33 and 35).

TABLE 31

Combined Frequencies Of The Presence Or Absence Of Susceptibility Genotypes (CYP2E1 1019 CC/CG, FAS AA, IL-1B GG, ACT 15 GG) In The Exposed Smoking Subjects (Lung Cancer Subjects And Resistant Smokers).

| Cohorts | Number of susceptibility polymorphisms | | | Total |
|---|---|---|---|---|
| | 0 | 1 | ≧2 | |
| Lung Cancer | 21 (19%) | 52 (48%) | 35 (33%) | 108 |
| Resistant smokers | 71 (36%) | 85 (43%) | 42 (21%) | 198 |
| % of smokers with lung cancer | 21/92 (23%) | 52/137 (38%) | 35/77 (45%) | |

| Comparison | Odd's ratio | 95% CI | $\chi^2$ | P value |
|---|---|---|---|---|
| 0 vs 1 vs 2+, Lung cancer vs Resist | — | — | 10.2 | 0.006 |
| 2+ vs 0-1, Lung cancer vs Resist | 1.8 | 1.0-3.1 | 4.1 | 0.04 |
| 0+ vs 1-2+, Resist vs Lung cancer | 2.3 | 1.3-4.2 | 8.2 | 0.004 |

TABLE 32

Combined Frequencies Of The Presence Or Absence Of Protective Genotypes (CYP1A1 GG/AG, OGG1 GG, CCND1 GG, NOS3 298 TT, SOD3 CG/GG, XPD GG, MMP12 GG/AG, XRCC1 AA, N = 8) In The Exposed Smoking Subjects (Lung Cancer Subjects And Resistant Smokers).

| Cohorts | Number of protective polymorphisms n = 8 | | | Total |
|---|---|---|---|---|
| | 0 | 1 | ≧2 | |
| Lung Cancer | 54 (50%) | 50 (46%) | 5 (4%) | 109 |
| Resistant smokers | 67 (34%) | 83 (42%) | 50 (25%) | 199 |
| % of smokers with Lung cancer | 54/121 (45%) | 50/133 (38%) | 5/55 (9%) | |

| Comparison | Odd's ratio | 95% CI | $\chi^2$ | P value |
|---|---|---|---|---|
| 0 vs 1 vs 2+, Resist vs Lungcancer | — | — | 21.5 | <0.0001 |
| 2+ vs 0-1, Resist vs Lung cancer | 6.9 | 2.5-20.5 | 18.7 | <0.0001 |
| 0 vs 2+, Lung cancer vs Resist | 2.0 | 1.2-3.2 | 6.96 | 0.008 |

TABLE 33

Combined Frequencies Of The Presence Or Absence Of Susceptibility Genotypes (CYP2E1 1019 CC/CG, FAS AA, IL-1B GG, ACT 15 GG, NAT2 GG, IL-18 105 AA, Ifnγ AA, N = 7) In The Exposed Smoking Subjects (Lung Cancer Subjects And Resistant Smokers).

| Cohorts | Number of susceptibility polymorphisms n = 7 | | | Total |
|---|---|---|---|---|
| | 1 | 2 | ≧3 | |
| Lung Cancer | 16 (15%) | 35 (32%) | 58 (53%) | 109 |
| Resistant smokers | 65 (33%) | 66 (33%) | 69 (34%) | 200 |

TABLE 33-continued

Combined Frequencies Of The Presence Or Absence Of Susceptibility Genotypes (CYP2E1 1019 CC/CG, FAS AA, IL-1B GG, ACT 15 GG, NAT2 GG, IL-18 105 AA, Ifnγ AA, N = 7) In The Exposed Smoking Subjects (Lung Cancer Subjects And Resistant Smokers).

| | | | | |
|---|---|---|---|---|
| % of smokers with Lung cancer | 16/81 (20%) | 35/101 (35%) | 58/127 (46%) | |

| Comparison | Odd's ratio | 95% CI | χ2 | P value |
|---|---|---|---|---|
| 0 vs 1 vs 2+, Lung cancer vs Resist | — | — | 14.6 | 0.0007 |
| 3+ vs 1-2, Lung cancer vs Resist | 2.2 | 1.3-5.6 | 9.4 | 0.002 |
| 1 vs 2-3+, Resist vs Lung cancer | 2.8 | 1.5-5.4 | 10.7 | 0.001 |

TABLE 34

Combined Frequencies Of The Presence Or Absence Of Protective Genotypes (CYP1A1 GG/AG, OGG1 GG, CCND1 GG, NOS3 298 TT, IL-8 AA, XRCC1 AA, Cox 2 −765 CC/CG) In The Exposed Smoking Subjects (Lung Cancer Subjects And Resistant Smokers).

| | Number of protective polymorphisms | | | |
|---|---|---|---|---|
| Cohorts | 0 | 1 | ≧2 | Total |
| Lung Cancer | 45 (40%) | 50 (43%) | 19 (17%) | 114 |
| Resistant smokers | 47 (23%) | 79 (40%) | 74 (37%) | 200 |
| % of smokers with Lung cancer | 45/47 (49%) | 50/129 (39%) | 19/93 (20%) | |

| Comparison | Odd's ratio | 95% CI | χ2 | P value |
|---|---|---|---|---|
| 0 vs 1 vs 2+, Resist vs Lung cancer | — | — | 16.8 | 0.0002 |
| 2+ vs 0-1, Resist vs Lung cancer | 2.94 | 1.6-5.4 | 13.44 | 0.0002 |
| 0 vs 2+, Lung cancer vs Resist | 2.12 | 1.3-3.6 | 8.2 | 0.004 |

TABLE 35

Combined Frequencies Of The Presence Or Absence Of Susceptibility Genotypes (CYP2E1 1019 CC/CG, FAS AA, IL-B1 GG, ACT 15 GG, MMP1 2G2G) In The Exposed Smoking Subjects (Lung Cancer Subjects And Resistant Smokers).

| | Number of suceptibility polymorphisms | | | |
|---|---|---|---|---|
| Cohorts | 0-1 | 2-3 | 4-6 | Total |
| Lung Cancer | 13 (12%) | 66 (61%) | 30 (28%) | 109 |
| Resistant smokers | 54 (27%) | 113 (56%) | 33 (17%) | 200 |
| % of smokers with Lung cancer | 13/67 (19%) | 66/179 (37%) | 30/63 (48%) | |

TABLE 35-continued

Combined Frequencies Of The Presence Or Absence Of Susceptibility Genotypes (CYP2E1 1019 CC/CG, FAS AA, IL-B1 GG, ACT 15 GG, MMP1 2G2G) In The Exposed Smoking Subjects (Lung Cancer Subjects And Resistant Smokers).

| Comparison | Odd's ratio | 95% CI | $\chi^2$ | P value |
|---|---|---|---|---|
| 0 vs 1 vs 2+, Lung cancer vs Resist | — | — | 11.8 | 0.003 |
| 2+ vs 0-1, Lung cancer vs Resist | 1.9 | 1.0-3.5 | 4.6 | 0.03 |
| 0+ vs 1-2+, Resist vs Lung cancer | 2.7 | 1.4-5.6 | 8.6 | 0.003 |

The above results show that several polymorphisms were associated with either increased or decreased risk of developing lung cancer. Additionally, while the associations of individual polymorphisms did provide discriminatory value, such predictions did not necessarily provide the most accurate prediction of disease possible. For example, when examined in combination, these polymorphisms distinguish susceptible subjects from those who are resistant (for example, between the smokers who develop lung cancer and those with the least risk with comparable smoking exposure). The polymorphisms represent both promoter polymorphisms, thought to modify gene expression and hence protein synthesis, and exonic polymorphisms known to alter amino-acid sequence (and likely expression and/or function) in a number of genes involved in processes known to underlie lung remodelling and lung cancer. The polymorphisms identified here are found in genes encoding proteins central to these processes which include inflammation, matrix remodelling, oxidant stress, DNA repair, cell replication and apoptosis.

In the comparison of smokers with lung cancer and matched smokers with near normal lung function (lowest risk for lung cancer despite smoking), several polymorphisms were identified as being found in significantly greater or lesser frequency than in the comparator groups (sometimes including the blood donor cohort). Due to the small cohort of lung cancer patients, polymorphisms where there are only trends towards differences (P=0.06-0.25) were included in the analyses, although in the combined analyses only those polymorphisms with the most significant differences were utilised.

In the analysis of the Asp 298 Glu (T/G) polymorphism of the Nitric oxide synthase 3 gene, the TT genotype was found to be greater in the smoking resistant cohort compared to the lung cancer cohort (OR=1.8, P=0.14) consistent with a protective role. This greater frequency compared to the blood donor cohort also suggests that the TT genotype is over represented in the resistant group (see Table 1E).

In the analysis of the −786 T/C polymorphism of the Nitric oxide synthase 3 gene, the TT genotype was found to be greater in the lung cancer cohort compared to the smoking resistant cohort (OR=1.4, P=0.23) consistent with a susceptibility role (see Table 1F).

In the analysis of the Arg 312 Gln polymorphism of the Superoxide dismutase 3 gene, the CG and GG genotypes were found to be significantly greater in the smoking resistant cohort compared to the lung cancer cohort (P=0.03) consistent with each having a protective role (Table 2).

In the analysis of the Arg 399 Gln A/G polymorphism of the XRCC1 gene, the AA genotype was found to be greater in the smoking resistant cohort compared to the lung cancer cohort (OR=2.6, P=0.09) consistent with a protective role (Table 3).

In the analysis of the −251 A/T polymorphism of Interleukin-8 gene, the AA genotype was found to be significantly greater in the smoking resistant cohort compared to the lung cancer cohort (OR=4.1, P=0.002) consistent with a protective role (Table 4). The A allele was also found to be significantly greater in the smoking resistant cohort compared to the lung cancer cohort (OR=1.5, P=0.02) consistent with a protective role (Table 4).

In the analysis of the Ala 15 Thr polymorphism of Antichymotrypsin gene, the GG genotype was found to be greater in the lung cancer cohort compared to the smoking resistant cohort (OR=1.7, P=0.06) consistent with a susceptibility role (see Table 5). The G allele was found to be greater in the lung cancer cohort compared to the smoking resistant cohort (OR=1.3, P=0.1) consistent with a susceptibility role (see Table 5).

In the analysis of the A 870 G polymorphism of the Cyclin D1 gene, the GG genotype was found to be greater in the smoking resistant cohort compared to the lung cancer cohort (OR=1.4, P=0.20) consistent with a protective role (see Table 6). In contrast, the AA genotype was found to be greater in the lung cancer cohort compared to the smoking resistant cohort (OR=1.4, P=0.2) consistent with a susceptibility role (see Table 6).

In the analysis of the −511 A/G polymorphism of the Interleukin 1B gene, the GG genotype was found to be significantly greater in the lung cancer cohort compared to the smoking resistant cohort (OR=1.6, P=0.04) consistent with a susceptibility role (see Table 7).

In the analysis of the A −670 G polymorphism of the FAS (Apo-1/CD95) gene, the AA genotype was found to be greater in the lung cancer cohort compared to the smoking resistant cohort (OR=1.5, P=0.15) consistent with a susceptibility role (see Table 8). The A allele was found to be greater in the lung cancer cohort compared to the smoking resistant cohort (OR=1.3, P=0.15) consistent with a susceptibility role (see Table 8).

In the analysis of the 751 T/G polymorphism of the XPD gene, the GG genotype was found to be greater in the smoking resistant cohort compared to the lung cancer cohort (OR=1.7, P=0.18) consistent with a protective role (Table 9).

In the analysis of the Ile 462 Val G/A polymorphism of the CYP 450 1A1 gene, the AG and GG genotypes were found to be greater in the smoking resistant cohort compared to the lung cancer cohort (OR=2.2, P=0.12) consistent with each having a protective role (see Table 10).

In contrast, the AA genotype was found to be consistent with a susceptibility role (see Table 10).

In the analysis of the Asn 357 Ser polymorphism of the Matrix metalloproteinase 12 gene, the GG and AG genotypes were found to be greater in the smoking resistant cohort compared to the lung cancer cohort (OR=1.7, P=0.23) consistent with each having a protective role (Table 11).

In the analysis of the Ser 326 Cys (C/G) polymorphism of the OGG1 gene, the GG genotype was found to be significantly greater in the smoking resistant cohort compared to the lung cancer cohort (OR=4.0, P=0.05) consistent with a protective role (Table 12).

In the analysis of the Arg 197 Gln G/A polymorphism of the N-Acetyltransferase 2 gene, the GG genotype was found to be greater in the lung cancer cohort compared to the smoking resistant cohort (OR=1.5, P=0.08) consistent with a susceptibility role (see Table 13).

In the analysis of the 1019 G/C Pst 1 polymorphism of the CYP 2E1 gene, the CG genotype was found to be greater in the lung cancer cohort compared to the smoking resistant cohort (OR=1.7, P=0.23) consistent with a susceptibility role (see Table 14a).

In the analysis of the C/T Rsa 1 polymorphism of the CYP 2E1 gene, the TC genotype was found to be greater in the lung cancer cohort compared to the smoking resistant cohort (OR=1.9, P=0.13) consistent with a susceptibility role (see Table 14b).

In the analysis of the 105 A/C polymorphism of the Interleukin-18 gene, the AA genotype was found to be greater in the lung cancer cohort compared to the smoking resistant cohort (OR=1.6, P=0.06) consistent with a susceptibility role (see Table 15a). In contrast, the AC and CC genotypes were each consistent with a protective role (see Table 15).

In the analysis of the −133 C/G polymorphism of the Interleukin-18 gene, the CC genotype was found to be greater in the lung cancer cohort compared to the smoking resistant cohort (OR=1.5, P=0.09) consistent with a susceptibility role (see Table 15b). In contrast, the CG and GG genotypes were each consistent with a protective role (see Table 15b).

In the analysis of the null polymorphism of the Glutathione S Transferase gene, the null genotype was found to be greater in the lung cancer cohort compared to the blood donor cohort (OR=1.92, P=0.01) consistent with a susceptibility role (see Table 16).

In the analysis of the 874 A/T polymorphism of the Interferon gamma gene, the AA genotype was found to be greater in the lung cancer cohort compared to the blood donor cohort (OR=1.9, P=0.02) and compared to the smoking resistant cohort (OR=1.4, P=0.22) consistent with a susceptibility role (see Table 17).

In the analysis of the −765 C/G promoter polymorphisms of the cyclo-oxygenase 2 gene, the C allele, and CC and CG genotypes were found to be significantly greater in the resistant smoker cohort compared to the lung cancer cohort (OR=0.59, P=0.03 and OR=0.53, P=0.03, respectively), consistent with a protective role. This greater frequency compared to the blood donor cohort also suggests that the C allele (CC genotype) is over-represented in the resistant group (see Table 18). In contrast, the G allele and GG genotype were found to be greater in the lung cancer cohort compared to the smoking resistant cohort (OR=1.7, P=0.03 and OR=1.88, P=0.03, respectively), consistent with a susceptibility role (see Table 18).

In the analysis of the −1607 1G/2G polymorphisms of the Matrix metalloproteteinase 1 gene, the 2G2G genotype was found to be significantly greater in the lung cancer cohort compared to the blood donor cohort (OR=2.58, P=0.006), consistent with a susceptibility role (see Table 19). The 2G allele was found to be significantly greater than the lung cancer cohort compared to the blood donor cohort (OR=2.1, P=0.0004), consistent with a susceptibility role (see Table 19).

In the analysis of the −447 G/C polymorphism of the connective tissue growth factor gene, the CC and GC genotypes were found to be greater in the lung cancer cohort compared to the smoking resistant cohort (OR=1.6, P=0.19) consistent with a susceptibility role (see Table 20).

In the analysis of the −221 C/T polymorphism in the Mucin 5AC gene the TT genotype was found to be greater in the resistant smoker cohort compared to the lung cancer cohort (OR=0.47, P=0.14) consistent with a protective role (see Table 21).

In the analysis of the 161 G/A polymorphism of the Mannose binding lectin (MBL2) gene, the AA and AG genotypes were found to be greater in the lung cancer cohort compared to the resistant smoker cohort (OR=1.4, P=0.20) consistent with each having a susceptibility role (see Table 22).

In the analysis of the Gln 185 Glu G/C polymorphism of the Nibrin gene, the CC genotype was found to be significantly greater in the lung cancer cohort compared to the resistant smoker cohort (OR=2.3, P=0.05), consistent with a susceptibility role (see Table 23).

In the analysis of the intron 1 C/T polymorphism of the Arginase 1 gene, the TT genotype was found to be significantly greater in the resistant smoker cohort compared to the lung cancer cohort (OR=0.46, P=0.02) consistent with a protective role (see Table 24). The T allele was found to be significantly greater in the resistant smoker cohort compared to the lung cancer cohort (OR=0.69, P=0.05) consistent with a protective role (see Table 24).

In the analysis of the Phe 257 Ser C/T polymorphism of the REV1 gene, the CC genotype was found to be greater in the resistant smoker cohort compared to the lung cancer cohort (OR=0.73, P=0.20), consistent with a protective role (see Table 25).

In the analysis of the Leu 252 Val C/G polymorphism of the Insulin-like growth factor II receptor gene the GG genotype was found to be greater in the resistant smoker cohort compared to the lung cancer cohort (OR=0.30, P=0.22) consistent with a protective role (see Table 26).

In the analysis of the Asp 148 Glu T/G polymorphism of the Apex nuclease gene, the GG genotype was found to be greater in the lung cancer cohort compared to the resistant smoker cohort (OR=1.4, P=0.25), consistent with a susceptibility role (see Table 27).

In the analysis of the −108 2A/G polymorphism of the Interleukin-10 gene the GG genotype was found to be greater in the resistant smoker cohort compared to the lung cancer cohort (OR=0.66, P=0.15), consistent with a protective role (see Table 28).

It is accepted that the disposition to lung cancer is the result of the combined effects of the individual's genetic makeup and other factors, including their lifetime exposure to various aero-pollutants including tobacco smoke. Similarly it is accepted that lung cancer encompasses several obstructive lung diseases and characterised by impaired expiratory flow rates (eg FEV1). The data herein reveal that several genes can contribute to the development of lung cancer. A number of genetic mutations working in combination either promoting or protecting the lungs from damage are likely to be involved in elevated resistance or susceptibility to lung cancer.

From the analyses of the individual polymorphisms, 17 protective genotypes were identified and analysed for their frequencies in the smoker cohort consisting of low risk smokers, i.e., resistant smokers (near normal lung function) and those with lung cancer. When the frequencies of resistant smokers and smokers with lung cancer were compared according to the presence of 0, 1 and 2+ protective genotypes selected from a subset of six of the protective genotypes (CYP1A1 GG/AG, OGG1 GG, CCND1 GG, NOS3 298 TT, IL-8 AA, XRCC1 AA), significant differences were found (overall $\gamma2=22.3$, $P<0.0001$) (see Table 30). This analysis suggests smokers with 2+ protective genotypes had 4-5 times more likelihood of being resistant (OR=4.6, P=0.0005), while those with no protective genotypes were nearly three times as likely to have lung cancer (OR=2.8, P<0.0001). Examined another way, the chance of having lung cancer diminished from 48%, to 30%, to 14%, in smokers with 0, 1, or 2+ protective genotypes, respectively. Analyses of larger groups of protective polymorphisms resulted in similar findings (see Tables 32 and 34).

From the analyses of the individual polymorphisms, 19 possible susceptibility genotypes were identified and analysed for their frequencies in the smoker cohort consisting of resistant smokers and those with lung cancer. When the frequencies of resistant smokers and smokers with lung cancer were compared according to the presence of 0, 1 and 2+ susceptibility genotypes selected from a subset of six of the susceptibility genotypes (CYP2E1 1019 CC/CG, FAS AA, IL-1B GG, ACT 15 GG genotypes) significant differences were found (overall $\gamma2=10.2$, $P=0.006$) (see Table 31). This analysis suggests that smokers with 2+ susceptibility genotypes had nearly two times more likelihood of having lung cancer (OR=1.8, P=0.04), while those with no susceptibility genotypes were two fold as likely to be resistant (OR=2.3, P=0.004). Examined another way, the chances of having lung cancer increased from 23%, to 38%, to 45% in smokers with 0, 1 or 2+ susceptibility genotypes, respectively. Analyses of larger groups of susceptibility polymorphisms resulted in similar findings (see Tables 33 and 35).

These findings indicate that the methods of the present invention can be predictive of lung cancer in an individual well before symptoms present.

These findings therefore also present opportunities for therapeutic interventions and/or treatment regimens, as discussed herein. Briefly, such interventions or regimens can include the provision to the subject of motivation to implement a lifestyle change, or therapeutic methods directed at normalising aberrant gene expression or gene product function. For example, the −765 G allele in the promoter of the gene encoding COX2 is associated with increased expression of the gene relative to that observed with the C allele. As shown herein, the C allele is protective with respect to risk of developing lung cancer, whereby a suitable therapy in subjects known to possess the −765 G allele can be the administration of an agent capable of reducing expression of the gene encoding COX2. An alternative suitable therapy can be the administration to such a subject of a COX2 inhibitor, and/or additional therapeutic approaches such as gene therapy or RNAi.

Example 34

A subject with the −765 G allele in the promoter of the gene encoding COX2 is identified. An agent that reduces the expression of the gene encoding COX2 is administered to the subject. An alternative suitable therapy can be the administration to such a subject of a COX2 inhibitor such as additional therapeutic approaches, gene therapy, RNAi. Thus, the risk that the subject will develop lung cancer will be reduced.

In another example, as shown herein the −133 C allele in the promoter of the gene encoding IL-18 is associated with susceptibility to lung cancer. The -133 G allele in the promoter of the gene encoding IL-18 is associated with increased IL-18 levels, whereby a suitable therapy in subjects known to possess the −133 C allele can be the administration of an agent capable of increasing expression of the gene encoding IL-18. An alternative therapy can be to administer IL-18 or an functional analogue thereof to a subject or to otherwise augment IL-18 levels in the subject.

Example 35

A subject with the −133C allele in the promoter of the gene encoding IL18 will be identified. An agent capable of increasing IL18 will be provided to the subject (for example, additional IL18). Repeated doses will be administered as needed. Thus, the risk that the subject will develop lung cancer will be reduced.

In a further example, as shown herein the −1607 2G/2G genotype in the promoter of the gene encoding MMP1 is associated with susceptibility to lung cancer. A number of inhibitors of matrix metalloproteinases are known, for example those discussed in U.S. Pat. No. 6,600,057 (incorporated herein in its entirety), such as tissue inhibitors of metalloproteinases (TIMPs) including TIMP1, TIMP2, TIMP3, and TIMP4, which form inactive complexes with MMPs, more general proteinase regulators which prevent MMP action, regulators of MMP gene expression including membrane bound MMPs (MT-MMP) that activate the excreted proenzyme form of MMPs, and compounds such as 4,5-dihydroxyanthaquinone-2-carboxylic acid (AQCA) and derivatives thereof. A suitable therapy in subjects known to possess the −1607 2G/2G genotype can be the administration of an agent capable of reducing expression of the gene encoding MMP1, or administration of an agent capable of reducing the activity of MMP1, for example by administration of an agent capable of increasing expression of or the activity of one or more TIMPs, or administration of an agent capable of reducing expression of or the activity of one or more membrane bound MMPs or other activators of MMP1. For example, a suitable therapy can be the administration to such a subject of a MMP1 inhibitor such as 4,5-dihydroxyanthaquinone-2-carboxylic acid (AQCA), anthraquinyl-mercaptoethyamine, anthraquinyl-alanine hydroxamate, or derivatives thereof. In another example, a given susceptibility genotype is associated with increased expression of a gene relative to that observed with the protective genotype. A suitable therapy in subjects known to possess the susceptibility genotype is the administration of an agent capable of reducing expression of the gene, for example using antisense or RNAi methods. An alternative suitable therapy can be the administration to such a subject of an inhibitor of the gene product. In still another example, a susceptibility genotype present in the promoter of a gene is associated with increased binding of a repressor protein and decreased transcription of the gene. A suitable therapy is the administration of an agent capable of decreasing the level of repressor and/or preventing binding of the repressor, thereby alleviating its downregulatory effect on transcription. An alternative therapy can include gene therapy, for example the introduction of at least one additional copy of the gene having a reduced affinity for repressor binding (for example, a gene copy having a protective genotype).

Example 36

A subject with the −1607 2G/2G genotype in the promoter of the gene encoding MMP1 is identified. The subject is administered an inhibitor of matrix metalloproteinases, such as tissue inhibitors of metalloproteinases (TIMPs) including TIMP1. Repeated administrations can be applied, thereby reducing the risk that the subject will develop lung cancer.

Suitable methods and agents for use in such therapy are well known in the art, and are discussed herein.

The identification of both susceptibility and protective polymorphisms as described herein also provides the opportunity to screen candidate compounds to assess their efficacy in methods of prophylactic and/or therapeutic treatment. Such screening methods involve identifying which of a range of candidate compounds have the ability to reverse or counteract a genotypic or phenotypic effect of a susceptibility polymorphism, or the ability to mimic or replicate a genotypic or phenotypic effect of a protective polymorphism.

Example 37

The present example provides one example for how one can screen for compounds that modulate the expression of a gene whose expression is upregulated or downregulated when associated with a susceptibility or protective polymorphism.

One first obtains a cell that includes a particular gene of interest. The expression of the gene of interest is upregulated or downregulated when associated with a susceptibility or a protective polymorphism. The polymorphism (and gene) can be selected from the following: the Asp 298 Glu TT genotype in the gene encoding NOS3; the Arg 312 Gln CG or GG genotype in the gene encoding SOD3; the Asn 357 Ser AG or GG genotype in the gene encoding MMP12; the 105 AC or CC genotype in the gene encoding IL-18; the −133 CG or GG genotype in the gene encoding IL-18; the −765 CC or CG genotype in the promoter of the gene encoding COX2; the −221 TT genotype in the gene encoding MUC5AC; the intron 1 C/T TT genotype in the gene encoding Arg1; the Leu252Val GG genotype in the gene encoding IGF2R; the −1082 GG genotype in the gene encoding IL-10; the −786 TT genotype in the promoter of the gene encoding NOS3; the Ala 15 Thr GG genotype in the gene encoding ACT; the 105 AA genotype in the gene encoding IL-18; the −133 CC genotype in the promoter of the gene encoding IL-18; the 874 AA genotype in the gene encoding IFNγ; the −765 GG genotype in the promoter of the gene encoding COX2; the −447 CC or GC genotype in the gene encoding CTGF; the +161 AA or AG genotype in the gene encoding MBL2; and some combination thereof.

In the cell, the expression of the gene is neither upregulated nor downregulated except as noted below. One then contacts the cell expressing the gene of interest with the candidate compound. Next, one determines the level of expression of the gene following contact of the cell with the candidate compound. A change in the level of expression after the contacting step as compared to before the contacting step is indicative of the ability of the compound to modulate an expression, activity, or expression and activity of the gene. As will be appreciated by on of skill in the art, the above method can allow one to identify compounds that can be useful in the treatment of lung cancer or in reducing the risk that one will develop lung cancer.

Still further, methods for assessing the likely responsiveness of a subject to an available prophylactic or therapeutic approach are provided. Such methods have particular application where the available treatment approach involves restoring the physiologically active concentration of a product of an expressed gene from either an excess or deficit to be within a range which is normal for the age and sex of the subject. In such cases, the can method include the detection of the presence or absence of a susceptibility polymorphism which when present either upregulates or downregulates expression of the gene such that a state of such excess or deficit is the outcome, with those subjects in which the polymorphism is present being likely responders to treatment.

Example 38

This example demonstrates one method of estimating the potential responsiveness of a subject to a prophylactic or therapeutic treatment for lung cancer. The treatment involves restoring the physiologically active concentration of a product of gene expression to within a range that is normal for the age and sex of a subject without lung cancer.

A subject at risk of developing or already having lung cancer is first identified. Next, one detects the presence or absence of a susceptibility polymorphism in the subject. The susceptibility polymorphism can be selected from the group consisting of: the −786 TT genotype in the promoter of the gene encoding NOS3; the Ala 15 Thr GG genotype in the gene encoding ACT; the 105 AA genotype in the gene encoding IL-18; the −133 CC genotype in the promoter of the gene encoding IL-18; the 874 AA genotype in the gene encoding IFNγ; the −765 GG genotype in the promoter of the gene encoding COX2; the −447 CC or GC genotype in the gene encoding CTGF; the +161 AA or AG genotype in the gene encoding MBL2; and some combination thereof. The presence of the polymorphism in the subject indicates that the subject will respond to treatment with an agent that appropriately alters the expression or activity of the particular gene that is altered by the polymorphism.

Example 39

Table 36 below presents representative examples of polymorphisms in linkage disequilibrium with the polymorphisms specified herein. Examples of such polymorphisms can be located using public databases, such as that available at world wide web "dot" hapmap "dot" org. Specified polymorphisms are indicated in parentheses. The rs numbers provided are identifiers unique to each polymorphism.

TABLE 36

| Polymorphism Reported To Be In LD With Polymorphisms Specified Herein. | | | | |
|---|---|---|---|---|
| NOS3 | | | | |
| rs2373962 | rs3918225 | rs3918169 | rs2373961 | rs3918160 |
| rs3918170 | rs6951150 | rs1800779 | rs3793342 | rs13238512 |
| rs2243311 | rs3793341 | rs10247107 | rs3918161 | rs1549758 |
| rs10276930 | rs10952298 | rs1007311 | rs10277237 | rs2070744 (−786 T/C) |

TABLE 36-continued

Polymorphism Reported To Be In LD With Polymorphisms Specified Herein.

| | | | | |
|---|---|---|---|---|
| rs9282803 | rs12703107 | rs9282804 | rs6946340 | rs3918226 |
| rs1799983 (Asp 298 Glu) | rs6946091 | rs3918162 | rs6946415 | rs3918163 |
| rs10952296 | rs3918164 | rs13309715 | rs3918165 | rs10952297 |
| rs1800781 | rs7784943 | rs13310854 | rs11771443 | rs13310763 |
| rs2243310 | rs2853797 | rs1800783 | rs13311166 | rs3918155 |
| rs13310774 | rs3918156 | rs2853798 | rs2566519 | rs11974098 |
| rs3918157 | rs3918166 | rs3918158 | rs3730001 | rs3918159 |
| rs3918167 | rs2566516 | rs3918168 | | |

XRCC1

| | | | | |
|---|---|---|---|---|
| rs1799782 | rs2307175 | rs2307173 | rs2307192 | rs2307176 |
| rs25492 | rs6413430 | rs3213363 | rs25493 | rs909008 |
| rs3213365 | rs25485 | rs1799780 | rs25488 | rs3213367 |
| rs3213360 | rs25489 | rs25486 | rs3213361 | rs2307188 |
| rs2271980 | rs915927 | rs3213366 | rs25487 (Arg 399 Gln) | rs3192714 |
| rs25490 | rs10407677 | rs25491 | | |

IL8

| | | | | |
|---|---|---|---|---|
| rs4694635 | rs2227527 | rs2227543 | rs11730560 | rs11730284 |
| rs1957663 | rs7682639 | rs12420 | rs13106097 | rs11944402 |
| rs4694636 | rs2227529 | rs16849942 | rs4694178 | rs7658422 |
| rs16849925 | rs2227530 | rs3181685 | rs4694637 | rs11940656 |
| rs16849928 | rs2227531 | rs11733933 | rs11729759 | rs1951700 |
| rs11730667 | rs2227532 | rs2227544 | rs10938093 | rs1951699 |
| rs16849934 | rs2227534 | rs2227545 | rs13109377 | rs1957662 |
| rs4073 (−251 A/T) | rs2227550 | rs1951236 | rs16849938 | rs2227546 |
| rs1951237 | rs6831816 | rs2227535 | rs1126647 | rs6446955 |
| rs2227517 | rs2227536 | rs11545234 | rs6446956 | rs2227518 |
| rs2227537 | rs2227548 | rs6446957 | rs2227519 | rs2227538 |
| rs10938092 | rs16849945 | rs2227520 | rs1803205 | rs13112910 |
| rs1951239 | rs2227521 | rs2227539 | rs13142454 | rs1951240 |
| rs2227522 | rs3756069 | rs11937527 | rs1957661 | rs2227523 |
| rs2227307 | rs12647924 | rs7674884 | rs2227524 | rs2227549 |
| rs13152254 | rs16849958 | rs2227525 | rs2227540 | rs13138765 |
| rs17202249 | rs2227526 | rs2227306 | rs13139170 | rs1951242 |

Anti-chymotrypsin, ACT

| | | | | |
|---|---|---|---|---|
| rs4900239 | rs6575448 | rs9323909 | rs4905225 | rs4362321 |
| rs2896288 | rs10131646 | rs1884082 | rs11160196 | rs10131818 |
| rs7492561 | rs10131754 | rs10133663 | rs11845108 | rs12886656 |
| rs1004761 | rs12886657 | rs9671421 | rs7493944 | rs7151480 |
| rs7493955 | rs9671431 | rs4934 (ACT Ala 15 Thr) | rs12433006 | rs9671948 |
| rs1800463 | rs10135321 | rs17826465 | rs10150184 | rs11538071 |
| rs10150491 | rs11538070 | | | |

CCND1

| | | | | |
|---|---|---|---|---|
| rs3862792 | rs11557712 | rs11604847 | rs12049899 | rs603965 (A 870 G) |
| rs678653 | rs1051357 | rs12288719 | rs3212893 | rs1803191 |
| rs12283700 | rs3918298 | rs2510607 | rs1803190 | rs948886 |
| rs3918299 | rs3212894 | rs3212910 | rs948887 | rs3918301 |
| rs3212895 | rs3212911 | rs3212880 | rs3212896 | rs3212912 |
| rs3212881 | rs3212897 | rs3212913 | rs3212882 | rs3212898 |
| rs3212915 | rs3212883 | rs11557584 | rs3212916 | rs3212884 |
| rs2062445 | rs3212917 | rs3781611 | rs3212899 | rs3212918 |
| rs649392 | rs3212900 | rs3212919 | rs3212885 | rs3212901 |
| rs12805391 | rs3212886 | rs3212902 | rs3212920 | rs3212887 |
| rs3212903 | rs3212921 | rs3918302 | rs3212904 | rs3212922 |
| rs7944853 | rs1051062 | rs11603541 | rs3212888 | rs3212905 |
| rs7116781 | rs3212889 | rs3212906 | rs7121246 | rs3212890 |
| rs3212907 | rs7124951 | rs3212891 | rs3212908 | rs12281701 |
| rs2510467 | rs3212909 | rs12288567 | rs3212892 | rs3802782 |
| rs1192925 | rs7177 | rs7178 | rs1192926 | |

Interleukin 1B, IL1B

| | | | | |
|---|---|---|---|---|
| rs10169916 | rs6743326 | rs13009179 | rs6743322 | rs4849127 |
| rs6761220 | rs4849126 | rs6761218 | rs7558108 | rs5021469 |
| rs13032029 | rs6710598 | rs13013349 | rs1143623 | rs12623093 |
| rs1143624 | rs3087255 | rs2708920 | rs3087256 | rs1143625 |
| rs6721954 | rs2853545 | rs12621220 | rs2708921 | rs7596849 |
| rs1143626 | rs4848306 | rs3087258 | rs3087257 | rs16944 (C −511 T) |
| rs7556811 | rs7556903 | rs3917346 | rs6743438 | rs4986962 |
| rs6743427 | rs1143627 | rs6761336 | rs6761335 | rs6743338 |
| rs6761245 | rs6761237 | rs6743330 | | |

TABLE 36-continued

Polymorphism Reported To Be In LD With
Polymorphisms Specified Herein.

FAS, TNFRSF6

| | | | | |
|---|---|---|---|---|
| rs3758483 | rs6586166 | rs9658718 | rs3218618 | rs2234767 |
| rs6586167 | rs1926193 | rs12720435 | rs9658674 | rs9658691 |
| rs1926192 | rs7910435 | rs9658675 | rs9658692 | rs1926191 |
| rs17114661 | rs2234768 | rs9658693 | rs4244983 | rs3218614 |
| rs1800682 (A −670 G) | rs9658694 | rs9658719 | rs9658754 | rs9658695 |
| rs9658721 | rs12720436 | rs9658676 | rs4345878 | rs9658722 |
| rs7911226 | rs5030765 | rs9658696 | rs9658723 | rs1926190 |
| rs7474952 | rs9658697 | rs11202924 | rs9658755 | rs9658677 |
| rs9658698 | rs9658724 | rs9658756 | rs12251390 | rs9658699 |
| rs9658725 | rs9658757 | rs2274355 | rs9658700 | rs9658726 |
| rs3781202 | rs5030766 | rs9658702 | rs2296604 | rs9658759 |
| rs12775501 | rs7094676 | rs9658727 | rs9658761 | rs7079111 |
| rs9658703 | rs9658728 | rs982764 | rs3740286 | rs9658704 |
| rs9658729 | rs9658763 | rs4064 | rs9658705 | rs7069750 |
| rs3218620 | rs1324551 | rs9658706 | rs9658730 | rs2296600 |
| rs10509561 | rs9658707 | rs9658731 | rs6586163 | rs1571011 |
| rs3218619 | rs6586164 | rs9658708 | rs9333296 | rs3824730 |
| rs1571012 | rs3218621 | rs3781204 | rs1571013 | rs3218613 |
| rs12571917 | rs9658710 | rs9658732 | rs3824729 | rs9658711 |
| rs2296603 | rs10887877 | rs7911752 | rs9658733 | rs11596616 |
| rs11591675 | rs9658734 | rs7076197 | rs11591676 | rs9658735 |
| rs12359362 | rs12766185 | rs9658736 | rs7097467 | rs11591677 |
| rs9658738 | rs7097572 | rs9658712 | rs9658739 | rs9658679 |
| rs9658713 | rs9658740 | rs9658680 | rs2147421 | rs9658741 |
| rs1926196 | rs2147420 | rs7896789 | rs1926195 | rs9658714 |
| rs9658742 | rs9658681 | rs1159120 | rs9658744 | rs9325603 |
| rs4406737 | rs9658745 | rs2031610 | rs2148287 | rs9658748 |
| rs7897395 | rs9658715 | rs9658749 | rs7909414 | rs9658716 |
| rs7901656 | rs9658682 | rs2147419 | rs9658750 | rs7069061 |
| rs2148286 | rs9658751 | rs7072828 | rs2147418 | rs2031613 |
| rs6586165 | rs9658717 | rs2031612 | rs9658683 | rs4406738 |
| rs9658753 | rs9658684 | rs7916814 | rs2296602 | rs9658685 |
| rs2182408 | rs2031611 | rs7913040 | rs7920305 | rs3218612 |
| rs9658687 | rs1926194 | rs2296601 | | |

XPD, ERCC2

| | | | | |
|---|---|---|---|---|
| rs1799793 | rs238409 | rs3916858 | rs3916876 | rs7257638 |
| rs3916838 | rs106433 | rs238417 | rs3916816 | rs50871 |
| rs3916860 | rs3916878 | rs3916817 | rs50872 | rs3916861 |
| rs3916879 | rs3916818 | rs3916839 | rs3916862 | rs1799787 |
| rs3916819 | rs3916840 | rs3916863 | rs1799788 | rs3916820 |
| rs3916841 | rs238412 | rs1799789 | rs238404 | rs3916842 |
| rs3916864 | rs16979773 | rs3916821 | rs3916843 | rs11668936 |
| rs1052555 | rs3916822 | rs3916844 | rs3916866 | rs3916881 |
| rs238403 | rs7251321 | rs2070831 | rs3916882 | rs171140 |
| rs3916845 | rs3916868 | rs3916883 | rs3895625 | rs3916846 |
| rs238413 | rs238418 | rs3916824 | rs3916847 | rs238414 |
| rs3916885 | rs3916825 | rs3916848 | rs3916870 | rs3916886 |
| rs3916826 | rs238410 | rs3916871 | rs1799790 | rs3916827 |
| rs238411 | rs3916872 | rs13181 (751 G/T) | rs3916830 | rs3916849 |
| rs238415 | rs3916831 | rs3916850 | rs3916873 | rs3916832 |
| rs3916851 | rs3932979 | rs3916833 | rs3916853 | rs238416 |
| rs3916834 | rs3916854 | rs3916874 | rs3916835 | rs3916855 |
| rs11667568 | rs3916836 | rs3916856 | rs3916875 | rs3916837 |
| rs3916857 | rs11666730 | | | |

CYP1A1

| | | | | |
|---|---|---|---|---|
| rs11631784 | rs4646418 | rs2515900 | rs7496395 | rs2856844 |
| rs4646903 | rs7496533 | rs2606345 | rs2472309 | rs4886605 |
| rs8031941 | rs2472308 | rs12441817 | rs4646420 | rs12915975 |
| rs2470891 | rs4646421 | rs6495121 | rs2470892 | rs4986885 |
| rs1456432 | rs7182554 | rs2606344 | rs2198843 | rs936225 |
| rs4646422 | rs11072499 | rs7180012 | rs2229150 | rs8039800 |
| rs4986879 | rs7179952 | rs4987133 | rs7181062 | rs2856833 |
| rs7179590 | rs1799814 | rs7180066 | rs1048943 (Ile 462 Val) | rs7495708 |
| rs2470893 | rs2278970 | rs3809585 | rs2606346 | rs2445619 |
| rs4986880 | rs2472296 | rs4986881 | rs4646417 | rs4986882 |
| rs2856831 | rs1800031 | rs2856832 | rs4986883 | rs3826042 |
| rs4986884 | rs3826041 | rs2472307 | | |

MMP12

| | | | | |
|---|---|---|---|---|
| rs652438 (Asn 357 Ser) | rs641519 | rs585007 | rs640735 | rs672745 |
| rs651159 | rs644008 | rs672743 | rs644552 | rs1291647 |
| rs12794039 | rs476185 | rs1291646 | rs12796315 | rs476391 |
| rs1295870 | rs505770 | rs1291645 | rs1042509 | rs597518 |

TABLE 36-continued

Polymorphism Reported To Be In LD With Polymorphisms Specified Herein.

| | | | | |
|---|---|---|---|---|
| rs626729 | rs626407 | rs686375 | rs626393 | rs12808148 |
| rs1291643 | rs484171 | rs1296235 | rs660727 | rs1291642 |
| rs7102181 | rs1296234 | rs674546 | rs1794204 | rs7128711 |
| rs580266 | rs660599 | rs615932 | rs511081 | rs737693 |
| rs654600 | rs686439 | rs645763 | rs518509 | rs561849 |
| rs586701 | rs641957 | rs11821430 | rs1296237 | rs1299505 |
| rs641920 | rs673217 | rs644885 | rs673163 | |

OGG1

| | | | | |
|---|---|---|---|---|
| rs159154 | rs11548133 | rs3219007 | rs2471902 | rs17291491 |
| rs3219001 | rs3219008 | rs2308329 | rs12498111 | rs17050550 |
| rs3219009 | rs2072668 | rs454071 | rs1801127 | rs159150 |
| rs3219012 | rs11928210 | rs2472031 | rs1805373 | rs2471903 |
| rs17050542 | rs3219002 | rs2472038 | rs2472042 | rs17775374 |
| rs2471894 | rs3219010 | rs3219013 | rs17050543 | rs2472032 |
| rs2472039 | rs1801128 | rs17050545 | rs4986999 | rs2472040 |
| rs3219014 | rs1042294 | rs2472033 | rs2472041 | rs9824261 |
| rs2269112 | rs2472034 | rs4686370 | rs1052133 (Ser 326 Cys) | rs17050547 |
| rs3219003 | rs2471899 | rs11632 | rs2472035 | rs9818365 |
| rs3895085 | rs2619496 | rs2075747 | rs159153 | rs415153 |
| rs1091453 | rs3218993 | rs3219004 | rs2471900 | rs3218994 |
| rs2471895 | rs809256 | rs3218995 | rs2471896 | rs812536 |
| rs125701 | rs2472036 | rs2471901 | rs3218996 | rs2471897 |
| rs786514 | rs3218997 | rs3219005 | rs809784 | rs3218999 |
| rs159151 | rs3219011 | rs1801129 | rs6787046 | rs786513 |
| rs1801126 | rs2472037 | rs786512 | rs11548134 | rs3219006 |
| rs810862 | | | | |

NAT2

| | | | | |
|---|---|---|---|---|
| rs11780272 | rs1495744 | rs2101857 | rs7832071 | rs13363820 |
| rs1805158 | rs6984200 | rs1801279 | rs13277605 | rs1041983 |
| rs9987109 | rs1801280 | rs7820330 | rs4986996 | rs7460995 |
| rs12720065 | rs2087852 | rs4986997 | rs2101684 | rs1799929 |
| rs7011792 | rs1799930 (Arg 197 Gln) | rs1390358 | rs923796 | rs1208 |
| rs4546703 | rs1799931 | rs4634684 | rs2552 | rs2410556 |
| rs4646247 | rs11996129 | rs971473 | rs4621844 | rs721398 |
| rs11785247 | rs1115783 | rs11157841 | rs1961456 | rs1112005 |
| rs11782802 | rs973874 | | | |

CYP2E1

| | | | | |
|---|---|---|---|---|
| rs7091961 | rs12776213 | rs1329148 | rs10857736 | rs12262150 |
| rs6537611 | rs10857732 | rs10857737 | rs9418989 | rs6537612 |
| rs10857733 | rs12776473 | rs10776686 | rs10466129 | rs1101801 |
| rs10466130 | rs4838767 | rs11101810 | rs9419081 | rs9418990 |
| rs9419082 | rs10857738 | rs11101803 | rs11101811 | rs10776687 |
| rs3813865 | rs4838688 | rs3813866 | rs11101805 | rs11575869 |
| rs2031918 | rs8192766 | rs2031919 | rs11575870 | rs11101806 |
| rs6413423 | rs4838689 | rs3813867 (1019 G/C Pst1) | rs10857734 | rs4838768 |
| rs6413422 | rs11101807 | rs2031920 (Rsa1 C/T) | rs11101808 | rs11101809 |
| rs10857735 | | | | |

IL18

| | | | | |
|---|---|---|---|---|
| rs187238 | rs5744238 | rs5744255 | rs5744228 | rs5744239 |
| rs5744256 | rs360718 | rs7932965 | rs5744257 | rs360717 |
| rs11214103 | rs360720 | rs5744229 | rs5744241 | rs5744258 |
| rs100000353 | rs5744242 | rs5744259 | rs5744231 | rs5744243 |
| rs5744260 | rs5744232 | rs5744244 | rs5744261 | rs7106524 |
| rs360722 | rs549908 (105 A/C) | rs189667 | rs5023207 | rs12290658 |
| rs5744246 | rs12271175 | rs5744247 | rs11606049 | rs360721 (−133 C/G) |
| rs360716 | rs360715 | rs4988359 | rs360714 | rs12721559 |
| rs2043055 | rs5744248 | rs5744233 | rs5744249 | rs795467 |
| rs5744250 | rs12270240 | rs5744251 | rs100000354 | rs100000356 |
| rs4937113 | rs1834481 | rs100000355 | rs17215057 | rs360723 |
| rs5744253 | rs5744237 | rs5744254 | | |

GSTM1

| | | | | |
|---|---|---|---|---|
| (Null genotype) | Not in LD | | | |

MMP1

| | | | | |
|---|---|---|---|---|
| rs529381 | rs685265 | rs1144396 | rs7107224 | rs504875 |
| rs1155764 | rs526215 | rs534191 | rs12280880 | rs509332 |
| rs542603 | rs12283759 | rs574939 | rs2105581 | rs573764 |
| rs470206 | rs7102189 | rs533621 | rs575727 | rs1799750 (−1607 G/GG) |
| rs552306 | rs634607 | rs470211 | rs12286876 | rs470146 |
| rs12285331 | rs2075847 | rs519806 | rs473509 | rs12283571 |

TABLE 36-continued

Polymorphism Reported To Be In LD With Polymorphisms Specified Herein.

| | | | | |
|---|---|---|---|---|
| rs498186 | rs2839969 | rs2000609 | rs7125865 | rs570662 |
| rs11225427 | rs484915 | rs470307 | rs2408490 | rs12279710 |

COX2

| | | | | |
|---|---|---|---|---|
| rs7527769 | rs689465 | rs4648270 | rs7550380 | rs12027712 |
| rs12759220 | rs2206594 | rs689466 | rs20430 | rs6687495 |
| rs2745558 | rs4648271 | rs6681231 | rs3918304 | rs11567825 |
| rs13376484 | rs20415 | rs4648273 | rs12064238 | rs20416 |
| rs16825748 | rs10911911 | rs4648254 | rs4648274 | rs12743673 |
| rs11567815 | rs16825745 | rs10911910 | rs20417 (−765G > C) | rs20432 |
| rs12743516 | rs20433 | rs10911909 | rs4648256 | rs3218622 |
| rs1119066 | rs20419 | rs2066826 | rs1119065 | rs2734779 |
| rs5278 | rs1119064 | rs20420 | rs4648276 | rs10798053 |
| rs20422 | rs20434 | rs12409744 | rs20423 | rs3218623 |
| rs10911908 | rs5270 | rs3218624 | rs10911907 | rs20424 |
| rs5279 | rs7416022 | rs5271 | rs4648278 | rs2745561 |
| rs4648257 | rs13306034 | rs10911906 | rs11567819 | rs2853803 |
| rs2734776 | rs3134591 | rs4648279 | rs2734777 | rs3134592 |
| rs4648281 | rs12084433 | rs20426 | rs4648282 | rs2734778 |
| rs4648258 | rs11567826 | rs2745560 | rs11567820 | rs4648283 |
| rs2223627 | rs2745557 | rs4648284 | rs2383517 | rs11567821 |
| rs4648285 | rs4295848 | rs4648259 | rs11567827 | rs4428839 |
| rs4648260 | rs4648286 | rs4609389 | rs4648261 | rs4648287 |
| rs4428838 | rs4648262 | rs5272 | rs12131210 | rs11567822 |
| rs4648288 | rs2179555 | rs11567823 | rs5273 | rs2143417 |
| rs2066824 | rs5274 | rs2143416 | rs20427 | rs3218625 |
| rs11583191 | rs5277 | rs4648289 | rs2383516 | rs2066823 |
| rs4648290 | rs2383515 | rs4648263 | rs1051896 | rs10911905 |
| rs4987012 | rs5275 | rs10911904 | rs20428 | rs6684912 |
| rs20429 | rs2745559 | rs4648264 | rs12042763 | rs4648265 |
| rs4648250 | rs4648266 | rs4648251 | rs4648267 | rs2223626 |
| rs11567824 | rs689462 | rs4648268 | rs4648253 | rs4648269 |

IFNG

| | | | | |
|---|---|---|---|---|
| rs2069707 | rs2069720 | rs3814242 | rs1042274 | rs2069709 |
| rs2069721 | rs2069710 | rs2069734 | rs2069711 | rs2069722 |
| rs2069712 | rs2234687 | rs2430561 (874 A/T) | rs7957366 | rs2069723 |
| rs2069713 | rs2069724 | rs1861494 | rs2069725 | rs2234685 |
| rs4394909 | rs1861493 | rs2069726 | rs2069714 | rs2069727 |
| rs2069715 | rs2069716 | rs2069717 | rs2069718 | rs3087272 |
| rs2069719 | rs9282708 | | | |

CTGF

| | |
|---|---|
| (−447 G/C), no rs number | Region of recombination |

MUC5AC

| | |
|---|---|
| (−221 C/T, no rs number | No LD data |

MBL2

| | | | | |
|---|---|---|---|---|
| rs7899547 | rs12264958 | rs12255312 | rs10824797 | rs11003126 |
| rs11003122 | rs11003131 | rs1031101 | rs1982267 | rs930506 |
| rs10824795 | rs1982266 | rs930505 | rs10824794 | rs4935047 |
| rs11003130 | rs920725 | rs4935046 | rs2384044 | rs7916582 |
| rs10824793 | rs2384045 | rs920724 | rs1838066 | rs5027257 |
| rs16933335 | rs1838065 | rs2384046 | rs11003125 | rs930509 |
| rs12263867 | rs7100749 | rs930508 | rs11003129 | rs11003124 |
| rs930507 | rs12221393 | rs7084554 | rs2165811 | rs7096206 |
| rs12782244 | rs11003123 | rs11003128 | rs11575988 | rs17664818 |
| rs11575989 | rs7475766 | rs7095891 | rs10824796 | rs4647963 |
| rs16933417 | rs8179079 | rs2165810 | rs5030737 | rs11003127 |
| rs1800450 (161 G/A) | rs3925313 | rs7094151 | rs1800451 | rs7071882 |
| rs12246310 | | | | |

SOD3

| | |
|---|---|
| rs1799895 (Arg 231 Gly) | Region of low LD |

APEX1

| | |
|---|---|
| rs3136820 (Asp 148 Glu) | Recombination region |

NBS1

| | | | | |
|---|---|---|---|---|
| rs1805800 | rs1805793 | rs1805824 | rs1805788 | rs3026273 |
| rs13312874 | rs13312891 | rs1805787 | rs1805847 | rs7463645 |
| rs1805823 | rs1805816 | rs13312847 | rs13312877 | rs6990969 |
| rs3026269 | rs1805846 | rs3026272 | rs13312893 | rs1805815 |

TABLE 36-continued

Polymorphism Reported To Be In LD With
Polymorphisms Specified Herein.

| | | | | |
|---|---|---|---|---|
| rs1805845 | rs1805833 | rs13312894 | rs13312922 | rs1805844 |
| rs1805832 | rs741777 | rs1805786 | rs13312849 | rs7818138 |
| rs13312895 | rs709816 | rs1805799 | rs9792335 | rs6985934 |
| rs13312850 | rs2339025 | rs867185 | rs13312851 | rs3358 |
| rs4596696 | rs13312852 | rs13277858 | rs1805822 | rs13312853 |
| rs1805831 | rs1805790 | rs2073635 | rs1805830 | rs1569162 |
| rs1063045 | rs2293775 | rs1805821 | rs13312854 | rs13259550 |
| rs1805820 | rs13312855 | rs741778 | rs1235369 | rs1805798 |
| rs1805829 | rs3026270 | rs1805797 | rs1805828 | rs1805789 |
| rs2308961 | rs769416 | rs9694776 | rs13312858 | rs2272581 |
| rs2293774 | rs13312859 | rs13312879 | rs7008218 | rs1805796 |
| rs3026271 | rs11998021 | rs1805843 | rs1805827 | rs13312896 |
| rs769417 | rs13312880 | rs13312897 | rs769414 | rs769418 |
| rs12550313 | rs1805842 | rs769420 | rs13312898 | rs1805841 |
| rs13312881 | rs13312900 | rs13312860 | rs2308960 | rs13312901 |
| rs1805840 | rs1805826 | rs16786 | rs13312861 | rs10092465 |
| rs13312902 | rs1805839 | rs13312883 | rs1805819 | rs1805838 |
| rs1805792 | rs2234744 | rs13312862 | rs13312884 | rs13312903 |
| rs13312863 | rs13312885 | rs1805818 | rs1805837 | rs13312886 |
| rs7818042 | rs13312864 | rs13312887 | rs13312904 | rs13312865 |
| rs1805791 | rs7818989 | rs13312866 | rs1805825 | rs13312905 |
| rs13312867 | rs13278453 | rs13312906 | rs11995115 | rs13275276 |
| rs13312907 | rs1805836 | rs10282890 | rs9650096 | rs1805795 |
| rs16902052 | rs9649958 | rs7832009 | rs7006322 | rs7010210 |
| rs1805835 | rs7006318 | rs13312913 | rs13312871 | rs6987873 |
| rs2516635 | rs13312872 | rs9650098 | rs13312916 | rs1805794 (Gln 185 Glu) |
| rs13312888 | rs11784904 | rs13312889 | rs13312921 | rs1805834 |
| rs13312890 | rs1805817 | | | |

ARG1

| | | | | |
|---|---|---|---|---|
| rs2781659 | rs2781660 | rs2781661 | rs2781662 | rs2781663 |
| rs2608898 | rs2781664 | rs3756780 | rs2781665 | rs2608897 |
| rs2781666 | rs17788484 | rs9493029 | rs2781667 (Intron1 C/T) | |

REV1, REV1L

| | | | | |
|---|---|---|---|---|
| rs6714244 | rs10172068 | rs1000409 | rs7597141 | rs3208832 |
| rs1839666 | rs10180138 | rs5013068 | rs6714650 | rs1801874 |
| rs7560795 | rs12465846 | rs1451245 | rs17022663 | rs14534 |
| rs10179697 | rs9308821 | rs3792141 | rs17763586 | rs2305353 |
| rs4143760 | rs10183488 | rs3792142 | rs13402784 | rs2305352 |
| rs10173883 | rs7580448 | rs3792143 | rs7574943 | rs12474305 |
| rs10176205 | rs7426356 | rs3792144 | rs4851205 | rs13423815 |
| rs12470050 | rs13395100 | rs2309585 | rs7571793 | rs17022639 |
| rs7571186 | rs11889026 | rs7573502 | rs3792152 | rs7579403 |
| rs13384316 | rs13395095 | rs10179435 | rs10177775 | rs12053237 |
| rs6542882 | rs11889025 | rs7423755 | rs3087394 | rs12233126 |
| rs13430962 | rs2053917 | rs1451244 | rs3087398 | rs11123786 |
| rs13427780 | rs13392042 | rs3087386 (Phe 257 Ser) | rs2242037 | rs11123785 |
| rs6737560 | rs13429806 | rs11675410 | rs3197957 | rs1011633 |
| rs10173466 | rs3087391 | rs17022653 | rs2242036 | rs6707685 |
| rs10170425 | rs3087399 | rs12104881 | rs17022634 | rs13420087 |
| rs10172752 | rs10175852 | rs12104509 | rs3205290 | rs6713792 |
| rs10169151 | rs12105223 | rs12105686 | rs7593274 | rs7564587 |
| rs4851206 | rs7582085 | rs12104601 | rs13389623 | rs11676988 |
| rs7567674 | rs6542880 | rs13420293 | rs11695517 | rs7594838 |
| rs11695422 | rs3087383 | rs2309604 | rs13432046 | rs7582133 |
| rs3087385 | rs6542881 | rs10210346 | rs13419448 | rs3749087 |
| rs896249 | rs10210257 | rs3087402 | rs7560996 | rs737094 |
| rs13385501 | rs3792146 | rs7601730 | rs11893335 | rs2122748 |
| rs3792147 | rs13428419 | rs13405400 | rs13427424 | rs3792148 |
| rs3828316 | rs13405256 | rs10188633 | rs13409359 | rs717454 |
| rs9308823 | rs1451246 | rs10496337 | rs13394927 | rs1973011 |
| rs1839667 | rs6542879 | rs3087396 | rs13398476 | rs9973846 |
| rs3792149 | rs1053544 | rs9308822 | rs11899745 | rs4341989 |
| rs2290261 | rs10191001 | rs10865031 | rs12479064 | rs2290260 |
| rs6746320 | rs7572779 | rs13429185 | rs3087401 | rs6728175 |
| rs7563462 | rs6717515 | rs6711073 | rs13415713 | rs7563455 |
| rs6727483 | rs12465153 | rs11902376 | rs12986447 | rs11887109 |
| rs3087389 | rs17022732 | rs2053916 | rs12619546 | rs3087388 |
| rs6748200 | rs3792135 | rs10182492 | rs3209289 | rs3792134 |
| rs3792136 | rs3792150 | rs1046340 | rs3087382 | rs3792137 |
| rs3792151 | rs3087393 | rs3087384 | rs13416265 | rs6723062 |
| rs2305354 | rs896248 | rs3792138 | rs1451243 | rs3792392 |
| rs959929 | rs13387148 | rs13426758 | rs3087400 | rs769105 |
| rs1901283 | rs9941566 | rs3087387 | rs7421436 | rs10207435 |
| rs7602535 | rs3792153 | rs13400661 | rs7598629 | rs3087395 |
| rs2290259 | rs7585019 | rs3087403 | rs17763718 | rs2290258 |

TABLE 36-continued

Polymorphism Reported To Be In LD With Polymorphisms Specified Herein.

| rs13394688 | rs3087390  | rs4535093  | rs9308819          | rs10207981 |
|------------|------------|------------|--------------------|------------|
| rs10186223 | rs10206944 | rs2290257  |                    |            |

IGF2R

| rs3798189  | rs8191748 | rs1570070  | rs8191771           | rs3798188  |
|------------|-----------|------------|---------------------|------------|
| rs8191750  | rs8191764 | rs8191772  | rs3798187           | rs8191751  |
| rs8191765  | rs8191773 | rs9365122  | rs3798186           | rs408889   |
| rs13198308 | rs9347380 | rs6455680  | rs8191766           | rs8191774  |
| rs6904531  | rs8191752 | rs8191767  | rs8191775           | rs2342868  |
| rs11751626 | rs8191768 | rs2297358  | rs12174439          | rs8191753  |
| rs2297357  | rs3777413 | rs12173776 | rs8191754 (Leu 252 Val) | rs8191769 |
| rs3798185  | rs9347382 | rs8191770  | rs435612            | rs9365124  |
| rs2297356  | rs448116  | rs8191776  | rs9457809           | rs8191755  |
| rs399919   | rs6413489 | rs12179343 | rs8191756           | rs1867348  |
| rs894817   | rs449276  | rs8191757  | rs7762627           | rs9456496  |
| rs9295121  | rs7763887 | rs9456497  | rs9365125           | rs11758686 |
| rs9457811  | rs8191758 | rs681401   | rs9457812           | rs8191759  |
| rs9456499  | rs9295120 | rs8191760  | rs12662414          | rs9456498  |
| rs8191761  | rs4709391 | rs2277071  | rs4709390           | rs13218689 |
| rs11759563 | rs8191762 | rs13220128 | rs8191746           | rs8191763  |
| rs1036951  | rs2277070 | rs12374637 | rs4709392           | rs8191747  |
| rs12374638 | rs3777414 |            |                     |            |

IL10

| rs1800896 (−1082 A/G) | rs3021098 | rs5743626 | rs3024509 | rs2222202 |
|------------------------|-----------|-----------|-----------|-----------|
| rs1554286              | rs5743627 | rs1800894 | rs3024490 | rs2352792 |
| rs3024495              | rs1800871 | rs3790622 | rs3024492 | rs5743628 |
| rs1800895              | rs3021093 | rs3024507 | rs3024496 | rs1800872 |
| rs3024491              | rs3024493 | rs3024497 | rs3024488 | rs3021094 |
| rs1878672              | rs3024510 | rs3024489 | rs1518110 | rs3024508 |
| rs3024498              | rs5743625 | rs3024506 | rs9282740 | rs3001099 |
| rs1518111              | rs3024494 |           |           |           |

INDUSTRIAL APPLICATION

The present invention is directed to methods for assessing a subject's risk of developing lung cancer. The methods include the analysis of polymorphisms herein shown to be associated with increased or decreased risk of developing lung cancer, or the analysis of results obtained from such an analysis. The use of polymorphisms herein shown to be associated with increased or decreased risk of developing lung cancer in the assessment of a subject's risk are also provided, as are nucleotide probes and primers, kits, and microarrays suitable for such assessment. Methods of treating subjects having the polymorphisms herein described are also provided. Methods for screening for compounds able to modulate the expression of genes associated with the polymorphisms herein described are also provided.

Additional information regarding the above methods and compositions can be found in U.S. patent application Ser. No. 10/479,525, filed Jun. 16, 2004; and PCT Application No. PCT/NZ02/00106, filed Jun. 5, 2002, which further designates New Zealand Application No. 512169, filed Jun. 5, 2001; New Zealand Application No. 513016, filed Jul. 17, 2001, and New Zealand Application No. 514275, filed Sep. 18, 2001, all of which are incorporated by reference in their entireties. Additional information can also be found in PCT application Nos. PCT/NZ2006/000103 and PCT/NZ2006/000104, filed May 10, 2006, entitled "Methods and Compsitions for Assessment of Pulmonary Function and Disorders" and "Methods of Analysis of Polymorphisms and Uses Thereof", both of which are incorporated in their entireties by reference. PCT Application No. PCT/NZ 2006/000103 claims priority to: NZ application No. 539934, filed May 10, 2005; NZ application No. 541935, filed Aug. 19, 2005; and JP application No. 2005-360523, filed Dec. 14, 2005, all of which are incorporated by reference in their entireties. PCT Application No. PCT/NZ2006/000104 claims priority to: NZ application No. 540249, filed May 20, 2005; and NZ application No. 541842, filed Aug. 15, 2005, all of which are incorporated in their entirties by reference. Additional information can also be found in U.S. patent application Ser. No. 11/432,770, filed May 10, 2006, entitled "Methods of Analysis of Polymorphisms and Uses Thereof,"incorporated in its entirety.

PUBLICATIONS

1. Alberg A J, Samet J M. Epidemiology of lung cancer. Chest 2003, 123, 21s-49s.
2. Anthonisen N R. Prognosis in COPD: results from multicenter clinical trials. Am Rev Respir Dis 1989, 140, s95-s99.
3. Cantlay A M, Smith C A, Wallace W A, Yap P L, Lamb D, Harrison D J. Heterogeneous expression and polymorphic genotype of glutathione S-transferases in human lung. Thorax. 1994, 49(10):1010-4.
4. Kuller L H, et al. Relation of forced expiratory volume in one second to lung cancer mortality in the MRFIT. Am J Epidmiol 1190, 132, 265-274.
5. Mayne S T, et al. Previous lung disease and risk of lung cancer among men and women nonsmokers. Am J Epidemiol 1999, 149, 13-20.
6. Nomura a, et al. Prospective study of pulmonary function and lung cancer. Am Rev Respir Dis 1991, 144, 307-311.
7. Schwartz A G. Genetic predisposition to lung cancer. Chest 2004, 125, 86s-89s.
8. Skillrud D M, et al. Higher risk of lung cancer in COPD: a prospective matched controlled study. Ann Int Med 1986, 105, 503-507.

9. Tockman M S, et al. Airways obstruction and the risk for lung cancer. Ann Int Med 1987, 106, 512-518.
10. Wu X, Zhao H, Suk R, Christiani D C. Genetic susceptibility to tobacco-related cancer. Oncogene 2004, 23, 6500-6523.

\*\*\*

All patents, publications, scientific articles, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Any and all materials and information from the above patents, publications, scientific articles, web sites, electronically available information, and other referenced materials or documents can be physically incorporated into this specification.

The specific methods and compositions described herein are representative. of various embodiments or preferred embodiments and are exemplary only and not intended as limitations on the scope of the invention. Other objects, aspects, examples and embodiments will occur to those skilled in the art upon consideration of this specification, and are encompassed within the spirit of the invention as defined by the scope of the claims. It will be readily apparent to one skilled in the art that varying substitutions and modifications can be made to the invention disclosed herein without departing from the scope and spirit of the invention. The invention illustratively described herein suitably can be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" can be replaced with either of the other two terms in the specification, thus indicating additional examples, having different scope, of various alternative embodiments of the invention. Also, the terms "comprising", "including", containing", etc. are to be read expansively and without limitation. The methods and processes illustratively described herein suitably can be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing during the prosecution of the application.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed can be resorted to by those skilled in the art, and that such modifications and variations are considered to be within the scope of this invention as defined by the appended claims.

What is claimed is:

1. A method of determining a human subject's increased risk of developing lung cancer when exposed to at least fifteen pack years of tobacco smoking, comprising:

obtaining a sample from said subject and detecting a genotype of CC at position -133 in the promoter of the gene encoding Interleukin-18 and a genotype of AT or TT at position -251 in the gene encoding Interleukin-8 (IL-8); wherein the presence of the genotype indicates an increased risk for developing lung cancer when exposed to at least fifteen pack years of tobacco smoking.

2. The method according to claim 1, wherein said method further comprises the analysis of one or more epidemiological risk factors.

* * * * *